(12) United States Patent
Benting et al.

(10) Patent No.: US 8,999,956 B2
(45) Date of Patent: *Apr. 7, 2015

(54) N-[(HET)ARYLALKYL)] PYRAZOLE(THIO)CARBOXAMIDES AND THEIR HETEROSUBSTITUTED ANALOGUES

(75) Inventors: Jurgen Benting, Leichlingen (DE); Pierre-Yves Coqueron, Lyons (FR); Pierre Cristau, Lyons (FR); Peter Dahmen, Neuss (DE); Philippe Desbordes, Lyons (FR); Stephanie Gary, Champagne-au-Mont-d'Or (FR); Jorg Greul, Leichlingen (DE); Hiroyuki Hadano, Shimotsuke (JP); Ruth Meissner, Leverkusen (DE); Ulrike Wachendorff-Neumann, Neuwied (DE)

(73) Assignee: Bayer Intellectual Property GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/700,716

(22) PCT Filed: Jun. 1, 2011

(86) PCT No.: PCT/EP2011/059026

§ 371 (c)(1), (2), (4) Date: Nov. 28, 2012

(87) PCT Pub. No.: WO2011/151370

PCT Pub. Date: Dec. 8, 2011

(65) Prior Publication Data

US 2013/0079302 A1    Mar. 28, 2013

Related U.S. Application Data

(60) Provisional application No. 61/368,003, filed on Jul. 27, 2010.

(30) Foreign Application Priority Data

Jun. 3, 2010  (EP) ..................................... 10356020
Nov. 15, 2010  (EP) ..................................... 10356032

(51) Int. Cl.
A01N 43/56     (2006.01)
C07D 231/16    (2006.01)
C07D 401/12    (2006.01)
C07F 7/10      (2006.01)
C07D 403/12    (2006.01)
C07D 405/12    (2006.01)
C07D 409/12    (2006.01)

(52) U.S. Cl.
CPC .............. *C07D 231/16* (2013.01); *A01N 43/56* (2013.01); *C07D 401/12* (2013.01); *C07D 403/12* (2013.01); *C07D 405/12* (2013.01); *C07D 409/12* (2013.01); *C07F 7/10* (2013.01)

(58) Field of Classification Search
None
See application file for complete search history.

(56) References Cited

U.S. PATENT DOCUMENTS

| 8,226,966 B2 | 7/2012 | Desbordes et al. | 424/405 |
| 8,410,157 B2 | 4/2013 | Desbordes et al. | 514/406 |
| 2010/0292239 A1 | 11/2010 | Stierli et al. | 514/249 |
| 2011/0092558 A1 | 4/2011 | Stierli et al. | 514/406 |
| 2011/0136874 A1 | 6/2011 | Bennabi et al. | 514/341 |

FOREIGN PATENT DOCUMENTS

| WO | WO 2009/012998 | 1/2009 |
| WO | WO 2009/016220 A1 | 2/2009 |
| WO | WO 2009/016221 | 2/2009 |
| WO | WO 2009/127718 | 10/2009 |
| WO | WO 2010/012795 | 2/2010 |
| WO | WO 2010/015681 | 2/2010 |
| WO | WO 2011/151368 | 12/2011 |
| WO | WO 2011/151369 | 12/2011 |

OTHER PUBLICATIONS

U.S. Appl. No. 13/700,433 corresponding to PCT/EP2011/059024, having an International filing date of Jun. 1, 2011, published as WO 2011/151368 by Jurgen Benting et al.
U.S. Appl. No. 13/700,501 corresponding to PCT/EP2011/059025, having an International filing date of Jun. 1, 2011, published as WO 2011/151369 by Jurgen Benting, et al.
International Search Report issued Aug. 25, 2011 in corresponding International Application No. PCT/EP2011/059026.

*Primary Examiner* — Kamal Saeed
(74) *Attorney, Agent, or Firm* — Ostrolenk Faber LLP

(57) ABSTRACT

The present invention relates to fungicidal N-[(het)arylalkyl)] pyrazolecarboxamide or thiocarboxamide and their heterosubstituted analogs, their process of preparation and intermediate compounds for their preparation, their use as fungicides, particularly in the form of fungicidal compositions and methods for the control of phytopathogenic fungi of plants using these compounds or their compositions.

25 Claims, No Drawings

N-[(HET)ARYLALKYL)] PYRAZOLE(THIO)CARBOXAMIDES AND THEIR HETEROSUBSTITUTED ANALOGUES

CROSS-REFERENCE TO RELATED APPLICATION(S)

The present application is a 35 U.S.C. §371 national phase conversion of PCT/EP2011/059026 filed on Jun. 1, 2011, which claims priority of European Application No. 10356020.7 filed on Jun. 3, 2010, U.S. Provisional Application No. 61/368,003 filed on Jul. 27, 2010, and European Application No. 10356032.2 filed on Nov. 15, 2010. Applicants claim priority to each of the foregoing patent applications. The PCT International Application was published in the English language.

The present invention relates to fungicidal N-[(het)arylalkyl)]pyrazolecarboxamide or thiocarboxamide and their heterosubstituted analogues, their process of preparation and intermediate compounds for their preparation, their use as fungicides, particularly in the form of fungicidal compositions and methods for the control of phytopathogenic fungi of plants using these compounds or their compositions.

In international patent applications WO-2008/003746 and WO-2010/015681 certain fungicidal pyrazolecarboxamide derivatives are generically embraced in a broad disclosure of numerous compounds of the following formula:

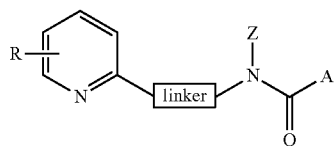

wherein A represents a substituted 5-membered heterocyclic group that can represent various rings among which a pyrazole ring, Z can represent a hydrogen atom, an alkyl group or a cycloalkyl group and the substituted or non-substituted 2-pyridyl group is linked to the pyrazolecarboxamide moiety by means of a 3- or 4-atoms linker. However, there is no explicit disclosure or suggestion to select in these documents of any such derivative wherein A represent a 1-alkyl-3-(difluoro or dichloro)methyl-5-(chloro or fluoro)-4-pyrazolyl group.

In international patent applications WO-2008/101976, WO-2009/012998, WO-2009/127718, WO-2009/127722, WO-2009/127726, WO-2010/012795, WO-2010/063700, WO-2010/106071 and WO-2011/045355 certain fungicidal pyrazole-carboxamide derivatives are generically embraced in a broad disclosure of numerous compounds of the following formula:

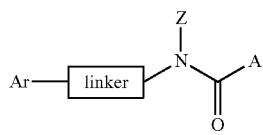

wherein A represents a substituted 5-membered heterocyclic group that can represent various rings among which a pyrazole ring, Z can represent a hydrogen atom, an alkyl group, an alkoxy group or a cycloalkyl group and Ar can represent a substituted or non-substituted phenyl or naphthyl group which is linked to the pyrazolecarboxamide moiety by means of a 3-, 4- or 5-atoms linker. However, there is no explicit disclosure or suggestion to select in these documents of any such derivative wherein A represent a 1-alkyl-3-(difluoro or dichloro)methyl-5-(chloro or fluoro)-4-pyrazolyl group.

In international patent applications WO-1998/003486, WO-2006/061215, WO-2007/0039615 and WO-2008/081017 certain fungicidal pyrazolecarboxamide derivatives are generically embraced in a broad disclosure of numerous compounds of the following formula:

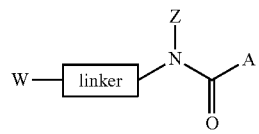

wherein A represents a substituted 5-membered heterocyclic group that can represent various rings among which a pyrazole ring, Z can represent a hydrogen atom, an alkyl group or a cycloalkyl group and W can represent various substituted or non-substituted groups among which an alkyl group, a cycloalkylgroup, a trialkylsilyl group or a alkynyl group which are linked to the pyrazolecarboxamide moeity by means of a 2-, 3- or 4-atoms linker. However, there is no explicit disclosure or suggestion to select in these documents of any such derivative wherein A represent a 1-alkyl-3-(difluoro or dichloro)methyl-5-(chloro or fluoro)-4-pyrazolyl group.

It is always of high-interest in the field of agrochemicals to use pesticidal compounds more active than the compounds already known by the man ordinary skilled in the art whereby reduced amounts of compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

Accordingly, the present invention provides a N-[(het)arylalkyl)]pyrazolecarboxamide or thiocarboxamide derivative of formula (I)

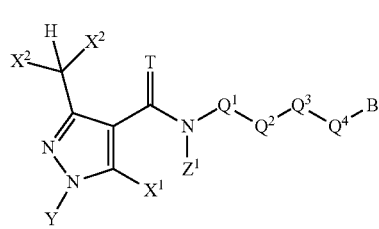

wherein
X$^1$ and X$^2$ which can be the same or different, represent a halogen atom;
Y represents a C$_1$-C$_4$-alkyl;
T represents O or S;
Q$^1$ represents CR$^1$R$^2$; —CR$^3$=CR$^4$—; —CR$^3$=N—O—; or —C(=W)—;
Q$^2$, Q$^3$ and Q$^4$, which can be the same or different, represent a direct bond; CR$^1$R$^2$; —CR$^3$=CR$^4$—; —C=C—; —CR$^3$=N—O—; —O—N=CR$^3$—; O; S; SO; SO$_2$; NR$^5$; SiR$^6$R$^7$; or —C(=U)—;

B represents a phenyl ring that can be substituted by up to 5 groups X which can be the same or different; a naphthyl ring that can be substituted by up to 7 groups X which can be the same or different; a saturated, partially saturated or unsaturated, monocyclic or fused bicyclic 4-, 5-, 6-, 7-, 8-, 9-, 10-membered ring comprising from 1 up to 4 heteroatoms selected in the list consisting of N, O, S, that can be substituted by up to 6 groups X which can be the same or different; a hydrogen atom; a halogen atom; a substituted or non-substituted $C_1$-$C_{12}$-alkyl group; a $C_1$-$C_{12}$-halogenoalkyl group having 1 to 9 halogen atoms that can be the same or different; a substituted or non-substituted $C_3$-$C_8$-cycloalkyl group; a substituted or non-substituted $C_3$-$C_8$-cycloalkenyl group, a bicyclo[2.2.1]heptan-2-yl group; a tri($C_1$-$C_8$-alkyl)silyl group; a substituted or non-substituted $C_2$-$C_{12}$ alkenyl group; or a substituted or non-substituted $C_2$-$C_{12}$ alkynyl group;

X represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$-alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$-alkyl)silyl; substituted or non-substituted tri($C_1$-$C_8$-alkyl)silyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl-carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$-alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; $C_1$-$C_8$-arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; or $C_1$-$C_8$-arylalkylamino that can be substituted by up to 6 groups Q which can be the same or different; or two substituent X together with the consecutive carbon atoms to which they are linked can form a 5- or 6-membered, saturated carbocycle or saturated heterocycle, which can be substituted by up to four groups Q which can be the same or different;

$Z^1$ represents a hydrogen atom; a formyl group; a substituted or non-substituted $C_1$-$C_8$-alkyl; a substituted or non substituted $C_1$-$C_8$-alkoxy; a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

$R^1$ and $R^2$ independently represent a hydrogen atom; a halogen atom; cyano; substituted or non-substituted $C_1$-$C_{12}$-alkyl; substituted or non-substituted $C_2$-$C_{12}$-alkenyl; substituted or non-substituted $C_2$-$C_{12}$-alkynyl; substituted or non-substituted $C_3$-$C_7$-cycloalkyl; $C_1$-$C_{12}$-halogenoalkyl having 1 to 5 halogen atoms; substituted or non-substituted $C_1$-$C_8$-alkoxy; substituted or non-substituted $C_1$-$C_8$-alkylsulfanyl; substituted or non-substituted $C_1$-$C_8$-alkylamino; substituted or non-substituted di-($C_1$-$C_8$-alkyl)amino; or substituted or non-substituted $C_1$-$C_8$-alkoxycarbonyl; or $R^1$ and $R^2$ are a $C_2$-$C_8$-alkylene group that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different; or The $R^1$ substituent of the group $Q^i$ and the $R^1$ substituent of the group $Q^{i+1}$, i being an integer between 1 and 3, together with the consecutive carbon atoms to which they are linked can form a 3-, 4-, 5-, 6- or 7-membered saturated carbocycle that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different; or The $R^1$ substituent of the group $Q^i$ and the $R^1$ substituent of the group $Q^{i+2}$, i being an integer between 1 and 2, together with the consecutive carbon atoms to which they are linked can form a 3-, 4-, 5-, 6- or 7-membered saturated carbocycle that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different;

$R^3$ and $R^4$ independently represent a hydrogen atom; substituted or non-substituted $C_1$-$C_8$-alkyl; substituted or non-substituted $C_2$-$C_8$-alkenyl; substituted or non-substituted $C_2$-$C_8$-alkynyl; substituted or non-substituted $C_3$-$C_7$-cycloalkyl; or $C_1$-$C_8$-halogenoalkyl having 1 to 5 halogen atoms; $R^5$ represents a hydrogen atom; a substituted or non-substituted $C_1$-$C_8$-alkyl; a $C_1$-$C_8$-halogenoalkyl comprising up to 9 halogen atoms that can be the same or different; a substituted or non-substituted $C_2$-$C_8$-alkenyl; a $C_2$-$C_8$-halogenoalkenyl comprising up to 9 halogen atoms that can be the same or different; a substituted or non-substituted $C_3$-$C_8$-alkynyl; a $C_3$-$C_8$-halogenoalkynyl comprising up to 9 halogen atoms that can be the same or different; a substituted or non-substituted $C_3$-$C_7$-cycloalkyl; a $C_3$-$C_7$-halogeno-cycloalkyl comprising up to 9 halogen atoms that can be the same or different; a substituted or non-substituted $C_3$-$C_7$-cycloalkyl-$C_1$-$C_8$-alkyl; formyl; a substituted or non-substituted $C_1$-$C_8$-alkylcarbonyl; $C_1$-$C_8$-halogenoalkylcarbonyl comprising up to 9 halogen atoms that can be the same or different; a substituted or non-substituted $C_1$-$C_8$-alkoxycarbonyl; $C_1$-$C_8$-halogenoalkoxycarbonyl comprising up to 9 halogen atoms that can be the same or different; a substituted or non-substituted $C_1$-$C_8$-alkylsulphonyl; $C_1$-$C_8$-halogenoalkylsulphonyl comprising up to 9 halogen atoms that can be the same or different; phenylmethylene that can be substituted by up to 7 groups Q which can be the same or different; or phenylsulphonyl that can be substituted by up to 5 groups Q which can be the same or different;

$R^6$ and $R^7$ independently represent a substituted or non-substituted $C_1$-$C_8$-alkyl;

W represents O; or S;

U represents O; S; N—$OR^a$; or N—CN;

$R^a$ represents a hydrogen atom; a substituted or non-substituted $C_1$-$C_4$-alkyl; or a $C_1$-$C_4$-halogenoalkyl comprising up to 7 halogen atoms that can be the same or different;

Q independently represents a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; substituted or non-substituted (benzyloxyimino)-$C_1$-$C_8$-alkyl;

with the provisio that -$Q^1$-$Q^2$-$Q^3$-$Q^4$- does not represent $CR^1R^2$ when B represents a substituted or non-substituted phenyl, naphthyl or 2-pyridyl ring;

or that -$Q^1$-$Q^2$-$Q^3$-$Q^4$- does not represent $[CR^1R^2]_2$ or $CR^1R^2$—C(=W)— or a cycloalkyl-1,2-diyl group, when B represents a substituted or non-substituted phenyl, naphthyl or heterocyclic ring;

or that $Z^1$ does not represent a hydrogen atom when -$Q^1$-$Q^2$- represents a unsubstituted cyclohexyl-1,2-diyl group and -$Q^3$-$Q^4$- represents a substituted or non-substituted cyclopropyl-1,2-diyl group;

as well as its salts, N-oxydes, metallic complexes, metalloidic complexes and optically active isomers.

For the compounds according to the invention, the following generic terms are generally used with the following meanings:

halogen means fluorine, bromine, chlorine or iodine.
carboxy means —C(=O)OH;
carbonyl means —C(=O)—;
carbamoyl means —C(=O)$NH_2$;
N-hydroxycarbamoyl means —C(=O)NHOH;
SO represents a sulfoxyde group;
$SO_2$ represents a sulfone group;
an alkyl group, an alkenyl group and an alkynyl group as well as moieties containing these terms, can be linear or branched;
the aryl moeity contained in an aryl group, an arylalkyl group, an arylalkenyl group and an arylalkynyl group as well as moieties containing these terms, can be a phenyl group that can be substituted by up to 5 groups Q which can be the same or different, a naphthyl group that can be substituted by up to 7 groups Q which can be the same or different or a pyridyl group that can be substituted by up to 4 groups Q which can be the same or different;
and, heteroatom means sulphur, nitrogen or oxygen.
in the case of an amino group or the amino moiety of any other amino-comprising group, substituted by two substituent that can be the same or different, the two substituent together with the nitrogen atom to which they are linked can form a heterocyclyl group, preferably a 5- to 7-membered heterocyclyl group, that can be substituted or that can include other hetero atoms, for example a morpholino group or piperidinyl group.
unless indicated otherwise, a group or a substituent that is substituted according to the invention can be substituted by one or more of the following groups or atoms: a halogen atom, a nitro group, a hydroxy group, a cyano group, an amino group, a sulfanyl group, a pentafluoro-$\lambda^6$-sulfanyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulfanyl, a $C_1$-$C_8$-halogenoalkylsulfanyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulfinyl, a $C_1$-$C_8$-halogenoalkylsulfinyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a 2-oxopyrrolidin-1-yl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulfanyl, benzylamino, phenoxy, phenylsulfanyl, or phenylamino.

Any of the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Any of the compounds of formula (I) wherein X represents a hydroxy, a sulfanyl group or an amino group may be found in its tautomeric form resulting from the shift of the proton of said hydroxy, sulfanyl or amino group. Such tautomeric forms of such compounds are also part of the present invention. More generally speaking, all tautomeric forms of compounds of formula (I) wherein X represents a hydroxy, a sulfanyl group or an amino group, as well as the tautomeric forms of the compounds which can optionally be used as intermediates in the preparation processes and which will be defined in the description of these processes, are also part of the present invention.

Preferred compounds according to the invention are compounds of formula (I) wherein $X^1$ and $X^2$ independently represent a chlorine or a fluorine atom. More preferred compounds according to the invention are compounds of formula (I) wherein $X^1$ and $X^2$ represent a fluorine atom;

Other preferred compounds according to the invention are compounds of formula (I) wherein Y represents methyl;

Other preferred compounds according to the invention are compounds of formula (I) wherein T represents O;

Other preferred compounds according to the invention are compounds of formula (I) wherein B represents a substituted or non-substituted phenyl ring; a substituted or non-substituted naphthyl ring; a substituted or non-substituted pyridyl ring; a substituted or non-substituted thienyl ring; or a substituted or non-substituted benzothienyl ring; more preferred compounds according to the invention are compounds of formula (I) wherein B represents a substituted or non-substituted phenyl ring; other more preferred compounds according to the invention are compounds of formula (I) wherein B represents a substituted or non-substituted 2-pyridyl ring;

Other preferred compounds according to the invention are compounds of formula (I) wherein X independently represents a halogen atom; substituted or non-substituted $C_1$-$C_8$-alkyl; $C_1$-$C_8$-halogenoalkyl comprising up to 9 halogen atoms that can be the same or different; substituted or non-substituted tri($C_1$-$C_8$-alkyl)silyl; substituted or non-substituted $C_1$-$C_8$-alkoxy or $C_1$-$C_8$-halogenoalkoxy comprising up to 9 halogen atoms that can be the same or different; substituted or non-substituted $C_1$-$C_8$-alkylsulfanyl or $C_1$-$C_8$-halogenoalkylsulfanyl comprising up to 9 halogen atoms that can be the same or different; or wherein two consecutive substituents X together with the phenyl ring form a substituted or non-substituted cyclopentyl or cyclohexyl ring;

Even more preferred compounds according to the invention are compounds of formula (I) wherein X independently represents fluorine, chlorine, bromine, iodine, methyl, ethyl, propyl, isopropyl, butyl, isobutyl, secbutyl, terbutyl, cyclopropyl, cyclopentyl, cyclohexyl, trimethylsilyl, methoxy, ethoxy, methylsulfanyl, ethylsulfanyl, trifluoromethyl, trichloromethyl, difluoromethoxy, trifluoromethoxy, difluorochloromethoxy, trifluoroethoxy, difluoromethysulfanyl, trifluoromethylsulfanyl and difluorochloro-methylsulfanyl;

Other preferred compounds according to the invention are compounds of formula (I) wherein $Z^1$ represents a hydrogen atom; a non-substituted $C_3$-$C_7$ cycloalkyl; or a $C_3$-$C_7$ cycloalkyl substituted by up to 10 groups or atoms that can be the same or different and that can be selected in the list consisting of halogen atoms, $C_1$-$C_8$-alkyl, $C_1$-$C_8$-halogenoalkyl comprising up to 9 halogen atoms that can be the same or different, $C_1$-$C_8$-alkoxy and $C_1$-$C_8$-halogenoalkoxy comprising up to 9 halogen atoms that can be the same or different; more preferably $Z^1$ represents a non-substituted $C_3$-$C_7$-cycloalkyl; even more preferably $Z^1$ represents cyclopropyl;

Other preferred compounds according to the invention are compounds of formula (I) wherein $Q^1$ represents $CR^1R^2$;

Other preferred compounds according to the invention are compounds of formula (I) wherein $Q^2$, $Q^3$ and $Q^4$, which can be the same or different, represents a direct bond; $CR^1R^2$; or O;

More preferred compounds according to the invention are compounds of formula (I) wherein $Q^2$ represents $CR^1R^2$ and $Q^3$ and $Q^4$ represent a direct bond;

Other more preferred compounds according to the invention are compounds of formula (I) wherein $Q^2$ represents $CR^1R^2$ and $Q^3$ represents O and $Q^4$ represent a direct bond;

Other preferred compounds according to the invention are compounds of formula (I) wherein $R^1$ and $R^2$ independently represent a hydrogen atom, a fluorine atom, a substituted or non-substituted $C_1$-$C_8$-alkyl or a substituted or non-substituted $C_1$-$C_8$-alkoxy;

Other preferred compounds according to the invention are compounds of formula (I) wherein the $R^1$ substituent of the group $Q^i$ and the $R^1$ substituent of the group $Q^{i+1}$, i being an integer between 1 and 3, together with the consecutive carbon atoms to which they are linked can form an optionally mono or polysubstituted 3-, 4-, 5-, 6- or 7-membered saturated carbocycle; more preferably an optionally mono or polysubstituted cyclopropyl, cyclopentyl, cyclohexyl or a cycloheptyl ring; even more preferably a cyclopropyl, a cyclopentyl or a cyclohexyl ring;

Other more preferred compounds according to the invention are compounds of formula (I) wherein the $R^1$ substituent of the group $Q^i$ and the $R^1$ substituent of the group $Q^{i+1}$, i being an integer between 1 and 3, together with the consecutive carbon atoms to which they are linked can form an cyclopentyl group that can be substituted by up to three groups that can be the same or different and that can be selected in the list consisting of fluorine, chlorine, methyl, ethyl, propyl, isopropyl, isobutyl, secbutyl, terbutyl, trifluoromethyl or difluoromethyl;

Other more preferred compounds according to the invention are compounds of formula (I) wherein the $R^1$ substituent of the group $Q^i$ and the $R^1$ substituent of the group $Q^{i+1}$, i being an integer between 1 and 3, together with the consecutive carbon atoms to which they are linked can form an cyclohexyl group that can be substituted by up to four groups that can be the same or different and that can be selected in the list consisting of fluorine, chlorine, methyl, ethyl, propyl, isopropyl, isobutyl, secbutyl, terbutyl, trifluoromethyl or difluoromethyl;

Other more preferred compounds according to the invention are compounds of formula (I) wherein the $R^1$ substituent of the group $Q^i$ and the $R^1$ substituent of the group $Q^{i+1}$, i being an integer between 1 and 3, together with the consecutive carbon atoms to which they are linked can form an cycloheptyl group that can be substituted by up to four groups that can be the same or different and that can be selected in the list consisting of fluorine, chlorine, methyl, ethyl, propyl, isopropyl, isobutyl, secbutyl, terbutyl, trifluoromethyl or difluoromethyl;

Even more preferred compounds according to the invention are compounds of formula (I) wherein -$Q^1$-$Q^2$- represents an optionally mono or polysubstituted cyclopentyl-1,2-diyl, cyclohexyl-1,2-diyl or cycloheptyl-1,2-diyl group and -$Q_3$-$Q_4$-B represents a bicyclo[2.2.1]heptan-2-yl group, $A^1$, $A^2$, $A^3$ or $A^4$ wherein $A^1$ represents

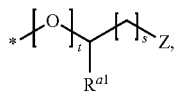

wherein
$R^{a1}$ represents hydrogen, $C_1$-$C_4$-alkyl or $C_1$-$C_4$-haloalkyl;
Z represents —$CR^{a2}R^{a3}R^{a4}$ or —$SiR^{a2}R^{a3}R^{a4}$;
s represents 0, 1, 2 or 3;
t represents 0 or 1;
$R^{a2}$, $R^{a3}$, $R^{a4}$ independently of one another represent hydrogen, halogen $C_1$-$C_4$-alkyl or $C_1$-$C_4$-haloalkyl;
$R^{a3}$ and $R^{a4}$ furthermore together with the carbon atom to which they are attached, can form an optionally substituted saturated or insaturated 3- to 6-membered carbocyclic ring;
Particularly preferably,
$R^{a1}$ represents hydrogen or methyl;
s represents 0 or 1;
$R^{a2}$ represents chlorine, methyl, ethyl, isopropyl or trifluoromethyl;
$R^{a1}$ represents chlorine, methyl, ethyl, isopropyl or trifluoromethyl;
$R^{a4}$ represents hydrogen, chlorine, methyl, ethyl, isopropyl or trifluoromethyl;

$A^2$ represents

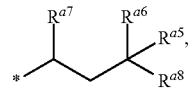

wherein
$R^{a6}$ represent hydrogen, halogen, $C_1$-$C_8$-alkyl or $C_1$-$C_8$-haloalkyl;
$R^{a5}$, $R^{a7}$, $R^{a8}$ independently of one another represent hydrogen, methyl or ethyl; Particularly preferably,
$R^{a5}$ represents hydrogen or methyl;
$R^{a6}$ represents hydrogen;
$R^{a7}$ represents hydrogen or methyl;
$R^{a8}$ represents fluorine, chlorine, methyl, ethyl or trifluoromethyl;
$A^3$ represents

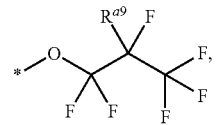

wherein
$R^{a9}$ represent hydrogen or fluorine;
$A^4$ represents

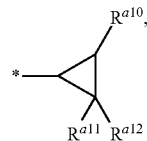

wherein
$R^{a10}$ represent optionally substituted $C_2$-$C_{12}$-alkyl, optionally substituted $C_2$-$C_{12}$-alkenyl, optionally substituted $C_2$-$C_{12}$-alkynyl, optionally substituted $C_3$-$C_8$-cycloalkyl, optionally substituted phenyl or heterocyclyl;
$R^{a11}$ represent hydrogen or halogen;
$R^{a12}$ represent hydrogen or halogen;
Particularly preferably,
$R^{a10}$ represents ethyl, propyl, isopropyl, butyl, secbutyl, terbutyl, cyclopropyl, cyclobutyl, cyclopentyl, cyclohexyl, α-methylcyclopropyl, 4-fluorophenyl, 4-bromophenyl, 2-thienyl, 3-thienyl or 2-fury;
$R^{a11}$ represents hydrogen;
$R^{a12}$ represents hydrogen;
Other preferred compounds according to the invention are compounds of formula (I) wherein the $R^1$ substituent of the group $Q^i$ and the $R^1$ substituent of the group $Q^{i+2}$, i being an integer between 1 and 2, together with the consecutive carbon atoms to which they are linked can form an optionally mono or polysubstituted 4-, 5-, 6- or 7-membered saturated carbocycle; more preferably an optionally mono or polysubstituted cyclopentyl, cyclohexyl or a cycloheptyl ring; even more preferably a cyclohexyl ring;

Other more preferred compounds according to the invention are compounds of formula (I) wherein the $R^1$ substituent of the group $Q^i$ and the $R^1$ substituent of the group $Q^{i+2}$, i being an integer between 1 and 2, together with the consecutive carbon atoms to which they are linked can form an cyclohexyl group that can be substituted by up to four groups that can be the same or different and that can be selected in the list consisting of fluorine, chlorine, methyl, ethyl, propyl, isopropyl, isobutyl, secbutyl, terbutyl, trifluoromethyl or difluoromethyl;

Even more preferred compounds according to the invention are compounds of formula (I) wherein -$Q^1$-$Q^2$-$Q^3$- represents an optionally mono or polysubstituted cyclohexyl-1,3-diyl and -$Q_4$-B represents a bicyclo[2.2.1]heptan-2-yl group, or a $A^1$, $A^2$, $A^3$ or $A^4$ group as defined above.

Other preferred compounds according to the invention are compounds of formula (I) wherein $R^3$ and $R^4$ independently represent a hydrogen atom, or a substituted or non-substituted $C_1$-$C_8$-alkyl;

Other preferred compounds according to the invention are compounds of formula (I) wherein $R^5$ represents a substituted or non-substituted $C_1$-$C_8$-alkyl;

Other preferred compounds according to the invention are compounds of formula (I) wherein $R^6$ and $R^7$ independently represent a non-substituted $C_1$-$C_8$-alkyl;

More preferably, $R^6$ and $R^7$ independently represent a non-substituted $C_1$-$C_3$-alkyl;

Even more preferably, $R^6$ and $R^7$ represent methyl

Other preferred compounds according to the invention are compounds of formula (I) wherein U represents O.

Other preferred compounds according to the invention are compounds of formula (I) wherein U represents N—O—($C_1$-$C_4$-alkyl).

The above mentioned preferences with regard to the substituents of the compounds according to the invention can be combined in various manners. These combinations of preferred features thus provide sub-classes of compounds according to the invention. Examples of such sub-classes of preferred compounds according to the invention can be combined:

preferred features of $X^1$ with preferred features of $X^2$, Y, T, B, $Z^1$, $Q^1$, $Q^2$, $Q^3$, $Q^4$, $R^1$, $R^2$, $R^3$, $R^4$, $R^5$, $R^6$, $R^7$, X and U;

preferred features of $X^2$ with preferred features of $X^1$, Y, T, B, $Z^1$, $Q^1$, $Q^2$, $Q^3$, $Q^4$, $R^1$, $R^2$, $R^3$, $R^4$, $R^5$, $R^6$, $R^7$, X and U;

preferred features of Y with preferred features of $X^1$, $X^2$, T, B, $Z^1$, $Q^1$, $Q^2$, $Q^3$, $Q^4$, $R^1$, $R^2$, $R^3$, $R^4$, $R^5$, $R^6$, $R^7$, X and U;

preferred features of T with preferred features of $X^1$, $X^2$, Y, B, $Z^1$, $Q^1$, $Q^2$, $Q^3$, $Q^4$, $R^1$, $R^2$, $R^3$, $R^4$, $R^5$, $R^6$, $R^7$, X and U;

preferred features of B with preferred features of $X^1$, $X^2$, Y, T, $Z^1$, $Q^1$, $Q^2$, $Q^3$, $Q^4$, $R^1$, $R^2$, $R^3$, $R^4$, $R^5$, $R^6$, $R^7$, X and U;

preferred features of $Z^1$ with preferred features of $X^1$, $X^2$, Y, T, B, $Q^1$, $Q^2$, $Q^3$, $Q^4$, $R^1$, $R^2$, $R^3$, $R^4$, $R^5$, $R^6$, $R^7$, X and U;

preferred features of $Q^1$ with preferred features of $X^1$, $X^2$, Y, T, B, $Z^1$, $Q^2$, $Q^3$, $Q^4$, $R^1$, $R^2$, $R^3$, $R^4$, $R^5$, $R^6$, $R^7$, X and U;

preferred features of $Q^2$ with preferred features of $X^1$, $X^2$, Y, T, B, $Z^1$, $Q^1$, $Q^3$, $Q^4$, $R^1$, $R^2$, $R^3$, $R^4$, $R^5$, $R^6$, $R^7$, X and U;

preferred features of $Q^3$ with preferred features of $X^1$, $X^2$, Y, T, B, $Z^1$, $Q^1$, $Q^2$, $Q^4$, $R^1$, $R^2$, $R^3$, $R^4$, $R^5$, $R^6$, $R^7$, X and U;

preferred features of $Q^4$ with preferred features of $X^1$, $X^2$, Y, T, B, $Z^1$, $Q^1$, $Q^2$, $Q^3$, $R^1$, $R^2$, $R^3$, $R^4$, $R^5$, $R^6$, $R^7$, X and U;

preferred features of $R^1$ with preferred features of $X^1$, $X^2$, Y, T, B, $Z^1$, $Q^1$, $Q^2$, $Q^3$, $Q^4$, $R^2$, $R^3$, $R^4$, $R^5$, $R^6$, $R^7$, X and U;

preferred features of $R^2$ with preferred features of $X^1$, $X^2$, Y, T, B, $Z^1$, $Q^1$, $Q^2$, $Q^3$, $Q^4$, $R^1$, $R^3$, $R^4$, $R^5$, $R^6$, $R^7$, X and U;

preferred features of $R^3$ with preferred features of $X^1$, $X^2$, Y, T, B, $Z^1$, $Q^1$, $Q^2$, $Q^3$, $Q^4$, $R^1$, $R^2$, $R^4$, $R^5$, $R^6$, $R^7$, X and U;

preferred features of $R^4$ with preferred features of $X^1$, $X^2$, Y, T, B, $Z^1$, $Q^1$, $Q^2$, $Q^3$, $Q^4$, $R^1$, $R^2$, $R^3$, $R^5$, $R^6$, $R^7$, X and U;

preferred features of $R^5$ with preferred features of $X^1$, $X^2$, Y, T, B, $Z^1$, $Q^1$, $Q^2$, $Q^3$, $Q^4$, $R^1$, $R^2$, $R^3$, $R^4$, $R^6$, $R^7$, X and U;

preferred features of $R^6$ with preferred features of $X^1$, $X^2$, Y, T, B, $Z^1$, $Q^1$, $Q^2$, $Q^3$, $Q^4$, $R^1$, $R^2$, $R^3$, $R^4$, $R^5$, $R^7$, X and U;

preferred features of $R^7$ with preferred features of $X^1$, $X^2$, Y, T, B, $Z^1$, $Q^1$, $Q^2$, $Q^3$, $Q^4$, $R^1$, $R^2$, $R^3$, $R^4$, $R^5$, $R^6$, X and U;

preferred features of X with preferred features of $X^1$, $X^2$, Y, T, B, $Z^1$, $Q^1$, $Q^2$, $Q^3$, $Q^4$, $R^1$, $R^2$, $R^3$, $R^4$, $R^5$, $R^6$, $R^7$ and U;

preferred features of U with preferred features of $X^1$, $X^2$, Y, T, B, $Z^1$, $Q^1$, $Q^2$, $Q^3$, $Q^4$, $R^1$, $R^2$, $R^3$, $R^4$, $R^5$, $R^6$, $R^7$, and X;

In these combinations of preferred features of the substituents of the compounds according to the invention, the said preferred features can also be selected among the more preferred features of each of $X^1$, $X^2$, Y, T, B, $Z^1$, $Q^1$, $Q^2$, $Q^3$, $Q^4$, $R^1$, $R^2$, $R^3$, $R^4$, $R^5$, $R^6$, $R^7$, X and U, so as to form most preferred subclasses of compounds according to the invention.

The present invention also relates to a process for the preparation of the compound of formula (I). Thus, according to a further aspect of the present invention there is provided a process P1 for the preparation of a compound of formula (I) as herein-defined and wherein T represents O and that comprises reacting a N-substituted amine derivative of formula (II) or one of its salts:

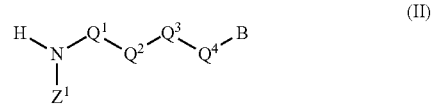
(II)

wherein $Z^1$, $Q^1$, $Q^2$, $Q^3$, $Q^4$ and B are as herein-defined; with a carboxylic acid derivative of formula (III):

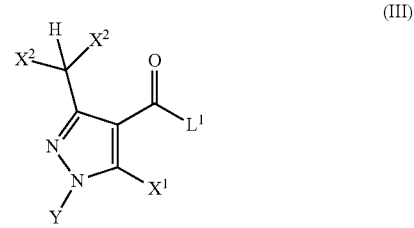
(III)

wherein $X^1$, $X^2$ and Y are as herein-defined and $L^1$ represents a leaving group selected in the list consisting of a halogen atom, a hydroxyl group, —$OR^b$, —OC(=O)$R^b$, $R^b$ being a substituted or non-substituted $C_1$-$C_6$-alkyl, a substituted or non-substituted $C_1$-$C_6$-haloalkyl, a benzyl, a 4-methoxybenzyl or a pentafluorophenyl group; in the presence of a catalyst and in the presence of a condensing agent in case $L^1$ represents a hydroxyl group, and in the presence of an acid binder in case $L^1$ represents a halogen atom.

N-substituted amine derivatives of formula (II) are known or can be prepared by known processes such as reductive amination of aldehyde or ketone (Bioorganics and Medicinal Chemistry Letters (2006), 2014), or reduction of imines (Tetrahedron (2005), 11689), or nucleophilic substitution of halogen, mesylate or tosylate (Journal of Medicinal Chemistry (2002), 3887).

Moreover, some amines of formula (II) are specifically known such as:
2-butylcyclohexanamine can be prepared according to Tetrahedron (1976), 23, 2421,
2-(4-methylpentan-2-yl)cyclohexanamine can be prepared according to WO-2006/061215,
2-(4,4-dimethylpentan-2-yl)cyclohexanamine can be prepared according to WO-2006/061215,
2-(3-methylbutyl)cyclohexanamine can be prepared according to WO-2006/061215,
2-(3,3-dimethylbutyl)cyclohexanamine can be prepared according to WO-2006/061215,
2-[3-(trimethysilyl)propyl]cyclohexanamine can be prepared according to WO-2006/061215,
2-isobutylcyclohexanamine can be prepared according to Tetrahedron (1997), 53, 4935,
2-propylcyclohexanamine can be prepared according to Journal of Combinatorial Chemistry (2005), 7, 109.

Carboxylic acid derivatives of formula (III) can be prepared according to process P2.

In case $L^1$ represents a hydroxy group, the process according to the present invention is conducted in the presence of condensing agent. Suitable condensing agent may be selected in the non limited list consisting of acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloro-methane, 4-(4,6-dimethoxy[1.3.5]-triazin-2-yl)-4-methylmorpholinium chloride hydrate or bromo-tripyrrolidino-phosphonium-hexafluoro-phosphate.

The process according to the present invention is conducted in the presence of a catalyst. Suitable catalyst may be selected in the list consisting of 4-dimethyl-aminopyridine, 1-hydroxy-benzotriazole or dimethylformamide.

In case $L^1$ represents a halogen atom, the process according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetateand also tertiary amines, such as trimethylamine, triethylamine, diisopropylethylamine, tributylamine, N,N-dimethylaniline, pyridine, N-methylpiperidine, N,N-dimethylaminopyridine, diazabicyclooctane (DABCO), diazabicyclo-nonene (DBN) or diazabicycloundecene (DBU).

It is also possible to work in the absence of an additional condensing agent or to employ an excess of the amine component, so that it simultaneously acts as acid binder agent.

According to a further aspect according to the invention, there is provided a process P2 for the preparation of carboxylic acid derivatives of formula (III) wherein T represents O and illustrated according to the following reaction scheme:

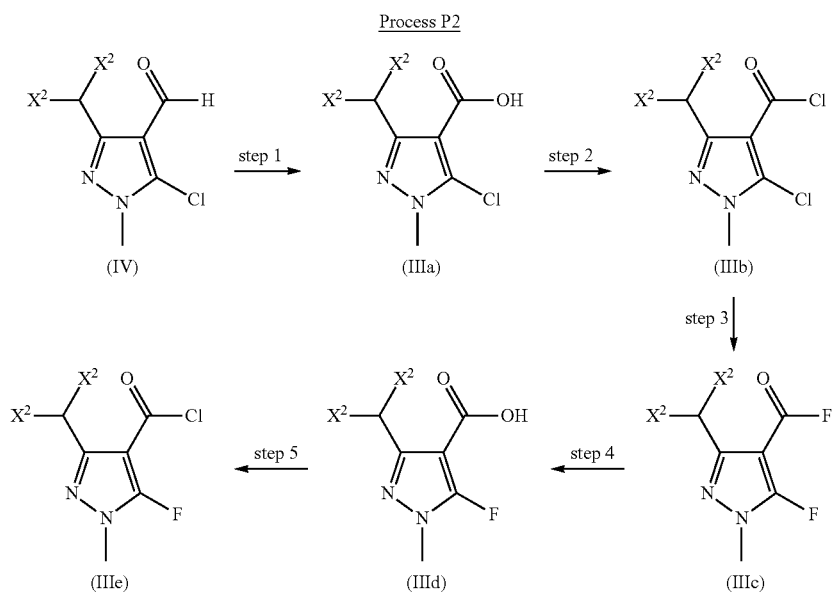

wherein $X^2$ is as herein-defined;

5-chloro-3-(difluoromethyl)-1-methyl-1H-pyrazole-4-carbaldehyde is known from WO-2004/014138 (reference example 35).

Step 1 of process P2 is performed in the presence of an oxidant, and if appropriate in the presence of a solvent.

Steps 2 and 5 of process P2 are performed in the presence of acid halide, and if appropriate in the presence of a solvent.

Step 3 of process P2 is performed in the presence of a fluorinating agent, and if appropriate in the presence of a solvent.

Step 4 of process P2 is performed in the presence of an acid or a base and if appropriate in the presence of a solvent Suitable oxidants for carrying out step 1 of process P2 according to the invention are in each case all inorganic and organic oxidant which are customary for such reactions. Preference is given to using benzyltriethylammonium permanganate, bromine, chlorine, m-chloroperbenzoic acid, chromic acid, chromium (VI) oxide, hydrogen peroxide, hydrogen peroxide-boron trifluoride, hydrogen peroxide-urea, 2-hydroxyperoxyhexafluoro-2-propanol; Iodine, oxygen-platinum catalyst, perbenzoic acid, peroxyacetyl nitrate, potassium permanganate, potassium ruthenate, pyridinium dichromate, ruthenium (VIII) oxide, silver (I) oxide, silver (II) oxide, silver nitrite, sodium chlorite, sodium hypochlorite, or 2,2,6,6-tetramethylpiperidin-1-oxyl.

Suitable acid halides for carrying out steps 2 and 5 of process P2 according to the invention are in each case all organic or inorganic acid halides which are customary for such reactions. Preference is given to using notably phosgene, phosphorous trichloride, phosphorous pentachloride, phosphorous trichloride oxide, thionyl chloride, or carbon tetrachloride-triphenylphosphine.

Suitable fluorinating agent for carrying out step 3 of process P2 according to the invention is in each case all fluorinating agents which are customary for such reactions. Preference is given to using cesium fluoride, potassium fluoride, potassium fluoride-calcium difluoride, or tetrabutylammonium fluoride.

When carrying out steps 1 to 5 of process P2 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use the micro-waves technology.

Steps 1 to 5 of process P2 according to the invention are generally independently carried out under atmospheric pressure. However, in each case, it is also possible to operate under elevated or reduced pressure.

When carrying out step 1 of process P2 according to the invention, generally one mole or other an excess of the oxidant is employed per mole of aldehyde of formula (IV). It is also possible to employ the reaction components in other ratios.

When carrying out carrying out steps 2 and 5 of process P2 to the invention, generally one mole or other an excess of the acid halides is employed per mole of acid of formula (IIIa) or (IIId). It is also possible to employ the reaction components in other ratios.

When carrying out steps 3 of process P2 according to the invention generally one mole or other an excess of fluorinating agent is employed per mole of acid chloride (IIIb). It is also possible to employ the reaction components in other ratios.

When carrying out steps 4 of process P2 according to the invention generally one mole or other an excess of acid or base is employed per mole of acid fluoride (IIIc). It is also possible to employ the reaction components in other ratios.

According to a further aspect according to the invention, there is provided a process P3 for the preparation of a compound of formula (I) wherein T represents S, starting from a compound of formula (I) wherein T represents O and illustrated according to the following reaction scheme:

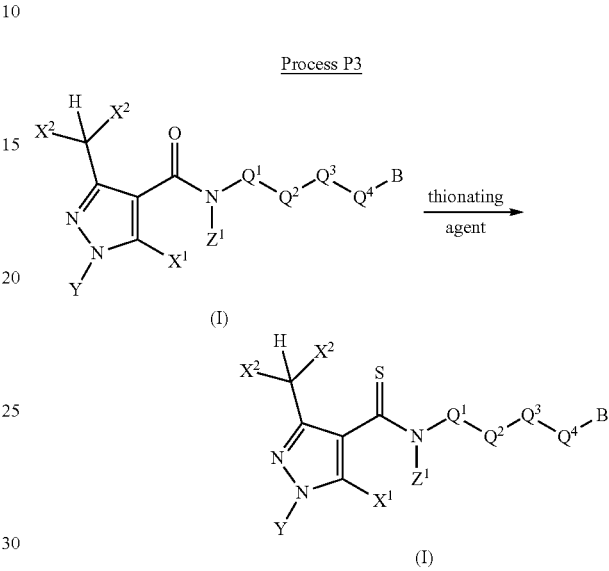

Process P3 wherein $X^1$, $X^2$, Y, $Z^1$, $Q^1$, $Q^2$, $Q^3$, $Q^4$ and B are as herein-defined, in the optional presence of a catalytic or stoechiometric or more, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methyl-piperidine.

Process P3 according to the invention is performed in the presence of a thionating agent.

Starting amide derivatives of formula (I) can be prepared according to processes P1.

Suitable thionating agents for carrying out process P3 according to the invention can be sulphur (S), sulfhydric acid ($H_2S$), sodium sulfide ($Na_2S$), sodium hydrosulfide (NaHS), boron trisulfide ($B_2S_3$), bis(diethylaluminium) sulfide ($(AlEt_2)_2S$), ammonium sulfide ($(NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in Journal of the Chemical Society, Perkin 1 (2001), 358.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the cropsand that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyolsand derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-

3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451) and (2.29) N-[9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, like for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-48-7), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-3), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, like for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, like for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-5), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.46) pyrroInitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c'] dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl] pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl] propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-

07-6) (WO 2007014290), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, like for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320) and (16.22) N-[2-(4-{[3-(4-chlorophenyl)prop-2-yn-1-yl]oxy}-3-methoxyphenyl)ethyl]-N2-(methylsulfonyl)valinamide (220706-93-4).

All named mixing partners of the classes (1) to (16) can, if their functional groups enable this, optionally form salts with suitable bases or acids.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbeffiferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767/61; 5,731,180; 5,304,732; 4,761/73; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus*

*thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyl-transferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549
  b) Plants, such as cotton plants, containing an altered form of rsw2 or rsw3 homologous nucleic acids as described in WO 2004/053219
  c) Plants, such as cotton plants, with increased expression of sucrose phosphate synthase as described in WO 01/17333
  d) Plants, such as cotton plants, with increased expression of sucrose synthase as described in WO 02/45485
  e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
  f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
  b) Plants such as oilseed rape plants, producing oil having a low linolenic acid content as described in U.S. Pat. No. 6,270,828, U.S. Pat. No. 6,169,190, or U.S. Pat. No. 5,965,755
  c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068,313 and WO10/006,732.

Particularly useful transgenic plants which may be treated according to the invention are plants containing transformation events, or combination of transformation events, that are the subject of petitions for nonregulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.
  Extension of Petition: reference to a previous petition for which an extension is requested.
  Institution: the name of the entity submitting the petition.
  Regulated article: the plant species concerned.
  Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.ag-bios.com/dbase.php).

Further particularly transgenic plants include plants containing a transgene in an agronomically neutral or beneficial position as described in any of the patent publications listed in Table C.

TABLE A

| Trait | Reference | |
|---|---|---|
| Water use efficiency | WO 2000/073475 | |
| Nitrogen use efficiency | WO 1995/009911 | WO 2007/076115 |
| | WO 1997/030163 | WO 2005/103270 |
| | WO 2007/092704 | WO 2002/002776 |

TABLE A-continued

| Trait | Reference | |
|---|---|---|
| Improved photosynthesis | WO 2008/056915 | WO 2004/101751 |
| Nematode resistance | WO 1995/020669 | WO 2003/033651 |
| | WO 2001/051627 | WO 1999/060141 |
| | WO 2008/139334 | WO 1998/012335 |
| | WO 2008/095972 | WO 1996/030517 |
| | WO 2006/085966 | WO 1993/018170 |
| Reduced pod dehiscence | WO 2006/009649 | WO 1997/013865 |
| | WO 2004/113542 | WO 1996/030529 |
| | WO 1999/015680 | WO 1994/023043 |
| | WO 1999/000502 | |
| Aphid resistance | WO 2006/125065 | WO 2008/067043 |
| | WO 1997/046080 | WO 2004/072109 |
| Sclerotinia resistance | WO 2006/135717 | WO 2005/000007 |
| | WO 2006/055851 | WO 2002/099385 |
| | WO 2005/090578 | WO 2002/061043 |
| Botrytis resistance | WO 2006/046861 | WO 2002/085105 |
| Bremia resistance | US 20070022496 | WO 2004/049786 |
| | WO 2000/063432 | |
| Erwinia resistance | WO 2004/049786 | |
| Closterovirus resistance | WO 2007/073167 | WO 2002/022836 |
| | WO 2007/053015 | |
| Stress tolerance (including drought tolerance) | WO 2010/019838 | WO 2008/002480 |
| | WO 2009/049110 | WO 2005/033318 |
| Tobamovirus resistance | WO 2006/038794 | |

TABLE B

Petitions of Nonregulated Status Granted or Pending by APHIS as of Mar. 31, 2010

Petitions for Nonregulated Status Pending

Applicant Documents

| Petition | Extension of Petition Number *** | Institution | Regulated Article | Transgenic Phenotype | Transformation Event or Line |
|---|---|---|---|---|---|
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-87705-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | Eucalyptus | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-52401-4 and IFD-52901-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-305423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |

TABLE B-continued

Petitions of Nonregulated Status Granted or Pending by APHIS as of Mar. 31, 2010

Petitions for Nonregulated Status Granted

Applicant Documents

| Petition | Extension of Petition Number *** | Institution | Regulated Article | Transgenic Phenotype | Transformation Event or Line |
|---|---|---|---|---|---|
| 07-152-01p | | Pioneer | Corn | glyphosate & Imidazolinone tolerant | DP-098140-6 |
| 04-337-01p | | University of Florida | Papaya | Papaya Ringspot Virus Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |
| 06-271-01p | | Pioneer | Soybean | Glyphosate & acetolactate synthase tolerant | 356043 (DP-356043-5) |
| 06-234-01p | 98-329-01p | Bayer CropScience | Rice | Phosphinothricin tolerant | LLRICE601 |
| 06-178-01p | | Monsanto | Soybean | Glyphosate tolerant | MON 89788 |
| 04-362-01p | | Syngenta | Corn | Corn Rootworm Protected | MIR604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |
| 01-324-01p | 98-216-01p | Monsanto | Rapeseed | Glyphosate tolerant | RT200 |
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |

TABLE B-continued

Petitions of Nonregulated Status Granted or Pending by APHIS as of Mar. 31, 2010

| | | | | | |
|---|---|---|---|---|---|
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Male sterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704-12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |
| 95-338-01p | | Monsanto | Potato | CPB resistant | SBT02-5 & -7, ATBT04-6 & -27, -30, -31, -36 |
| 95-324-01p | | Agritope | Tomato | Fruit ripening altered | 35 1 N |
| 95-256-01p | | Du Pont | Cotton | Sulfonylurea tolerant | 19-51a |
| 95-228-01p | | Plant Genetic Systems | Corn | Male sterile | MS3 |
| 95-195-01p | | Northrup King | Corn | European Corn Borer resistant | Bt11 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86- 18 & 23 |
| 93-258-01p | | Monsanto | Soybean | Glyphosate tolerant | 40-3-2 |
| 93-196-01p | | Calgene | Cotton | Bromoxynil tolerant | BXN |

TABLE B-continued

Petitions of Nonregulated Status Granted or Pending by APHIS as of Mar. 31, 2010

| 92-204-01p | Upjohn | Squash | WMV2 & ZYMV resistant | ZW-20 |
| 92-196-01p | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV—cucumber mosaic virus;
CPB—colorado potato beetle;
PLRV—potato leafroll virus;
PRSV—papaya ringspot virus;
PVY—potato virus Y;
WMV2—watermelon mosaic virus 2
ZYMV—zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
| --- | --- | --- | --- |
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |
| Corn | MON87460 | Drought tolerance | WO 2009/111263 |
| Corn | DP-098140-6 | Glyphosate tolerance/ALS inhibitor tolerance | WO 2008/112019 |
| Wheat | Event 1 | Fusarium resistance (trichothecene 3-O-acetyltransferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO 2008/122406 |
| Cotton | Cot202 | Insect resistance (VIP3) | US 2007-067868 |
| Cotton | LLcotton25 | Glufosinate resistance | WO 2007/017186 |
| Cotton | EE-GH5 | Insect resistance (Cry1Ab) | WO 2008/122406 |
| Cotton | event 281-24-236 | Insect resistance (Cry1F) | WO 2005/103266 |
| Cotton | Cot102 | Insect resistance (Vip3A) | US 2006-130175 |
| Cotton | MON 15985 | Insect resistance (Cry1A/Cry2Ab) | US 2004-250317 |

TABLE C-continued

| Plant species | Event | Trait | Patent reference |
|---|---|---|---|
| Bent Grass | Asr-368 | Glyphosate tolerance | US 2006-162007 |
| Brinjal | EE-1 | Insect resistance (Cry1Ac) | WO 2007/091277 |

Among the diseases of plants or crops that can be controlled by the method according to the invention, mention can be made of:

Powdery mildew diseases such as:
Blumeria diseases, caused for example by Blumeria graminis;
Podosphaera diseases, caused for example by Podosphaera leucotricha;
Sphaerotheca diseases, caused for example by Sphaerotheca fuliginea;
Uncinula diseases, caused for example by Uncinula necator;
Rust diseases such as:
Gymnosporangium diseases, caused for example by Gymnosporangium sabinae;
Hemileia diseases, caused for example by Hemileia vastatrix;
Phakopsora diseases, caused for example by Phakopsora pachyrhizi or Phakopsora meibomiae;
Puccinia diseases, caused for example by Puccinia recondite, Puccinia graminis or Puccinia striiformis;
Uromyces diseases, caused for example by Uromyces appendiculatus;
Oomycete diseases such as:
Albugo diseases caused for example by Albugo candida;
Bremia diseases, caused for example by Bremia lactucae;
Peronospora diseases, caused for example by Peronospora pisi or P. brassicae;
Phytophthora diseases, caused for example by Phytophthora infestans;
Plasmopara diseases, caused for example by Plasmopara viticola;
Pseudoperonospora diseases, caused for example by Pseudoperonospora humuli or Pseudoperonospora cubensis;
Pythium diseases, caused for example by Pythium ultimum;
Leafspot, leaf blotch and leaf blight diseases such as:
Alternaria diseases, caused for example by Alternaria solani;
Cercospora diseases, caused for example by Cercospora beticola;
Cladiosporium diseases, caused for example by Cladiosporium cucumerinum;
Cochliobolus diseases, caused for example by Cochliobolus sativus (Conidiaform: Drechslera, Syn: Helminthosporium) or Cochliobolus miyabeanus;
Colletotrichum diseases, caused for example by Colletotrichum lindemuthanium;
Cycloconium diseases, caused for example by Cycloconium oleaginum;
Diaporthe diseases, caused for example by Diaporthe citri;
Elsinoe diseases, caused for example by Elsinoe fawcettii;
Gloeosporium diseases, caused for example by Gloeosporium laeticolor;
Glomerella diseases, caused for example by Glomerella cingulata;
Guignardia diseases, caused for example by Guignardia bidwelli;
Leptosphaeria diseases, caused for example by Leptosphaeria maculans; Leptosphaeria nodorum;
Magnaporthe diseases, caused for example by Magnaporthe grisea;
Mycosphaerella diseases, caused for example by Mycosphaerella graminicola; Mycosphaerella arachidicola; Mycosphaerella fijiensis;
Phaeosphaeria diseases, caused for example by Phaeosphaeria nodorum;
Pyrenophora diseases, caused for example by Pyrenophora teres, or Pyrenophora tritici repentis;
Ramularia diseases, caused for example by Ramularia collo-cygni, or Ramularia areola;
Rhynchosporium diseases, caused for example by Rhynchosporium secalis;
Septoria diseases, caused for example by Septoria apii or Septoria lycopercisi;
Typhula diseases, caused for example by Typhula incarnate;
Venturia diseases, caused for example by Venturia inaequalis;
Root, Sheath and stem diseases such as:
Corticium diseases, caused for example by Corticium graminearum;
Fusarium diseases, caused for example by Fusarium oxysporum;
Gaeumannomyces diseases, caused for example by Gaeumannomyces graminis;
Rhizoctonia diseases, caused for example by Rhizoctonia solani;
Sarocladium diseases caused for example by Sarocladium oryzae;
Sclerotium diseases caused for example by Sclerotium oryzae;
Tapesia diseases, caused for example by Tapesia acuformis;
Thielaviopsis diseases, caused for example by Thielaviopsis basicola;
Ear and panicle diseases such as:
Alternaria diseases, caused for example by Alternaria spp.;
Aspergillus diseases, caused for example by Aspergillus flavus;
Cladosporium diseases, caused for example by Cladosporium spp.;
Claviceps diseases, caused for example by Claviceps purpurea;
Fusarium diseases, caused for example by Fusarium culmorum;
Gibberella diseases, caused for example by Gibberella zeae;
Monographella diseases, caused for example by Monographella nivalis;
Smut and bunt diseases such as:
Sphacelotheca diseases, caused for example by Sphacelotheca reiliana;
Tilletia diseases, caused for example by Tilletia caries;

*Urocystis* diseases, caused for example by *Urocystis occulta;*
*Ustilago* diseases, caused for example by *Ustilago nuda;*
Fruit rot and mould diseases such as:
*Aspergillus* diseases, caused for example by *Aspergillus flavus;*
*Botrytis* diseases, caused for example by *Botrytis cinerea;*
*Penicillium* diseases, caused for example by *Penicillium expansum;*
*Rhizopus* diseases caused by example by *Rhizopus stolonifer*
*Sclerotinia* diseases, caused for example by *Sclerotinia sclerotiorum;*
*Verticilium* diseases, caused for example by *Verticilium alboatrum;*
Seed and soilborne decay, mould, wilt, rot and damping-off diseases:
*Alternaria* diseases, caused for example by *Alternaria brassicicola*
*Aphanomyces* diseases, caused for example by *Aphanomyces euteiches*
*Ascochyta* diseases, caused for example by *Ascochyta lentis*
*Aspergillus* diseases, caused for example by *Aspergillus flavus*
*Cladosporium* diseases, caused for example by *Cladosporium herbarum*
*Cochliobolus* diseases, caused for example by *Cochliobolus sativus*
(Conidiaform: *Drechslera, Bipolaris* Syn: *Helminthosporium*);
*Colletotrichum* diseases, caused for example by *Colletotrichum coccodes;*
*Fusarium* diseases, caused for example by *Fusarium culmorum;*
*Gibberella* diseases, caused for example by *Gibberella zeae;*
*Macrophomina* diseases, caused for example by *Macrophomina phaseolina*
*Monographella* diseases, caused for example by *Monographella nivalis;*
*Penicillium* diseases, caused for example by *Penicillium expansum*
*Phoma* diseases, caused for example by *Phoma lingam*
*Phomopsis* diseases, caused for example by *Phomopsis sojae;*
*Phytophthora* diseases, caused for example by *Phytophthora cactorum;*
*Pyrenophora* diseases, caused for example by *Pyrenophora graminea*
*Pyricularia* diseases, caused for example by *Pyricularia oryzae;*
*Pythium* diseases, caused for example by *Pythium ultimum;*
*Rhizoctonia* diseases, caused for example by *Rhizoctonia solani;*
*Rhizopus* diseases, caused for example by *Rhizopus oryzae*
*Sclerotium* diseases, caused for example by *Sclerotium rolfsii;*
*Septoria* diseases, caused for example by *Septoria nodorum;*
*Typhula* diseases, caused for example by *Typhula incarnata;*
*Verticillium* diseases, caused for example by *Verticillium dahliae;*
Canker, broom and dieback diseases such as:
*Nectria* diseases, caused for example by *Nectria gaffigena;*

Blight diseases such as:
*Monilinia* diseases, caused for example by *Monilinia taxa;*
Leaf blister or leaf curl diseases such as:
*Exobasidium* diseases caused for example by *Exobasidium vexans*
*Taphrina* diseases, caused for example by *Taphrina deformans;*
Decline diseases of wooden plants such as:
Esca diseases, caused for example by *Phaemoniella clamydospora;*
*Eutypa* dyeback, caused for example by *Eutypa late;*
*Ganoderma* diseases caused for example by *Ganoderma boninense;*
*Rigidoporus* diseases caused for example by *Rigidoporus lignosus*
Diseases of Flowers and Seeds such as
*Botrytis* diseases caused for example by *Botrytis cinerea;*
Diseases of Tubers such as
*Rhizoctonia* diseases caused for example by *Rhizoctonia solani;*
*Helminthosporium* diseases caused for example by *Helminthosporium solani;*
Club root diseases such as
*Plasmodiophora* diseases, cause for example by *Plamodiophora brassicae.*
Diseases caused by Bacterial Organisms such as
*Xanthomonas* species for example *Xanthomonas campestris* pv. *oryzae;*
*Pseudomonas* species for example *Pseudomonas syringae* pv. *lachrymans;*
*Erwinia* species for example *Erwinia amylovora.*

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus.*

The various aspects of the invention will now be illustrated with reference to the following table of compound examples and the following preparation or efficacy examples.

Table 1 illustrates in a non-limiting manner examples of compounds of formula (I) according to the invention:

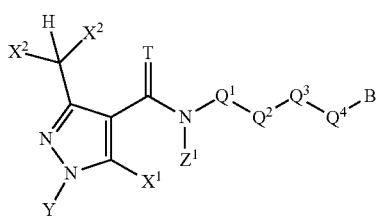

(I)

In table 1, unless otherwise specified, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

TABLE 1

| Example | X1 | X2 | Y | T | Z1 | Q1 | Q2 | Q3 | Q4 | B | logP | Mass (M + H) |
|---|---|---|---|---|---|---|---|---|---|---|---|---|
| 1 | F | F | Me | O | isopropyl | CH2 | C=O | NH | — | phenyl | 2.25 | 369 |
| 2 | Cl | F | Me | O | isopropyl | CH2 | C=O | NH | — | phenyl | 2.43 | 385 |
| 3 | F | F | Me | O | H | cyclopentyl-1,1-diyl | C=O | NH | — | phenyl | 2.46 | 381 |
| 4 | Cl | F | Me | O | H | cyclopentyl-1,1-diyl | C=O | NH | — | phenyl | 2.62 | 397 |
| 5 | Cl | F | Me | O | methyl | CH2 | CH2 | CH2 | — | phenyl | 2.82 | 342 |
| 6 | F | F | Me | O | methyl | CH2 | CH2 | CH2 | — | phenyl | 2.73 | 326 |
| 7 | Cl | F | Me | O | propyl | CH2 | CH2 | O | — | phenyl | 3.21 | 372 |
| 8 | F | F | Me | O | propyl | CH2 | CH2 | O | — | phenyl | 3.06 | 356 |
| 9 | F | F | Me | O | cyclopropyl | CH(Me) | C(Me)2 | CH2 | — | phenyl | 4.06 | 394 |
| 10 | Cl | F | Me | O | cyclopropyl | CH(Me) | C(Me)2 | CH2 | — | phenyl | 4.27 | 410 |
| 11 | Cl | F | Me | O | H | CH(Me) | CH2 | CH2 | — | phenyl | 3.04 | 342 |
| 12 | F | F | Me | O | H | CH(Me) | CH2 | CH2 | — | phenyl | 2.88 | 326 |
| 13 | F | F | Me | O | H | CH(Me) | CH2 | O | — | phenyl | 2.66 | 328 |
| 14 | Cl | F | Me | O | H | CH(Me) | CH2 | O | — | phenyl | 2.84 | 344 |
| 15 | Cl | F | Me | O | methyl | CH(Me) | CH2 | O | — | phenyl | 2.78 | 358 |
| 16 | F | F | Me | O | methyl | CH(Me) | CH2 | O | — | phenyl | 2.62 | 342 |
| 17 | F | F | Me | O | H | CH(c-Pr) | CH2 | NMe | — | phenyl | 3.02 | 367 |
| 18 | Cl | F | Me | O | H | CH(c-Pr) | CH2 | NMe | — | phenyl | 3.31 | 383 |
| 19 | F | F | Me | O | H | CH(c-Pr) | CH2 | O | — | phenyl | 3.06 | 354 |
| 20 | Cl | F | Me | O | H | CH(c-Pr) | CH2 | O | — | phenyl | 3.25 | 370 |
| 21 | F | F | Me | O | methyl | CH(c-Pr) | CH2 | O | — | phenyl | 3.08 | 368 |
| 22 | F | F | Me | O | H | CH(c-Pr) | CH2 | S | — | phenyl | 3.25 | 370 |
| 23 | Cl | F | Me | O | H | CH(c-Pr) | CH2 | S | — | phenyl | 3.44 | 386 |
| 24 | F | F | Me | O | H | C(Me)2 | C=O | NH | — | phenyl | 2.10 | 355 |
| 25 | Cl | F | Me | O | H | C(Me)2 | C=O | NH | — | phenyl | 2.27 | 371 |
| 26 | Cl | F | Me | O | H | CH2 | CH2 | O | — | biphenyl-4-yl | 3.60 | 406 |
| 27 | F | F | Me | O | H | CH2 | CH2 | O | — | biphenyl-4-yl | 3.44 | 390 |
| 28 | Cl | F | Me | O | cyclopropyl | CH2 | CH2 | O | — | biphenyl-4-yl | 4.03 | 446 |
| 29 | F | F | Me | O | cyclopropyl | CH2 | CH2 | O | — | biphenyl-4-yl | 3.90 | 430 |
| 30 | F | F | Me | O | propyl | CH(Me) | CH2 | O | — | biphenyl-2-yl | 4.32 | 446 |
| 31 | Cl | F | Me | O | propyl | CH(Me) | CH2 | O | — | biphenyl-2-yl | 4.51 | 462 |
| 32 | Cl | F | Me | O | H | CH2 | CH(CF3) | NMe | — | 4-phenoxyphenyl | 4.27 | 503 |
| 33 | F | F | Me | O | H | CH2 | CH(CF3) | NMe | — | 4-phenoxyphenyl | 4.16 | 487 |
| 34 | F | F | Me | O | H | CH2 | CH2 | O | — | 4-phenoxyphenyl | 3.42 | 406 |
| 35 | Cl | F | Me | O | H | CH2 | CH2 | O | — | 4-phenoxyphenyl | 3.55 | 422 |
| 36 | F | F | Me | O | H | CH(Me) | CH2 | CH2 | — | 4-methylpyridin-2-yl | 1.96 | 343 |
| 37 | Cl | F | Me | O | H | CH(Me) | CH2 | O | — | 4-methylpyridin-2-yl | 2.13 | 359 |
| 38 | F | F | Me | O | ethyl | CH(Me) | CH2 | O | — | 4-methylphenyl | 3.27 | 370 |
| 39 | Cl | F | Me | O | ethyl | CH(Me) | CH2 | O | — | 4-methylphenyl | 3.48 | 386 |
| 40 | F | F | Me | O | methyl | CH(c-Pr) | CH2 | S | — | 4-methylphenyl | 3.64 | 398 |
| 41 | Cl | F | Me | O | methyl | CH(c-Pr) | CH2 | S | — | 4-methylphenyl | 3.85 | 414 |
| 42 | F | F | Me | O | H | CH(Et) | CH2 | CH2 | — | 4-methoxypyridin-2-yl | 1.70 | 373 |
| 43 | Cl | F | Me | O | H | CH(Et) | CH2 | O | — | 4-methoxypyridin-2-yl | 1.86 | 389 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 44 | F | F | Me | O | H | #―▽―* (cyclopropylidene) | CH2 | O | — | 4-chlorophenyl | 3.00 | 374 |
| 45 | Cl | F | Me | O | H | #―▽―* (cyclopropylidene) | CH2 | O | — | 4-chlorophenyl | 3.19 | 390 |
| 46 | F | F | Me | O | H | CH2 | CH(CF3) | S | — | 4-chlorophenyl | 3.73 | 432 |
| 47 | Cl | F | Me | O | H | CH2 | CH(CF3) | S | — | 4-chlorophenyl | 3.89 | 448 |
| 48 | F | F | Me | O | H | CH2 | CH2 | O | — | 4-chlorophenyl | 2.78 | 348 |
| 49 | Cl | F | Me | O | H | CH2 | CH2 | O | — | 4-chlorophenyl | 2.96 | 364 |
| 50 | F | F | Me | O | cyclobutyl | CH2 | CH2 | O | — | 4-chlorophenyl | 3.78 | 402 |
| 51 | Cl | F | Me | O | cyclopentyl | CH2 | CH2 | O | — | 4-chlorophenyl | 4.32 | 432 |
| 52 | Cl | F | Me | O | cyclobutyl | CH2 | CH2 | O | — | 4-chlorophenyl | 3.99 | 418 |
| 53 | Cl | F | Me | O | isopropyl | CH2 | CH2 | O | — | 4-chlorophenyl | 3.78 | 406 |
| 54 | Cl | F | Me | O | propyl | CH2 | CH2 | O | — | 4-chlorophenyl | 3.67 | 406 |
| 55 | F | F | Me | O | cyclopentyl | CH2 | CH2 | O | — | 4-chlorophenyl | 4.13 | 416 |
| 56 | F | F | Me | O | isopropyl | CH2 | CH2 | O | — | 4-chlorophenyl | 3.62 | 390 |
| 57 | F | F | Me | O | propyl | CH2 | CH2 | O | — | 4-chlorophenyl | 3.53 | 390 |
| 58 | F | F | Me | O | H | CH2 | CH2 | SO2 | — | 4-chlorophenyl | 2.10 | 396 |
| 59 | Cl | F | Me | O | H | CH2 | CH2 | SO2 | — | 4-chlorophenyl | 2.30 | 412 |
| 60 | F | F | Me | O | H | CH(t-Bu) | CH2 | CH2 | — | 4-chlorophenyl | 4.24 | 402 |
| 61 | Cl | F | Me | O | H | CH(t-Bu) | CH2 | CH2 | — | 4-chlorophenyl | 4.41 | 418 |
| 62 | Cl | F | Me | O | H | CH(iPr) | CH2 | CH2 | — | 4-chlorophenyl | 4.11 | 404 |
| 63 | F | F | Me | O | H | CH(iPr) | CH2 | CH2 | — | 4-chlorophenyl | 3.94 | 388 |
| 64 | Cl | F | Me | O | H | CH(Me) | CH2 | CH2 | — | 4,6-dimethylpyridin-2-yl | 1.81 | 373 |
| 65 | F | F | Me | O | H | CH(Me) | CH2 | CH2 | — | 4,6-dimethylpyridin-2-yl | 1.60 | 357 |
| 66 | F | F | Me | O | H | CH(Et) | CH2 | CH2 | — | 4,6-dimethylpyridin-2-yl | 1.93 | 371 |
| 67 | Cl | F | Me | O | H | CH(Et) | CH2 | O | — | 4,6-dimethylpyridin-2-yl | 2.14 | 387 |
| 68 | F | F | Me | O | H | CH2 | CH2 | O | — | 4-(trifluoromethyl)phenyl | 3.04 | 382 |
| 69 | Cl | F | Me | O | H | CH2 | CH2 | O | — | 4-(trifluoromethyl)phenyl | 3.17 | 398 |
| 70 | Cl | F | Me | O | H | CH(Me) | CH2 | CH2 | — | 4-(trifluoromethyl)phenyl | 3.63 | 410 |
| 71 | F | F | Me | O | H | CH(Me) | CH2 | CH2 | — | 4-(trifluoromethyl)phenyl | 3.46 | 394 |
| 72 | Cl | F | Me | O | propyl | CH2 | CH2 | O | — | 4-(ethoxycarbonyl)phenyl | 3.44 | 444 |
| 73 | F | F | Me | O | propyl | CH2 | CH2 | O | — | 4-(ethoxycarbonyl)phenyl | 3.31 | 428 |
| 74 | F | F | Me | O | H | CH2 | CH2 | O | — | 3-phenoxyphenyl | 3.41 | 406 |
| 75 | Cl | F | Me | O | H | CH2 | CH2 | O | — | 3-phenoxyphenyl | 3.60 | 422 |
| 76 | Cl | F | Me | O | H | CH(Me) | CH2 | CH2 | — | 3-methylthiophen-2-yl | 3.17 | 362 |
| 77 | F | F | Me | O | H | CH(Me) | CH2 | CH2 | — | 3-methylthiophen-2-yl | 3.02 | 346 |
| 78 | F | F | Me | O | H | CH(Et) | CH2 | CH2 | — | 3-methylthiophen-2-yl | 3.48 | 376 |
| 79 | F | F | Me | O | H | CH(Et) | CH2 | CH2 | — | 3-methylthiophen-2-yl | 3.31 | 360 |
| 80 | Cl | F | Me | O | H | #―(3-methylcyclohexane-1,2-diyl)―* | CH2 | — | — | 3-chlorophenyl | 4.51 | 430 |
| 81 | Cl | F | Me | O | methyl | CH2 | CH2 | NMe | — | 3-chlorophenyl | 3.19 | 391 |
| 82 | F | F | Me | O | methyl | CH2 | CH2 | NMe | — | 3-chlorophenyl | 3.02 | 375 |
| 83 | Cl | F | Me | O | H | C(Me)2 | CH2 | CH2 | — | 3-chlorophenyl | 4.01 | 390 |
| 84 | F | F | Me | O | H | C(Me)2 | CH2 | CH2 | — | 3-chlorophenyl | 3.83 | 374 |
| 85 | Cl | F | Me | O | cyclopropyl | CH(Me) | CH2 | CH2 | — | 3-chloro-5-(trifluoromethyl)pyridin-2-yl | 4.11 | 485 |
| 86 | F | F | Me | O | cyclopropyl | CH(Me) | CH2 | CH2 | — | 3-chloro-5-(trifluoromethyl)pyridin-2-yl | 3.92 | 469 |
| 87 | F | F | Me | O | methyl | CH(Me) | CH2 | CH2 | — | 3-chloro-5-(trifluoromethyl)pyridin-2-yl | 3.29 | 443 |
| 88 | Cl | F | Me | O | methyl | CH(Me) | CH2 | CH2 | — | 3-chloro-5-(trifluoromethyl)pyridin-2-yl | 3.45 | 459 |
| 89 | F | F | Me | O | H | CH(Et) | CH2 | CH2 | — | 3-bromothiophen-2-yl | 3.46 | 424 |
| 90 | Cl | F | Me | O | H | CH(Et) | CH2 | CH2 | — | 3-bromothiophen-2-yl | 3.63 | 440 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 91 | F | F | Me | O | cyclopropyl | CH2 | CH2 | CH2 | — | 1-benzofuran-2-yl | 3.52 | 392 |
| 92 | F | F | Me | O | H | CH2 | CH2 | CH2 | — | 1-benzofuran-2-yl | 2.90 | 352 |
| 93 | F | F | Me | O | methyl | CH2 | CH2 | CH2 | — | 1-benzofuran-2-yl | 3.00 | 366 |
| 94 | F | F | Me | O | cyclopropyl | CH2 | CH2 | CH2 | — | 1-benzothiophen-2-yl | 3.79 | 408 |
| 95 | F | F | Me | O | H | CH2 | CH2 | CH2 | — | 1-benzothiophen-2-yl | 3.17 | 368 |
| 96 | F | F | Me | O | methyl | CH2 | CH2 | CH2 | — | 1-benzothiophen-2-yl | 3.25 | 382 |
| 97 | F | F | Me | O | H | CH2 | CH2 | CH2 | — | 2,3-dihydro-1-benzofuran-2-yl | 2.69 | 354 |
| 98 | F | F | Me | O | cyclopropyl | CH2 | CH2 | CH2 | — | 2,3-dihydrofuran-2-yl | 1.45 | 344 |
| 99 | F | F | Me | O | cyclopropyl | CH2 | CH2 | CH2 | — | 2-furyl | 2.75 | 342 |
| 100 | F | F | Me | O | H | CH2 | CH2 | CH2 | — | 2-furyl | 2.17 | 302 |
| 101 | F | F | Me | O | methyl | CH2 | CH2 | CH2 | — | 2-furyl | 2.25 | 316 |
| 102 | F | F | Me | O | cyclopropyl | CH2 | CH2 | CH2 | — | 2-thienyl | 3.04 | 358 |
| 103 | Cl | F | Me | O | cyclopropyl | CH(Me) | CH2 | CH2 | — | 2-thienyl | 3.57 | 388 |
| 104 | F | F | Me | O | methyl | CH2 | CH2 | CH2 | — | 2-thienyl | 2.52 | 332 |
| 105 | F | F | Me | O | cyclopropyl | CH2 | CH2 | CH2 | — | 3-methyl-2-thienyl | 3.33 | 372 |
| 106 | F | F | Me | O | cyclopropyl | CH2 | CH2 | CH2 | — | 5-methyl-1-benzothiophen-2-yl | 4.21 | 422 |
| 107 | F | F | Me | O | cyclopropyl | CH2 | CH2 | CH(Me) | — | 5-methyl-2-furyl | 3.41 | 370 |
| 108 | Cl | F | Me | O | cyclopropyl | CH2 | CH2 | CH(Me) | — | 5-methyl-2-furyl | 3.56 | 386 |
| 109 | F | F | Me | O | methyl | CH2 | CH2 | CH(Me) | — | 5-methyl-2-furyl | 2.88 | 344 |
| 110 | Cl | F | Me | O | methyl | CH2 | CH2 | CH(Me) | — | 5-methyl-2-furyl | 3.02 | 360 |
| 111 | Cl | F | Me | O | methoxy | CH2 | CH2 | CH(Me) | — | 5-methyl-2-furyl | 3.29 | 376 |
| 112 | F | F | Me | O | methoxy | CH2 | CH2 | CH(Me) | — | 5-methyl-2-furyl | 3.23 | 360 |
| 113 | F | F | Me | O | cyclopropyl | CH2 | CH2 | CH2 | — | 5-methyl-2-thienyl | 3.44 | 372 |
| 114 | F | F | Me | O | cyclopropyl | CH2 | CH2 | CH2 | — | tetrahydrofuran-2-yl | 2.21 | 346 |
| 115 | Cl | F | Me | O | H | CH2 | CH(Me) | CH2 | — | 3,5-dichlorophenyl | 4.04 | 410 |
| 116 | F | F | Me | O | H | CH2 | CH(Me) | CH2 | — | 3,5-dichlorophenyl | 3.83 | 394 |
| 117 | F | F | Me | O | H | CH2 | CH2 | O | — | 3,5-dichlorophenyl | 3.35 | 382 |
| 118 | Cl | F | Me | O | H | CH2 | CH2 | O | — | 3,5-dichlorophenyl | 3.55 | 398 |
| 119 | Cl | F | Me | O | H | CH(Me) | CH2 | CH2 | — | 3,5-dichlorophenyl | 4.01 | 410 |
| 120 | F | F | Me | O | H | CH(Me) | CH2 | CH2 | — | 3,5-dichlorophenyl | 3.83 | 394 |
| 121 | F | F | Me | O | H | CH(Me) | CH2 | O | — | 3,5-dichlorophenyl | 3.72 | 396 |
| 122 | Cl | F | Me | O | H | CH(Me) | CH2 | O | — | 3,5-dichlorophenyl | 3.92 | 412 |
| 123 | F | F | Me | O | H | CH(Et) | CH2 | O | — | 3,5-dichlorophenyl | 4.04 | 410 |
| 124 | Cl | F | Me | O | H | CH(Et) | CH2 | O | — | 3,5-dichlorophenyl | 4.23 | 426 |
| 125 | Cl | F | Me | O | H | C(Me)2 | CH2 | CH2 | — | 3,5-dichlorophenyl | 4.64 | 424 |
| 126 | F | F | Me | O | H | C(Me)2 | CH2 | CH2 | — | 3,5-dichlorophenyl | 4.41 | 408 |
| 127 | Cl | F | Me | O | H | CH2 | CH(Me) | CH2 | — | 3,4-dichlorophenyl | 3.87 | 410 |
| 128 | F | F | Me | O | H | CH2 | CH(Me) | CH2 | — | 3,4-dichlorophenyl | 3.68 | 394 |
| 129 | F | F | Me | O | cyclopropyl | CH(Me) | CH2 | CH2 | — | 3,4-dichlorophenyl | 4.44 | 434 |
| 130 | Cl | F | Me | O | cyclopropyl | CH(Me) | CH2 | CH2 | — | 3,4-dichlorophenyl | 4.62 | 450 |
| 131 | Cl | F | Me | O | H | CH(Me) | CH2 | CH2 | — | 3,4-dichlorophenyl | 3.85 | 410 |
| 132 | F | F | Me | O | H | CH(Me) | CH2 | CH2 | — | 3,4-dichlorophenyl | 3.65 | 394 |
| 133 | Cl | F | Me | O | H | C(Me)2 | CH2 | CH2 | — | 3,4-dichlorophenyl | 4.44 | 424 |
| 134 | F | F | Me | O | H | C(Me)2 | CH2 | CH2 | — | 3,4-dichlorophenyl | 4.21 | 408 |
| 135 | Cl | F | Me | O | H | C(Me)2 | CH2 | CH2 | — | 3-(trifluoromethyl)phenyl | 4.11 | 424 |
| 136 | F | F | Me | O | H | C(Me)2 | CH2 | CH2 | — | 3-(trifluoromethyl)phenyl | 3.94 | 408 |
| 137 | F | F | Me | O | H | CH(c-Pr) | CH2 | O | — | 2-naphthyl | 3.74 | 404 |
| 138 | Cl | F | Me | O | H | CH(c-Pr) | CH2 | O | — | 2-naphthyl | 3.94 | 420 |
| 139 | F | F | Me | O | methyl | CH(c-Pr) | CH2 | O | — | 2-naphthyl | 3.76 | 418 |
| 140 | Cl | F | Me | O | methyl | CH(c-Pr) | CH2 | O | — | 2-naphthyl | 3.96 | 434 |
| 141 | Cl | F | Me | O | methyl | CH2 | CH2 | CH2 | — | 2-chlorophenyl | 3.17 | 376 |
| 142 | F | F | Me | O | methyl | CH2 | CH2 | CH2 | — | 2-chlorophenyl | 3.06 | 360 |
| 143 | Cl | F | Me | O | H | CH(Me) | CH2 | CH2 | — | 2-chlorophenyl | 3.41 | 376 |
| 144 | F | F | Me | O | H | CH(Me) | CH2 | CH2 | — | 2-chlorophenyl | 3.21 | 360 |
| 145 | F | F | Me | O | methyl | CH(c-Pr) | CH2 | O | — | 2-chlorophenyl | 3.44 | 402 |
| 146 | Cl | F | Me | O | methyl | CH(c-Pr) | CH2 | O | — | 2-chlorophenyl | 3.67 | 418 |
| 147 | Cl | F | Me | O | H | C(Me)2 | CH2 | CH2 | — | 2-chlorophenyl | 3.99 | 390 |
| 148 | F | F | Me | O | H | C(Me)2 | CH2 | CH2 | — | 2-chlorophenyl | 3.79 | 374 |
| 149 | Cl | F | Me | O | H | CH2 | CH(Me) | CH2 | — | 2,6-dimethylphenyl | 3.63 | 370 |
| 150 | F | F | Me | O | H | CH2 | CH(Me) | CH2 | — | 2,6-dimethylphenyl | 3.44 | 354 |
| 151 | F | F | Me | O | H | CH2 | CH2 | O | — | 2,6-dimethylphenyl | 2.88 | 342 |
| 152 | Cl | F | Me | O | H | CH2 | CH2 | O | — | 2,6-dimethylphenyl | 3.13 | 358 |
| 153 | Cl | F | Me | O | H | CH(Me) | CH2 | CH2 | — | 2,6-dimethylphenyl | 3.61 | 370 |
| 154 | F | F | Me | O | H | CH(Me) | CH2 | CH2 | — | 2,6-dimethylphenyl | 3.41 | 354 |
| 155 | F | F | Me | O | cyclopropyl | CH(Me) | CH2 | O | — | 2,6-dimethylphenyl | 3.94 | 396 |
| 156 | Cl | F | Me | O | cyclopropyl | CH(Me) | CH2 | O | — | 2,6-dimethylphenyl | 4.15 | 412 |
| 157 | F | F | Me | O | H | CH2 | CH(Me) | CH2 | — | 2,6-difluorophenyl | 3.02 | 362 |
| 158 | Cl | F | Me | O | H | CH2 | CH(Me) | CH2 | — | 2,6-difluorophenyl | 3.21 | 378 |
| 159 | F | F | Me | O | H | CH2 | CH2 | O | — | 2,6-difluorophenyl | 2.44 | 350 |
| 160 | Cl | F | Me | O | H | CH2 | CH2 | O | — | 2,6-difluorophenyl | 2.64 | 366 |
| 161 | Cl | F | Me | O | cyclopropyl | CH2 | CH2 | O | — | 2,6-dichlorophenyl | 3.69 | 438 |
| 162 | F | F | Me | O | cyclopropyl | CH2 | CH2 | O | — | 2,6-dichlorophenyl | 3.55 | 422 |
| 163 | F | F | Me | O | H | CH(Me) | CH2 | CH2 | — | 2,6-dichlorophenyl | 3.59 | 394 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 164 | Cl | F | Me | O | H | CH2 | CH(Me) | CH2 | — | 2,5-dichlorophenyl | 3.87 | 410 |
| 165 | F | F | Me | O | H | CH2 | CH(Me) | CH2 | — | 2,5-dichlorophenyl | 3.65 | 394 |
| 166 | F | F | Me | O | methyl | CH2 | CH2 | CH2 | — | 2,5-dichlorophenyl | 3.48 | 394 |
| 167 | Cl | F | Me | O | methyl | CH2 | CH2 | CH2 | — | 2,5-dichlorophenyl | 3.62 | 410 |
| 168 | F | F | Me | S | Me | CH2 | CH2 | CH2 | — | 2,5-dichlorophenyl | 4.11 | 410 |
| 169 | F | F | Me | O | H | CH2 | CH2 | O | — | 2,5-dichlorophenyl | 3.11 | 382 |
| 170 | Cl | F | Me | O | H | CH2 | CH2 | O | — | 2,5-dichlorophenyl | 3.31 | 398 |
| 171 | Cl | F | Me | O | H | CH(Me) | CH2 | CH2 | — | 2,5-dichlorophenyl | 3.87 | 410 |
| 172 | F | F | Me | O | H | CH(Me) | CH2 | CH2 | — | 2,5-dichlorophenyl | 3.68 | 394 |
| 173 | F | F | Me | O | H | CH(Me) | CH2 | O | — | 2,5-dichlorophenyl | 3.46 | 396 |
| 174 | Cl | F | Me | O | H | CH(Me) | CH2 | O | — | 2,5-dichlorophenyl | 3.69 | 412 |
| 175 | F | F | Me | O | H | CH(Et) | CH2 | O | — | 2,5-dichlorophenyl | 3.83 | 410 |
| 176 | Cl | F | Me | O | H | CH(Et) | CH2 | O | — | 2,5-dichlorophenyl | 4.01 | 426 |
| 177 | Cl | F | Me | O | H | C(Me)2 | CH2 | CH2 | — | 2,5-dichlorophenyl | 4.49 | 424 |
| 178 | F | F | Me | O | H | C(Me)2 | CH2 | CH2 | — | 2,5-dichlorophenyl | 4.26 | 408 |
| 179 | Cl | F | Me | O | H | CH2 | CH2 | CH2 | — | 2,4-dichlorophenyl | 3.68 | 396 |
| 180 | F | F | Me | O | H | CH2 | CH2 | CH2 | — | 2,4-dichlorophenyl | 3.46 | 380 |
| 181 | F | F | Me | O | cyclopropyl | C(Me)2 | C(Me)2 | CH2 | — | 2,4-dichlorophenyl | 5.14 | 462 |
| 182 | Cl | F | Me | O | cyclopropyl | CH(Me) | C(Me)2 | CH2 | — | 2,4-dichlorophenyl | 5.39 | 478 |
| 183 | Cl | F | Me | O | cyclopropyl | CH(Me) | CH2 | CH2 | — | 2,4-dichlorophenyl | 4.72 | 450 |
| 184 | F | F | Me | O | cyclopropyl | CH(Me) | CH2 | CH2 | — | 2,4-dichlorophenyl | 4.56 | 434 |
| 185 | Cl | F | Me | O | H | CH(Me) | CH2 | CH2 | — | 2,4-dichlorophenyl | 3.99 | 410 |
| 186 | F | F | Me | O | H | CH(Me) | CH2 | CH2 | — | 2,4-dichlorophenyl | 3.79 | 394 |
| 187 | F | F | Me | O | cyclopropyl | CH(Me) | CH2 | O | — | 2,4-dichlorophenyl | 4.16 | 436 |
| 188 | Cl | F | Me | O | cyclopropyl | CH(Me) | CH2 | O | — | 2,4-dichlorophenyl | 4.41 | 452 |
| 189 | F | F | Me | O | H | CH(Me) | CH2 | O | — | 2,4-dichlorophenyl | 3.58 | 396 |
| 190 | Cl | F | Me | O | H | CH(Me) | CH2 | O | — | 2,4-dichlorophenyl | 3.76 | 412 |
| 191 | F | F | Me | O | H | CH(Me) | CH2 | S | — | 2,4-dichlorophenyl | 3.76 | 412 |
| 192 | Cl | F | Me | O | H | CH(Me) | CH2 | S | — | 2,4-dichlorophenyl | 4.01 | 428 |
| 193 | F | F | Me | O | H | CH(c-Pr) | CH2 | O | — | 2,4-dichlorophenyl | 3.92 | 422 |
| 194 | Cl | F | Me | O | H | CH(c-Pr) | CH2 | O | — | 2,4-dichlorophenyl | 4.18 | 438 |
| 195 | Cl | F | Me | O | H | C(Me)2 | CH2 | CH2 | — | 2,4-dichlorophenyl | 4.61 | 424 |
| 196 | F | F | Me | O | H | C(Me)2 | CH2 | CH2 | — | 2,4-dichlorophenyl | 4.39 | 408 |
| 197 | F | F | Me | O | H | CH2 | C=O | NH | — | 2,4,6-trichlorophenyl | 2.39 | 429 |
| 198 | Cl | F | Me | O | H | CH2 | C=O | NH | — | 2,4,6-trichlorophenyl | 2.56 | 445 |
| 199 | Cl | F | Me | O | propyl | CH2 | C=O | NH | — | 2,4,6-trichlorophenyl | 3.11 | 487 |
| 200 | F | F | Me | O | propyl | CH2 | C=O | NH | — | 2,4,6-trichlorophenyl | 2.96 | 471 |
| 201 | Cl | F | Me | O | H | CH2 | CH2 | O | — | 2,4,6-trichlorophenyl | 3.80 | 432 |
| 202 | F | F | Me | O | H | CH2 | CH2 | O | — | 2,4,6-trichlorophenyl | 3.60 | 416 |
| 203 | F | F | Me | O | isopropyl | CH2 | CH2 | O | — | 2,4,6-trichlorophenyl | 4.51 | 458 |
| 204 | F | F | Me | O | propyl | CH2 | CH2 | O | — | 2,4,6-trichlorophenyl | 4.37 | 458 |
| 205 | Cl | F | Me | O | propyl | CH2 | CH2 | O | — | 2,4,6-trichlorophenyl | 4.56 | 474 |
| 206 | Cl | F | Me | O | cyclopentyl | CH2 | CH2 | O | — | 2,4,6-trichlorophenyl | 5.27 | 500 |
| 207 | Cl | F | Me | O | 3-oxetanyl | CH2 | CH2 | O | — | 2,4,6-trichlorophenyl | 3.55 | 488 |
| 208 | Cl | F | Me | O | isopropyl | CH2 | CH2 | O | — | 2,4,6-trichlorophenyl | 4.71 | 474 |
| 209 | F | F | Me | O | cyclopentyl | CH2 | CH2 | O | — | 2,4,6-trichlorophenyl | 5.08 | 484 |
| 210 | F | F | Me | O | 3-oxetanyl | CH2 | CH2 | O | — | 2,4,6-trichlorophenyl | 3.42 | 472 |
| 211 | Cl | F | Me | O | H | CH(Me) | CH2 | O | — | 2,4,6-trichlorophenyl | 4.20 | 446 |
| 212 | F | F | Me | O | H | CH(Me) | CH2 | O | — | 2,4,6-trichlorophenyl | 3.92 | 430 |
| 213 | F | F | Me | O | cyclopropyl | CH(Me) | CH2 | CH2 | — | 2,4,6-trichlorophenyl | 5.14 | 468 |
| 214 | Cl | F | Me | O | cyclopropyl | CH(Me) | CH2 | CH2 | — | 2,4,6-trichlorophenyl | 4.31 | 484 |
| 215 | F | F | Me | O | H | CH(Me) | CH2 | CH2 | — | 2,4,6-trichlorophenyl | 4.29 | 428 |
| 216 | Cl | F | Me | O | H | CH(Me) | CH2 | CH2 | — | 2,4,6-trichlorophenyl | 4.53 | 444 |
| 217 | F | F | Me | O | methoxy | CH(Me) | CH2 | CH2 | — | 2,4,6-trichlorophenyl | 4.77 | 458 |
| 218 | Cl | F | Me | O | methoxy | CH(Me) | CH2 | CH2 | — | 2,4,6-trichlorophenyl | 4.89 | 474 |
| 219 | F | F | Me | S | cyclopropyl | CH(Me) | CH2 | CH2 | — | 2,4,6-trichlorophenyl | 5.81 | 484 |
| 220 | Cl | F | Me | O | cyclopropyl | CH(Me) | CH2 | CH2 | — | 2-(trifluoromethyl)phenyl | 4.26 | 450 |
| 221 | F | F | Me | O | cyclopropyl | CH(Me) | CH2 | CH2 | — | 2-(trifluoromethyl)phenyl | 4.09 | 434 |
| 222 | F | F | Me | O | H | CH(Et) | CH2 | O | — | 1-naphthyl | 3.71 | 392 |
| 223 | Cl | F | Me | O | H | CH(Et) | CH2 | O | — | 1-naphthyl | 3.85 | 408 |
| 224 | Cl | F | Me | O | methyl | CH(c-Pr) | CH2 | S | CH2 | phenyl | 3.62 | 414 |
| 225 | F | F | Me | O | methyl | CH(c-Pr) | CH2 | S | CH2 | phenyl | 3.46 | 398 |
| 226 | F | F | Me | O | methyl | CH2 | C=O | O | CH2 | phenyl | 2.44 | 356 |
| 227 | F | F | Me | O | methyl | CH(i-Pr) | C=O | O | CH2 | phenyl | 3.35 | 398 |
| 228 | Cl | F | Me | O | methyl | CH2 | C=O | O | CH2 | phenyl | 2.57 | 372 |
| 229 | Cl | F | Me | O | methyl | CH(i-Pr) | C=O | O | CH2 | phenyl | 3.48 | 414 |
| 230 | F | F | Me | O | methyl | CH2 | CH2 | NMe | C=O | phenyl | 1.66 | 369 |
| 231 | Cl | F | Me | O | methyl | CH2 | CH2 | NMe | C=O | phenyl | 1.76 | 385 |
| 232 | F | F | Me | O | methyl | CH2 | CH2 | C=O | NH | 3,4-dichlorophenyl | 2.71 | 423 |
| 233 | Cl | F | Me | O | methyl | CH2 | CH2 | C=O | NH | 3,4-dichlorophenyl | 2.86 | 439 |
| 234 | Cl | F | Me | O | propyl | CH2 | CH2 | CH2 | O | 2,4,6-trimethylphenyl | 4.39 | 428 |
| 235 | F | F | Me | O | propyl | CH2 | CH2 | CH2 | O | 2,4,6-trimethylphenyl | 4.27 | 412 |
| 236 | F | F | Me | O | cyclopropyl | CH(Me) | CH2 | S | CH2 | 2-furyl | 3.11 | 388 |
| 237 | Cl | F | Me | O | cyclopropyl | CH(Me) | CH2 | S | CH2 | 2-furyl | 3.27 | 404 |
| 238 | F | F | Me | O | methyl | CH(Me) | CH2 | S | CH2 | 2-furyl | 2.49 | 362 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 239 | Cl | F | Me | O | methyl | CH(Me) | CH2 | S | CH2 | 2-furyl | 2.64 | 378 |
| 240 | F | F | Me | O | cyclopropyl | CH2 | cyclohexyl (#,*) | — | | phenyl | 4.31 | 406 |
| 241 | F | F | Me | O | cyclopropyl | CH2 | cyclohexyl (#,*) | — | | 2-chlorophenyl | 4.67 | 440 |
| 242 | F | F | Me | O | cyclopropyl | CH2 | cyclohexyl (#,*) | — | | 2,4-dichlorophenyl | 5.31 | 474 |
| 243 | F | F | Me | O | cyclopropyl | | cyclohexyl (#,*) | CH2 | — | phenyl | 4.34 + 4.41[(1)] | 406 |
| 244 | F | F | Me | O | cyclopropyl | | cyclohexyl (#,*) | O | — | phenyl | 3.89 | 408 |
| 245 | F | F | Me | O | H | | cyclohexyl (#,*) | O | — | phenyl | 3.52 | 368 |
| 246 | Cl | F | Me | O | H | | cyclohexyl (#,*) | O | — | phenyl | 3.76 | 384 |
| 247 | F | F | Me | O | cyclopropyl | | cyclohexyl (#,*) | O | — | phenyl | 4.21 | 408 |
| 248 | F | F | Me | O | cyclopropyl | | cyclohexyl (#,*) | O | — | 2,4,6-trichlorophenyl | 5.36 + 5.74[(1)] | 510 |
| 249 | F | F | Me | O | cyclopropyl | | cyclohexyl (#,*) | O | — | 2,4-dichlorophenyl | 4.87 + 5.31[(1)] | 476 |
| 250 | F | F | Me | O | cyclopropyl | | cyclohexyl (#,*) | O | — | 2,6-dichlorophenyl | 4.59 + 4.87[(1)] | 476 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 251 | F | F | Me | O | cyclopropyl | |  | O | — | 2-chlorophenyl | 4.25 + 4.59[(1)] | 442 |
| 252 | Cl | F | Me | O | cyclopropyl | |  | O | — | phenyl | 4.06 + 4.41[(1)] | 424 |
| 253 | F | F | Me | O | methyl | |  | CH2 | — | phenyl | 3.72 | 380 |
| 254 | Cl | F | Me | O | methyl | |  | CH2 | — | phenyl | 3.87 | 396 |
| 255 | F | F | Me | O | H | |  | CH2 | — | 3-chlorophenyl | 4.31 + 4.44 + 4.54[(1)] | 414 |
| 256 | F | F | Me | O | cyclopropyl | |  | | — | phenyl | 4.01 | 392 |
| 257 | Cl | F | Me | O | H | |  | S | — | pyrimidin-2-yl | 2.26 | 388 |
| 258 | F | F | Me | O | H | |  | S | — | pyrimidin-2-yl | 2.17 | 372 |
| 259 | F | F | Me | O | H | |  | O | — | 3-methylphenyl | 3.52 | 368 |
| 260 | Cl | F | Me | O | H | |  | O | — | 3-methylphenyl | 3.78 | 384 |
| 261 | Cl | F | Me | O | methyl | CH2 |  | — | — | phenyl | 2.84 | 340 |
| 262 | F | F | Me | O | methyl | CH2 |  | — | — | phenyl | 2.73 | 324 |
| 263 | Cl | F | Me | O | ethyl | CH2 |  | — | — | phenyl | 3.17 | 354 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 264 | F | F | Me | O | ethyl | CH2 | *-CH=CH-* | — | — | phenyl | 3.02 | 338 |
| 265 | Cl | F | Me | O | 2-methoxyethyl | CH2 | *-CH=CH-* | — | — | phenyl | 3.02 | 384 |
| 266 | F | F | Me | O | 2-methoxyethyl | CH2 | *-CH=CH-* | — | — | phenyl | 2.86 | 368 |
| 267 | F | F | Me | O | tertbutyl | CH2 | *-C≡C-* | — | — | phenyl | 3.83 | 364 |
| 268 | Cl | F | Me | O | tertbutyl | CH2 | *-C≡C-* | — | — | phenyl | 3.96 | 380 |
| 269 | F | F | Me | O | methyl | CH2 | *-C≡C-* | — | — | phenyl | 2.78 | 322 |
| 270 | Cl | F | Me | O | methyl | CH2 | *-C≡C-* | — | — | phenyl | 2.92 | 338 |
| 271 | F | F | Me | O | cyclopropyl | CH2 | *-C≡C-* | — | — | phenyl | 3.19 | 348 |
| 272 | Cl | F | Me | O | cyclopropyl | CH2 | *-C≡C-* | — | — | phenyl | 3.33 | 364 |
| 273 | F | F | Me | O | cyclopentyl | CH2 | *-C≡C-* | — | — | phenyl | 3.73 | 376 |
| 274 | Cl | F | Me | O | cyclopentyl | CH2 | *-C≡C-* | — | — | phenyl | 3.92 | 392 |
| 275 | F | F | Me | O | cyclopropyl | CH2 | *-C≡C-* | — | — | 1-benzofuran-2-yl | 3.55 | 388 |
| 276 | F | F | Me | O | cyclopropyl | CH2 | *-C≡C-* | — | — | 1-benzothiophen-2-yl | 3.85 | 404 |
| 277 | F | F | Me | O | H | CH2 | *-C≡C-* | — | — | 1-benzothiophen-2-yl | 3.19 | 364 |
| 278 | F | F | Me | O | methyl | CH2 | *-C≡C-* | — | — | 1-benzothiophen-2-yl | 3.39 | 378 |
| 279 | F | F | Me | O | cyclopropyl | CH2 | *-C≡C-* | — | — | 2-furyl | 2.70 | 338 |
| 280 | F | F | Me | O | H | CH2 | *-C≡C-* | — | — | 2-furyl | 2.14 | 298 |
| 281 | F | F | Me | O | methyl | CH2 | *-C≡C-* | — | — | 2-furyl | 2.32 | 312 |
| 282 | F | F | Me | O | cyclopropyl | CH2 | *-C≡C-* | — | — | 2-thienyl | 3.00 | 354 |
| 283 | F | F | Me | O | cyclopropyl | CH2 | *-C≡C-* | — | — | 3-methyl-2-thienyl | 3.31 | 368 |
| 284 | F | F | Me | O | H | C(Me)2 | *-C≡C-* | — | — | 4-cyanophenyl | 2.82 | 361 |
| 285 | F | F | Me | O | cyclopropyl | CH2 | *-C≡C-* | — | — | 5-methyl-1-benzothiophen-2-yl | 4.26 | 418 |
| 286 | F | F | Me | O | cyclopropyl | CH2 | *-C≡C-* | — | — | 5-methyl-2-thienyl | 3.37 | 368 |
| 287 | Cl | F | Me | O | cyclopropyl | CH2 | Si(Me)2 | CH2 | — | phenyl | 4.20 | 412 |
| 288 | F | F | Me | O | cyclopropyl | CH2 | Si(Me)2 | CH2 | — | phenyl | 4.03 | 396 |
| 289 | F | F | Me | S | cyclopropyl | CH2 | Si(Me)2 | CH2 | — | phenyl | 4.67 | 412 |
| 290 | Cl | F | Me | O | cyclopropyl | CH2 | Si(Me)2 | CH2 | — | 3-chlorophenyl | 4.59 | 446 |
| 291 | F | F | Me | O | cyclopropyl | CH2 | Si(Me)2 | CH2 | — | 3-chlorophenyl | 4.44 | 430 |
| 292 | Cl | F | Me | O | cyclopropyl | CH2 | Si(Me)2 | CH2 | — | 3,5-dichlorophenyl | 5.14 | 480 |
| 293 | F | F | Me | O | cyclopropyl | CH2 | Si(Me)2 | CH2 | — | 3,5-dichlorophenyl | 4.98 | 464 |
| 294 | Cl | F | Me | O | cyclopropyl | CH2 | Si(Me)2 | CH2 | — | 2-chlorophenyl | 4.56 | 446 |
| 295 | F | F | Me | O | cyclopropyl | CH2 | Si(Me)2 | CH2 | — | 2-chlorophenyl | 4.41 | 430 |
| 296 | F | F | Me | S | cyclopropyl | CH2 | Si(Me)2 | CH2 | — | 2-chlorophenyl | 5.00 | 446[2] |
| 297 | Cl | F | Me | O | cyclopropyl | CH2 | Si(Me)2 | CH2 | — | 2,4-dichlorophenyl | 5.19 | 480 |
| 298 | F | F | Me | O | cyclopropyl | CH2 | Si(Me)2 | CH2 | — | 2,4-dichlorophenyl | 5.03 | 464 |
| 299 | F | F | Me | S | cyclopropyl | CH2 | Si(Me)2 | CH2 | — | 2,4-dichlorophenyl | 5.57 | 480 |
| 300 | Cl | F | Me | O | Et | CH(Me) | CH(Me) | CH2 | CH2 | Me | 3.59 | 336 |
| 301 | F | F | Me | O | Et | CH(Me) | CH(Me) | CH2 | CH2 | Me | 3.35 + 3.39[1] | 320 |
| 302 | F | F | Me | O | cyclopropyl | CH(Me) | CH(Me) | CH2 | — | Me | 3.29 + 3.31[1] | 318 |
| 303 | Cl | F | Me | O | cyclopropyl | CH(Me) | CH(Me) | CH2 | — | Me | 3.52 | 334 |
| 304 | F | F | Me | O | cyclopropyl | CH(Me) | CH2 | CH2 | Si(Me)2 | Me | 4.39 | 362 |
| 305 | F | F | Me | O | H | CH2 | CH2 | CH2 | CH2 | OMe | 1.40 | 280 |
| 306 | F | F | Me | O | H | \#–CH(–)–CH(–)–* (1,2-cyclopentylene) | | CH2 | CH2 | Et | 3.59 | |
| 307 | Cl | F | Me | O | H | \#–CH(–)–CH(–)–* (1,2-cyclopentylene) | | CH2 | CH2 | Et | 3.83 | |
| 308 | F | F | Me | S | H | \#–CH(–)–CH(–)–* (1,2-cyclopentylene) | | CH2 | CH2 | Et | 4.39 | 334 |
| 309 | Cl | F | Me | O | H | \#–CH(–)–CH(–)–* (1,2-cyclopentylene) | | CH2 | CH2 | i-Pr | 4.20 | |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 310 | F | F | Me | O | H | | cyclopentyl (#,*) | CH2 | CH2 | i-Pr | 3.98 | |
| 311 | Cl | F | Me | O | H | | cyclopentyl (#,*) | CH(Me) | CH2 | i-Pr | mixture | |
| 312 | Cl | F | Me | O | H | | cyclopentyl (#,*) | CH(Me) | CH2 | i-Pr | 4.40 isomer A | |
| 313 | Cl | F | Me | O | H | | cyclopentyl (#,*) | CH(Me) | CH2 | i-Pr | 4.46 isomer B | |
| 314 | Cl | F | Me | O | H | | cyclopentyl (#,*) | CH(Me) | CH2 | i-Pr | 4.47 isomer C | |
| 315 | F | F | Me | O | H | | cyclopentyl (#,*) | CH(Me) | CH2 | i-Pr | mixture | |
| 316 | F | F | Me | O | H | | cyclopentyl (#,*) | CH(Me) | CH2 | i-Pr | 4.19 isomer A | |
| 317 | F | F | Me | O | H | | cyclopentyl (#,*) | CH(Me) | CH2 | i-Pr | 4.22 isomer B | |
| 318 | F | F | Me | O | H | | cyclopentyl (#,*) | CH(Me) | CH2 | i-Pr | 4.27 isomer C | |
| 319 | F | F | Me | O | H | | cyclopentyl (#,*) | CH2 | CH2 | t-Bu | 4.22 + 4.28[(1)] | |
| 320 | Cl | F | Me | O | H | | cyclopentyl (#,*) | CH2 | CH2 | t-Bu | 4.49 | |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 321 | F | F | Me | S | H | | cyclopentyl (#,*) | CH2 | CH2 | t-Bu | 5.01 | 362 |
| 322 | F | F | Me | O | cyclopropyl | | 3,3-diMe-cyclohexyl (#,*) | CH2 | | H | 4.31 | 358 |
| 323 | F | F | Me | S | cyclopropyl | | 3,3-diMe-cyclohexyl (#,*) | CH2 | | H | 4.96 | 374 |
| 324 | F | F | Me | O | H | | 1,3-cyclohexyl (#,*) | CH2 | | CH2C(Me)3 | 4.80 | |
| 325 | F | F | Me | O | H | | 1,3-cyclohexyl (#,*) | O | | i-Pr | 2.06 | |
| 326 | F | F | Me | O | H | | 1,2-cyclohexyl (#,*) | CH2 | CH2 | Bu | 5.07 | |
| 327 | F | F | Me | S | H | | 1,2-cyclohexyl (#,*) | CH2 | CH2 | Bu | 5.81 | 376 |
| 328 | Cl | F | Me | O | H | | 1,2-cyclohexyl (#,*) | CH2 | CH(Me) | c-Pr | 4.28 | |
| 329 | F | F | Me | O | H | | 1,2-cyclohexyl (#,*) | CH2 | CH2 | Et | 3.80 isomer A | |
| 330 | F | F | Me | O | H | | 1,2-cyclohexyl (#,*) | CH2 | CH2 | Et | 4.06 isomer B | |
| 331 | Cl | F | Me | O | H | | 1,2-cyclohexyl (#,*) | CH2 | CH2 | Et | 4.10 | |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 332 | F | F | Me | S | H | # | * cyclohexyl | CH2 | CH2 | Et | 4.86 | 348 |
| 333 | F | F | Me | O | H | # | * cyclohexyl | CH2 | CH2 | i-Pr | 4.22 | |
| 334 | Cl | F | Me | O | H | # | * cyclohexyl | CH(Me) | CH2 | i-Pr | 4.75 isomer A | |
| 335 | Cl | F | Me | O | H | # | * cyclohexyl | CH(Me) | CH2 | i-Pr | 4.96 isomer B | |
| 336 | Cl | F | Me | S | H | # | * cyclohexyl | CH(Me) | CH2 | i-Pr | 5.42 | 392 |
| 337 | F | F | Me | O | H | # | * cyclohexyl | CH(Me) | CH2 | i-Pr | 4.47 isomer A | |
| 338 | F | F | Me | O | H | # | * cyclohexyl | CH(Me) | CH2 | i-Pr | 4.73 isomer B | |
| 339 | F | F | Me | O | H | # | * cyclohexyl | CH(Me) | CH2 | i-Pr | 4.54 | |
| 340 | F | F | Me | O | H | # | * cyclohexyl | CH2 | CH(Me) | Me | 3.94 | |
| 341 | F | F | Me | O | H | # | * cyclohexyl | CH(OH) | — | Me | 1.72 isomer A | |
| 342 | F | F | Me | O | H | # | * cyclohexyl | CH(OH) | — | Me | 2.08 isomer B | |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 343 | F | F | Me | O | H | # | * cyclohexyl | CH2 | CH2 | Me | 3.42 isomer A | |
| 344 | F | F | Me | O | H | # | * cyclohexyl | CH2 | CH2 | Me | 3.61 isomer B | |
| 345 | F | F | Me | S | H | # | * cyclohexyl | CH2 | CH2 | Me | 4.21 | 334 |
| 346 | F | F | Me | O | cyclopropyl | # | * cyclohexyl | CH2 | *CH=CH* | H | 3.94 | 356 |
| 347 | Cl | F | Me | O | cyclopropyl | # | * cyclohexyl | CH2 | *CH=CH* | H | 4.16 | 372 |
| 348 | Cl | F | Me | O | H | # | * cyclohexyl | C(Me)2 | — | Me | 4.15 | 348 |
| 349 | F | F | Me | O | H | # | * cyclohexyl | C(Me)2 | — | Me | 3.79 | 332 |
| 350 | F | F | Me | O | cyclopropyl | # | * cyclohexyl | C(Me)2 | — | Me | 4.71 | 372 |
| 351 | F | F | Me | O | cyclopropyl | # | * cyclohexyl | S | — | Me | 3.50 | 362 |
| 352 | Cl | F | Me | O | cyclopropyl | # | * cyclohexyl | S | — | Me | 3.73 | 378 |
| 353 | F | F | Me | O | H | # | * cyclohexyl | CH2 | CH2 | Si(Me)3 | 4.70 | |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 354 | Cl | F | Me | O | H | | cyclohexyl (#,*) | CH2 | CH2 | t-Bu | 4.73 isomer A | |
| 355 | Cl | F | Me | O | H | | cyclohexyl (#,*) | CH2 | CH2 | t-Bu | 4.95 isomer B | |
| 356 | Cl | F | Me | S | H | | cyclohexyl (#,*) | CH2 | CH2 | t-Bu | 5.60 | 392 |
| 357 | F | F | Me | O | H | | cyclohexyl (#,*) | CH2 | CH2 | t-Bu | 4.50 isomer A | |
| 358 | F | F | Me | O | H | | cyclohexyl (#,*) | CH2 | CH2 | t-Bu | 4.51 isomer B | |
| 359 | Cl | F | Me | O | H | | cyclohexyl (#,*) | CH(Me) | CH2 | t-Bu | 5.28 | |
| 360 | F | F | Me | O | H | | cyclohexyl (#,*) | CH(Me) | CH2 | t-Bu | 4.85 isomer A | |
| 361 | F | F | Me | O | H | | cyclohexyl (#,*) | CH(Me) | CH2 | t-Bu | 4.89 isomer B | |
| 362 | Cl | F | Me | O | H | | 3,3,5-trimethylcyclohexyl (#,*) | | CH2 | Me | 4.44 | 362 |
| 363 | F | F | Me | O | H | | 3,3,5-trimethylcyclohexyl (#,*) | | CH2 | Me | 4.23 | 346 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 364 | F | F | Me | O | H | CH2 | #─*cyclohexyl | | CH2 | Me | 3.49 | |
| 365 | Cl | F | Me | O | H | CH2 | #,*-cyclohexyl (gem) | CH2 | — | Me | 3.78 | 334 |
| 366 | F | F | Me | O | H | CH2 | #,*-cyclohexyl (gem) | CH2 | — | Me | 3.55 | 318 |
| 367 | F | F | Me | O | cyclopropyl | CH(Me) | CH2 | CH2 | — | 2,2,6-triMe-cyclohexyl | 5.81 | 414 |
| 368 | Cl | F | Me | O | cyclopropyl | CH(Me) | CH2 | CH2 | — | 2,2,6-triMe-cyclohexyl | 6.07 | 430 |
| 369 | Cl | F | Me | O | cyclopropyl | #─*cyclopentyl | — | — | — | cyclopentyl | 4.83 | 386 |
| 370 | F | F | Me | O | cyclopropyl | CH(Me) | CH2 | — | — | cyclohexyl | 4.36 | 358 |
| 371 | Cl | F | Me | O | cyclopropyl | CH(Me) | CH2 | — | — | cyclohexyl | 4.56 | 374 |
| 372 | F | F | Me | O | cyclopropyl | #─*cyclohexyl | — | — | — | cyclohexyl | 5.28 | 398 |
| 373 | Cl | F | Me | O | cyclopropyl | #─*cyclohexyl | — | — | — | cyclohexyl | 5.59 | 414 |
| 374 | F | F | Me | O | H | #─*cyclohexyl | — | — | — | cyclohexyl | 4.34 | 358 |
| 375 | Cl | F | Me | O | H | #─*cyclohexyl | — | — | — | cyclohexyl | 4.56 | 374 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 376 | F | F | Me | O | cyclopropyl | cyclohexyl (#,*) | — | — | — | cyclohex-1-en-1-yl | 4.88 | 396 |
| 377 | Cl | F | Me | O | cyclopropyl | cyclohexyl (#,*) | — | — | — | cyclohex-1-en-1-yl | 5.17 | 412 |
| 378 | Cl | F | Me | O | H | CH2 | | cyclohexyl (#,*) | — | CF3 | 3.13 + 3.15[(1)] | 374 |
| 379 | F | F | Me | O | H | CH2 | | cyclohexyl (#,*) | — | CF3 | 2.96 | 358 |
| 380 | Cl | F | Me | O | H | cyclopropyl (#,*) | — | — | — | cyclohexyl | 3.29 | 332 |
| 381 | F | F | Me | O | H | cyclopropyl (#,*) | — | — | — | cyclohexyl | 3.11 | 316 |
| 382 | F | F | Me | O | H | cyclohexyl (#,*) | *≡* | — | — | Me | 2.90 | 314 |
| 383 | Cl | F | Me | O | H | cyclohexyl (#,*) | *≡* | — | — | Me | 3.11 | 330 |
| 384 | Cl | F | Me | O | H | cyclohexyl (#,*) | *≡* | — | — | H | 2.73 | 316 |
| 385 | F | F | Me | O | H | cyclohexyl (#,*) | *≡* | — | — | H | 2.56 | 300 |
| 386 | Cl | F | Me | O | H | cyclohexyl (#,*) | — | — | — | CF3 | 3.15 | 360 |

TABLE 1-continued

| Example | X1 | X2 | Y | T | Z1 | Q1 | Q2 | Q3 | Q4 | B | logP | Mass (M + H) |
|---|---|---|---|---|---|---|---|---|---|---|---|---|
| 387 | F | F | Me | O | H | 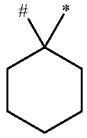 | — | — | — | CF3 | 3.00 | 344 |

Note
[1] mixture of two or more isomers;
Note
[2] mass M;
Note:
denotes the point of attachement to the amide moiety;
*denotes the point of attachement to the side chain.

Table 2 provides the NMR data ($^1$H) of a selected number of compounds from table 1.

The $^1$H-NMR data of selected examples are stated in the form of $^1$H-NMR peak lists. For each signal peak, the δ value in ppm and the signal intensity in brackets are listed:

TABLE 2

Example 306
Solvent: DMSO-d$_6$ 7.7657 (0.35) 7.7492 (0.95) 7.7287 (0.77) 7.5612 (0.53) 7.5402 (0.54)
7.2237 (0.57) 7.2191 (1.23) 7.1717 (0.88) 7.0889 (1.21) 7.0842 (2.72)
7.0368 (1.88) 6.9542 (0.63) 6.9495 (1.34) 6.9022 (0.96) 4.2971 (0.33)
4.2868 (0.39) 4.2812 (0.4) 4.2745 (0.38) 3.809 (0.82) 3.7885 (1.43)
3.7734 (16) 3.5677 (1.1) 3.3526 (0.32) 3.3481 (0.37) 3.3056 (589.57)
2.6737 (0.49) 2.6691 (0.69) 2.6646 (0.5) 2.5392 (0.93) 2.5225 (1.71)
2.5177 (2.67) 2.5091 (36.9) 2.5047 (72.29) 2.5001 (97.2) 2.4957 (66.33)
2.4912 (30.83) 2.3314 (0.46) 2.3268 (0.67) 2.3221 (0.45) 2.0692 (0.62)
1.9867 (0.48) 1.9287 (0.33) 1.923 (0.51) 1.9097 (0.85) 1.9035 (0.51)
1.8911 (1.05) 1.8785 (1.2) 1.8592 (1.36) 1.8506 (1.21) 1.8422 (0.94)
1.8313 (1.03) 1.8192 (0.94) 1.8121 (0.57) 1.8006 (0.52) 1.7597 (0.42)
1.7507 (0.7) 1.7385 (0.87) 1.7295 (1.16) 1.7182 (1.08) 1.7093 (1.58)
1.6878 (1.52) 1.677 (1.17) 1.6629 (0.77) 1.6562 (0.58) 1.6426 (0.63)
1.6312 (0.49) 1.6235 (0.64) 1.611 (0.8) 1.6002 (0.91) 1.5904 (0.96)
1.5808 (0.87) 1.5736 (0.92) 1.5688 (0.84) 1.5585 (1.1) 1.5525 (0.92)
1.5475 (1) 1.5414 (1.24) 1.5322 (0.97) 1.5217 (1.04) 1.5113 (1.04)
1.5051 (0.96) 1.5012 (0.94) 1.4913 (1.15) 1.4839 (1.19) 1.4653 (1.37)
1.4543 (1.19) 1.4486 (1.26) 1.4419 (1.25) 1.4356 (1.12) 1.4168 (0.66)
1.4121 (0.66) 1.3436 (0.54) 1.3228 (0.66) 1.314 (0.65) 1.2897 (1)
1.2779 (1.48) 1.2688 (1.72) 1.2634 (1.75) 1.2593 (1.83) 1.2484 (3.33)
1.2398 (2.67) 1.2314 (2.89) 1.222 (1.92) 1.2132 (1.46) 1.2035 (1.22)
1.1927 (1.16) 1.1827 (1.56) 1.1748 (1.27) 1.1612 (1.3) 1.1518 (1.22)
1.1395 (0.82) 1.1305 (0.94) 1.1156 (0.45) 1.1092 (0.49) 0.8616 (2.28)
0.8443 (4.9) 0.8316 (4.27) 0.8273 (2.42) 0.8195 (0.95) 0.8138 (1.03)
−0.0002 (2.56)
Example 312
Solvent: CD$_3$CN 7.2157 (1.27) 7.1527 (0.7) 7.1439 (1.52) 7.1311 (1.2) 7.1259 (2.77)
7.0629 (1.51) 7.054 (3.13) 7.0412 (2.33) 7.0361 (1.36) 6.9731 (0.75)
6.9642 (1.63) 6.9515 (1.24) 4.5202 (0.48) 4.5131 (0.45) 4.5049 (0.47)
4.4779 (0.52) 4.4698 (0.42) 4.4629 (0.51) 4.1307 (0.53) 4.1175 (0.96)
4.1044 (1.09) 4.0913 (0.7) 3.8568 (11.44) 3.8556 (10.96) 3.8544 (10.51)
3.8501 (16) 2.1768 (124.26) 1.9944 (0.35) 1.9921 (0.73) 1.9815 (0.75)
1.9792 (0.76) 1.9732 (0.64) 1.9709 (0.98) 1.9665 (3.26) 1.9605 (0.94)
1.9584 (1.76) 1.9543 (1.54) 1.9504 (16.34) 1.9463 (32.24) 1.9422 (47.65)
1.9382 (30.99) 1.934 (15.22) 1.9292 (0.8) 1.9253 (0.37) 1.9228 (0.35)
1.8794 (0.36) 1.8749 (0.32) 1.8704 (0.41) 1.8658 (0.68) 1.8622 (0.56)
1.8569 (0.7) 1.8527 (0.7) 1.8477 (0.43) 1.8436 (0.58) 1.8357 (0.58)
1.8318 (0.42) 1.8275 (0.46) 1.8234 (0.35) 1.8197 (0.44) 1.7568 (0.49)
1.7485 (0.64) 1.7466 (0.62) 1.742 (0.64) 1.7343 (1.03) 1.7267 (0.83)
1.7235 (1.17) 1.7201 (1.28) 1.7142 (1.31) 1.7062 (1.7) 1.6915 (1.39)
1.6875 (1.54) 1.6817 (1.52) 1.6749 (1.61) 1.67 (1.46) 1.6645 (1.77)
1.66 (1.31) 1.6581 (1.48) 1.655 (1.59) 1.6532 (1.5) 1.6473 (1.69) 1.644
(1.65) 1.6365 (1.74) 1.6338 (1.49) 1.6313 (1.24) 1.6267 (1.66) 1.6225
(2.13) 1.6157 (1.88) 1.611 (1.9) 1.6094 (1.82) 1.6045 (1.44) 1.5986
(1.48) 1.5914 (0.82) 1.5879 (0.78) 1.5838 (0.58) 1.5789 (0.36) 1.5705
(0.34) 1.5177 (0.48) 1.5064 (0.79) 1.5025 (0.6) 1.4957 (0.96) 1.4917

TABLE 2-continued (0.87) 1.4839 (1.17) 1.4794 (0.78) 1.473 (0.97) 1.4678 (0.77) 1.4615
(0.5) 1.4563 (0.43) 1.4505 (0.4) 1.4363 (11.79) 1.3752 (0.33) 1.365
(0.69) 1.3585 (0.46) 1.3503 (0.77) 1.3454 (0.8) 1.3363 (0.78) 1.3293
(0.75) 1.3218 (0.58) 1.3159 (0.94) 1.3104 (0.69) 1.3006 (0.53) 1.2981
(0.56) 1.2931 (0.9) 1.2882 (0.72) 1.2757 (0.49) 1.2704 (0.6) 1.2301
(0.34) 1.2249 (0.34) 1.212 (0.47) 1.2077 (0.73) 1.2041 (0.47) 1.203
(0.47) 1.1896 (0.74) 1.1848 (0.89) 1.175 (0.51) 1.1711 (0.52) 1.1668
(0.33) 1.1622 (1) 1.1529 (0.69) 1.1487 (0.76) 1.1392 (0.63) 1.114 (0.5)
1.1023 (0.97) 1.0921 (0.75) 1.0881 (0.76) 1.0797 (0.54) 1.078 (0.77)
1.0698 (0.43) 1.0658 (0.44) 1.0557 (0.69) 1.0485 (0.74) 1.0424 (0.48)
1.0391 (0.33) 1.0313 (0.68) 1.026 (0.75) 1.0203 (0.4) 1.0091 (0.54)
1.0054 (0.57) 1.0028 (0.42) 0.9993 (0.51) 0.9874 (0.49) 0.983 (0.61)
0.9816 (0.59) 0.9773 (0.45) 0.9654 (0.41) 0.9593 (0.4) 0.904 (3.49)
0.8926 (9.38) 0.8817 (13.38) 0.8713 (7.79) 0.8695 (6.32) 0.8616 (9.02)
0.858 (0.81) 0.8506 (8.87) 0.8451 (9.19) 0.8432 (10.55) 0.8423 (11.04)
0.834 (8.78) 0.8315 (10.76) 0.8235 (5.81) 0.8127 (5.69) 0.8096 (3.91)
0.7987 (3.56) 0.6928 (6.25) 0.682 (6.11) −0.0002 (1.09)
Example 316
Solvent: CD$_3$CN 7.2147 (0.44) 7.2082 (0.82) 7.183 (0.78) 7.1327 (0.56) 7.0797 (0.89)
7.0733 (1.67) 7.0482 (1.6) 6.9979 (1.11) 6.9448 (0.46) 6.9384 (0.84)
6.9134 (0.81) 6.8631 (0.57) 4.5032 (0.35) 4.4808 (0.34) 4.1165 (0.64)
4.0966 (0.75) 4.0765 (0.46) 3.7434 (12.99) 2.1409 (72.15) 1.9827 (0.47)
1.9711 (1.8) 1.9631 (1.7) 1.957 (1.86) 1.9512 (10.83) 1.945 (19.73)
1.9389 (27.64) 1.9327 (19.24) 1.9265 (9.8) 1.9114 (0.76) 1.9003 (0.56)
1.8964 (0.48) 1.8899 (0.56) 1.8817 (0.53) 1.8755 (0.51) 1.8679 (0.35)
1.8622 (0.48) 1.8592 (0.45) 1.8528 (0.43) 1.8399 (0.47) 1.8272 (0.43)
1.7736 (0.38) 1.7673 (0.43) 1.7612 (0.34) 1.7546 (0.42) 1.7457 (0.54)
1.7335 (0.73) 1.7254 (0.74) 1.7132 (1.07) 1.7073 (0.93) 1.6958 (1.31)
1.6897 (1.17) 1.6794 (1.69) 1.6734 (1.59) 1.6701 (1.53) 1.6634 (1.78)
1.6606 (1.75) 1.6568 (1.88) 1.6473 (1.94) 1.6389 (1.73) 1.631 (2.19)
1.6149 (1.88) 1.611 (1.83) 1.5975 (1.75) 1.5885 (1.04) 1.5825 (1.12)
1.579 (1.04) 1.5683 (0.68) 1.5638 (0.65) 1.5006 (0.44) 1.4847 (0.45)
1.4774 (0.45) 1.4691 (0.64) 1.4609 (0.54) 1.4527 (0.64) 1.4371 (2.96)
1.4267 (0.56) 1.4185 (0.55) 1.4093 (0.35) 1.4012 (0.32) 1.3917 (0.36)
1.3682 (0.39) 1.361 (0.58) 1.3419 (0.79) 1.3257 (0.54) 1.3147 (0.82)
1.2989 (0.41) 1.2884 (0.67) 1.2813 (0.77) 1.2738 (0.54) 1.2549 (0.43)
1.2471 (0.41) 1.2215 (0.48) 1.2176 (0.39) 1.21 (0.56) 1.2037 (1) 1.1857
(0.84) 1.1742 (0.53) 1.1682 (0.34) 1.1543 (0.7) 1.14 (0.5) 1.1346 (0.53)
1.1199 (0.42) 1.0958 (0.51) 1.0801 (0.54) 1.0748 (0.53) 1.0592 (0.58)
1.0553 (0.45) 1.0514 (0.38) 1.0461 (0.59) 1.0409 (0.46) 1.0265 (0.52)
1.0197 (0.52) 1.0018 (0.44) 0.9933 (0.6) 0.9749 (0.4) 0.9679 (0.46)
0.9596 (0.34) 0.9418 (0.32) 0.8966 (3.97) 0.8926 (2.77) 0.8804 (7.7)
0.8759 (3.22) 0.8662 (5.67) 0.858 (5.97) 0.8527 (3.83) 0.8416 (16)
0.8345 (4.77) 0.8252 (10.7) 0.8182 (4.04) 0.8049 (2.39) 0.7886 (2.17)
0.6955 (3.9) 0.6791 (3.76) 0.008 (0.47) −0.0002 (11.82) −0.0086 (0.45)
Example 319
Solvent: DMSO-d$_6$ 7.2105 (0.41) 7.0755 (0.92) 7.0349 (0.53) 6.9408 (0.45) 4.0393 (0.45)
4.0215 (0.45) 3.79 (0.48) 3.7742 (3.73) 3.3093 (168.59) 2.5228 (0.43)
2.5181 (0.66) 2.5094 (9.06) 2.505 (17.8) 2.5005 (24.03) 2.496 (16.41)
2.4915 (7.68) 1.9867 (2.05) 1.8508 (0.33) 1.5979 (0.37) 1.5843 (0.37)
1.4587 (0.38) 1.1929 (0.79) 1.1751 (1.58) 1.1683 (0.37) 1.1573 (1.02)
1.1472 (1.02) 1.1219 (0.84) 1.1154 (0.51) 1.0992 (0.74) 0.8486 (1.04)
0.8438 (1.07) 0.8324 (16) 0.8221 (1.24) 0.8126 (9.14) 0.8007 (0.7)
0.7906 (0.98) 0.7852 (0.8) −0.0002 (1.73)

TABLE 2-continued

Example 326
Solvent: DMSO-d$_6$ 7.6444 (1.62) 7.6244 (1.63) 7.2284 (1.97) 7.0936 (4.54) 6.9589 (2.17)
3.7683 (14.62) 3.7159 (0.32) 3.7036 (0.41) 3.6844 (0.77) 3.6745 (0.95)
3.6649 (0.83) 3.6549 (0.95) 3.6454 (0.78) 3.6363 (0.47) 3.6258 (0.42)
3.4746 (0.38) 3.3181 (533.16) 3.2959 (4.34) 3.2707 (0.33) 2.6747 (0.34)
2.6702 (0.44) 2.5401 (0.67) 2.5233 (1.66) 2.5099 (24.83) 2.5055 (46.48)
2.5011 (60.77) 2.4967 (42.16) 2.4923 (20.06) 2.3279 (0.38) 2.0689 (1.12)
1.8494 (1.07) 1.8164 (1.83) 1.7797 (0.99) 1.7332 (1.01) 1.7254 (0.81)
1.717 (0.63) 1.7081 (0.93) 1.7009 (1.22) 1.6936 (0.97) 1.6638 (1.03)
1.6331 (1.07) 1.3223 (1) 1.2895 (2.73) 1.2784 (3.48) 1.2438 (16) 1.2067
(2.19) 1.1926 (2.42) 1.1834 (2.87) 1.1768 (2.89) 1.163 (1.34) 1.1221
(0.41) 1.114 (0.37) 0.9417 (0.78) 0.912 (2.05) 0.8819 (2.36) 0.8729 (3.89)
0.8563 (11.23) 0.839 (4.04) 0.8132 (0.44) 0.8056 (0.48) 0.7821 (0.98)
0.7744 (0.97) 0.7521 (0.89) 0.7439 (0.88) 0.7216 (0.36) 0.008 (0.37)
−0.0002 (8.1)
Example 330
Solvent: DMSO-d$_6$ 7.4069 (1.5) 7.3849 (1.5) 7.1692 (2.38) 7.0345 (5.15) 6.9 (2.63) 4.1114
(1.13) 4.1029 (1.11) 3.8657 (0.57) 3.7749 (16) 3.7578 (0.4) 3.3014
(141.26) 2.5224 (0.75) 2.5176 (1.21) 2.509 (12.2) 2.5046 (23) 2.5001
(30.25) 2.4957 (20.51) 2.4912 (9.48) 2.0696 (2.94) 1.6631 (1.28)
1.6504 (1.04) 1.6372 (0.78) 1.619 (0.42) 1.5971 (1.06) 1.5906 (1.02)
1.5618 (1.59) 1.5373 (1.03) 1.4726 (1.14) 1.4491 (3.19) 1.4341 (5)
1.4087 (1.02) 1.3544 (0.5) 1.3464 (0.46) 1.3271 (1.06) 1.3202 (1.1)
1.2941 (1.69) 1.2661 (1.85) 1.2546 (2.18) 1.2321 (6.94) 1.2287 (7.18)
1.2199 (8.09) 1.2036 (2.68) 1.1809 (0.76) 1.1628 (0.93) 1.1444 (1.04)
1.1255 (0.94) 1.1076 (0.48) 0.8495 (3.55) 0.8404 (3.19) 0.8324 (9.9)
0.8149 (2.86) −0.0002 (1.5)
Example 333
Solvent: DMSO-d$_6$ 7.6924 (0.47) 7.6706 (0.46) 7.433 (0.86) 7.4116 (0.88) 7.201 (0.56)
7.1647 (1.15) 7.066 (1.2) 7.03 (2.44) 6.9313 (0.62) 6.8954 (1.23)
4.139 (0.51) 4.117 (0.67) 4.1084 (0.65) 3.7753 (12.35) 3.7007 (0.39)
3.4947 (0.33) 3.4863 (0.36) 3.473 (0.49) 3.4654 (0.68) 3.4449 (0.32)
3.436 (0.32) 3.322 (53.06) 2.9918 (0.62) 2.8915 (0.45) 2.7326 (0.35)
2.51 (12.59) 2.5058 (23.15) 2.5015 (29.75) 2.4972 (20.92) 1.822
(0.34) 1.7828 (0.53) 1.7616 (0.45) 1.6633 (1.29) 1.6523 (1.07) 1.6382
(0.84) 1.5957 (0.78) 1.5901 (0.76) 1.5604 (0.75) 1.5292 (0.91) 1.5196
(1.04) 1.5028 (1.3) 1.493 (0.8) 1.475 (1.52) 1.4592 (1.79) 1.4426
(3.18) 1.4313 (3.74) 1.4115 (1.62) 1.3567 (0.99) 1.3359 (0.96) 1.329
(1.01) 1.3026 (1.34) 1.2767 (1.57) 1.2464 (1.93) 1.2299 (1.74) 1.2104
(1.28) 1.1987 (1.04) 1.1891 (1.02) 1.1804 (1.06) 1.1603 (1.42) 1.1529
(1.83) 1.1389 (2.94) 1.1265 (3.48) 1.1038 (1.13) 1.0792 (0.66) 1.0646
(0.62) 1.0506 (0.92) 1.0341 (0.99) 1.0267 (0.8) 1.0055 (0.55) 0.9976
(0.46) 0.9849 (0.36) 0.9741 (0.54) 0.9689 (0.53) 0.9435 (0.38) 0.8783
(0.79) 0.8719 (1.14) 0.867 (1.83) 0.8616 (1.43) 0.8557 (1.77) 0.8503
(2.23) 0.8319 (12.16) 0.8201 (10.95) 0.8155 (16) 0.8037 (9.49) 0.7994
(5.7) 0.7742 (0.88) 0.7674 (0.75) 0.7579 (0.61) 0.7499 (0.49) 0.7414
(0.45) 0.7249 (0.36) 0.7083 (0.32) −0.0002 (2.31)
Example 334
Solvent: DMSO-d$_6$ 7.8032 (0.32) 7.7607 (0.59) 7.7382 (0.6) 7.1657 (0.89) 7.1602 (0.5)
7.0306 (2.02) 7.025 (0.98) 6.8955 (1) 6.8899 (0.56) 3.8645 (9.89) 3.7287
(0.32) 3.7191 (0.34) 3.7063 (0.44) 3.6957 (0.45) 3.2898 (163.83) 2.668
(0.34) 2.538 (0.69) 2.5214 (1) 2.5165 (1.6) 2.5081 (18.42) 2.5035 (37.5)
2.499 (50.91) 2.4944 (35.99) 2.4898 (16.62) 2.067 (16) 1.9377 (0.33)
1.9209 (0.4) 1.9138 (0.41) 1.9069 (0.4) 1.8949 (0.37) 1.8251 (0.51) 1.817
(0.53) 1.6918 (1.19) 1.6678 (1.49) 1.567 (0.4) 1.5486 (0.36) 1.5339 (0.41)
1.5183 (0.46) 1.5023 (0.43) 1.3433 (0.36) 1.3148 (0.72) 1.2849 (0.5)
1.2778 (0.54) 1.2473 (0.8) 1.2226 (0.97) 1.2015 (0.64) 1.1161 (0.59)
1.1088 (0.6) 1.0994 (0.52) 1.0834 (1) 1.0703 (0.54) 1.0579 (0.53) 1.0498
(0.78) 1.032 (0.48) 1.0151 (0.52) 0.9969 (0.48) 0.9894 (0.44) 0.981 (0.41)
0.9633 (0.36) 0.9474 (0.47) 0.9377 (0.43) 0.9188 (0.44) 0.915 (0.45)
0.9092 (0.48) 0.8867 (0.35) 0.8766 (0.44) 0.8628 (2.61) 0.8486 (6.05)
0.8429 (5.04) 0.8323 (5.48) 0.8285 (4.65) 0.8256 (4.81) 0.8122 (2.46)
0.7999 (0.33) 0.7217 (4.69) 0.7152 (2.8) 0.7055 (4.49) 0.6981 (2.47)
−0.0002 (6.7)
Example 335
Solvent: DMSO-d$_6$ 7.636 (1.01) 7.6135 (1.02) 7.5345 (0.52) 7.5127 (0.53) 7.1804 (0.83)
7.1666 (1.59) 7.0452 (1.78) 7.0315 (3.51) 7.0257 (0.5) 6.9101 (0.92)
6.8965 (1.74) 4.3874 (0.38) 4.3812 (0.41) 4.365 (0.42) 4.3431 (0.74)
4.3364 (0.73) 4.3205 (0.73) 4.3145 (0.67) 3.8684 (16) 3.2902 (124.98)
3.2673 (2.37) 2.5383 (0.44) 2.5214 (0.78) 2.5083 (11.52) 2.5038 (22.91)
2.4992 (30.77) 2.4946 (21.63) 2.4901 (10.03) 2.0673 (1.43) 1.7708 (0.79)
1.7551 (1) 1.7474 (0.89) 1.7088 (1.49) 1.6932 (2.05) 1.6337 (0.4) 1.624
(0.52) 1.6171 (0.69) 1.6081 (0.85) 1.6006 (0.92) 1.5923 (0.92) 1.5838
(0.86) 1.5758 (0.76) 1.5675 (0.64) 1.5596 (0.39) 1.437 (1.78) 1.4241 (1.59)
1.4147 (1.86) 1.3974 (1.7) 1.3842 (1.27) 1.3764 (1.47) 1.3598 (1.07)
1.3521 (1.19) 1.3452 (0.9) 1.3359 (0.85) 1.3284 (0.92) 1.3203 (0.59)
1.3119 (0.58) 1.3026 (0.65) 1.2933 (0.5) 1.2683 (1.49) 1.2607 (1.06)
1.2427 (1.97) 1.2359 (2.08) 1.2278 (1.24) 1.212 (2.04) 1.203 (1.47) 1.1931
(1.29) 1.1718 (0.9) 1.1632 (0.76) 1.1384 (0.99) 1.1136 (0.84) 1.1064 (0.81)
1.0838 (0.42) 0.9178 (0.71) 0.9078 (1) 0.8984 (0.59) 0.8928 (0.82) 0.883
(1.57) 0.8707 (8.87) 0.8632 (2.21) 0.8542 (8.57) 0.8467 (6.31) 0.8301
(5.28) 0.82 (0.91) 0.8125 (1.28) 0.7966 (8.24) 0.7844 (13.33) 0.7806 (8.71)
0.7685 (8.15) 0.7151 (5.15) 0.6988 (4.96) −0.0002 (3.34)
Example 343
Solvent: DMSO-d$_6$ 7.652 (1.66) 7.6298 (1.68) 7.2099 (2.55) 7.0749 (5.52) 6.9402 (2.83)
4.1406 (0.41) 3.7762 (16) 3.5069 (0.43) 3.4908 (0.83) 3.4809 (1.04)
3.4683 (1.37) 3.458 (0.91) 3.4421 (0.4) 3.4319 (0.33) 3.3041 (98.21)
2.5228 (0.52) 2.5179 (0.81) 2.5094 (7.95) 2.505 (14.97) 2.5005 (19.67)
2.496 (13.33) 2.4916 (6.15) 2.0697 (7.08) 1.8331 (1.06) 1.8177 (0.59)
1.803 (1.28) 1.7953 (1.28) 1.7789 (1.07) 1.7684 (1.21) 1.7622 (1.22)
1.7574 (1.23) 1.6845 (1.19) 1.6631 (1.78) 1.63 (1.18) 1.4884 (0.37) 1.4811
(0.45) 1.4746 (0.48) 1.4665 (0.6) 1.4626 (0.7) 1.4555 (0.97) 1.4488 (1.02)
1.4409 (0.92) 1.4309 (0.76) 1.4233 (0.91) 1.418 (0.89) 1.4106 (0.93)
1.3986 (0.68) 1.3889 (0.7) 1.3812 (0.7) 1.369 (1.15) 1.3571 (1.16)
1.35 (1.21) 1.3392 (1.66) 1.332 (1.54) 1.3238 (1.16) 1.3124 (1.61) 1.3061
(1.29) 1.2971 (0.72) 1.2922 (0.68) 1.2782 (1.64) 1.2495 (2.64) 1.2384
(1.14) 1.226 (1.76) 1.1906 (1.15) 1.1775 (0.93) 1.1663 (1.29) 1.1595 (1.6)
1.152 (1.56) 1.1489 (1.51) 1.1416 (1.11) 1.1344 (1.71) 1.1201 (1.14)
1.1169 (1.17) 1.1026 (0.77) 1.0861 (0.37) 1.0702 (0.76) 1.0593 (0.74)
1.0485 (0.73) 1.0382 (1.31) 1.0276 (0.75) 1.0219 (0.57) 1.0166 (0.85)
1.0131 (1) 1.0033 (1) 0.9923 (0.89) 0.9819 (0.49) 0.9698 (1.17) 0.9636
(1.03) 0.9398 (0.97) 0.9323 (0.86) 0.9082 (0.37) 0.8369 (7.5) 0.8189 (15.5)
0.8011 (5.59) −0.0002 (0.84)
Example 344
Solvent: DMSO-d$_6$ 7.3972 (1.36) 7.3755 (1.39) 7.1723 (2.53) 7.0376 (5.47) 6.9031 (2.8)
4.1106 (1.1) 4.1019 (1.09) 3.8658 (0.6) 3.7749 (16) 3.303 (283.9) 2.669
(0.37) 2.5391 (0.54) 2.5224 (1.13) 2.5177 (1.76) 2.509 (20.22) 2.5045
(38.92) 2.5 (52.05) 2.4955 (35.35) 2.491 (16.46) 2.3268 (0.36) 2.0694
(4.18) 1.6614 (1.33) 1.6491 (1.05) 1.6352 (0.83) 1.5935 (1.5) 1.5868 (1.58)
1.5779 (1.73) 1.5699 (1.71) 1.5613 (1.6) 1.4814 (0.8) 1.4514 (2.92) 1.4367
(5.34) 1.4104 (1.1) 1.4026 (0.87) 1.3472 (0.51) 1.3398 (0.48) 1.3199 (1.16)
1.3131 (1.17) 1.3015 (0.77) 1.2866 (2.86) 1.2668 (3.78) 1.2495 (5.06)
1.2351 (3.46) 1.2327 (3.49) 1.2193 (2.16) 1.2034 (1.77) 1.1865 (1.11)
1.1825 (1.26) 1.1656 (0.75) 1.1582 (0.71) 1.1501 (0.62) 1.1438 (1.31)
1.1231 (1.31) 1.1108 (0.8) 1.1052 (0.73) 1.0912 (0.58) 0.8754 (0.4) 0.8577
(0.89) 0.8417 (6.23) 0.833 (1.96) 0.8244 (13.45) 0.8063 (6.11) −0.0002
(2.62)
Example 354
Solvent: DMSO-d$_6$ 7.8628 (0.34) 7.8404 (0.35) 7.1594 (0.47) 7.0241 (1.04) 6.8891 (0.53)
3.8649 (4) 3.2896 (60.33) 2.508 (5.24) 2.5035 (10.59) 2.4989 (14.32)
2.4943 (10.13) 2.4898 (4.71) 2.067 (0.66) 1.8013 (0.37) 1.6664 (0.38)
1.2869 (0.33) 1.2667 (0.5) 1.2542 (0.55) 1.2328 (0.66) 1.0099 (0.8)
0.988 (0.37) 0.9807 (0.45) 0.82 (16) −0.0002 (1.46)
Example 355
Solvent: DMSO-d$_6$ 7.1667 (0.44) 7.0315 (0.98) 6.8965 (0.49) 3.8698 (3.74) 3.2879 (20.21)
3.2641 (0.69) 2.5081 (1.95) 2.5035 (3.91) 2.4989 (5.29) 2.4944 (3.74)
2.4899 (1.74) 2.0671 (4.7) 1.4676 (0.46) 1.4465 (0.83) 1.4374 (0.74)
1.2051 (0.35) 1.1741 (0.38) 1.1272 (0.47) 1.1042 (0.34) 0.8198 (16)
−0.0002 (0.38)
Example 358
Solvent: DMSO-d$_6$ 7.7273 (0.35) 7.7052 (0.36) 7.1934 (0.43) 7.0584 (0.98) 6.9236 (0.5)
3.7745 (3.05) 3.3107 (118.65) 2.5227 (0.64) 2.5093 (7.8) 2.5049 (14.31)
2.5004 (18.44) 2.496 (12.62) 2.4916 (6.04) 1.7773 (0.43) 1.6623 (0.4)
1.2665 (0.56) 1.2417 (0.71) 1.2167 (0.49) 1.0095 (0.83) 0.9904 (0.63)
0.9831 (0.49) 0.8194 (0.56) 0.8044 (16) −0.0002 (0.37)
Example 361
Solvent: DMSO-d$_6$ 7.6998 (0.59) 7.6774 (0.61) 7.1848 (0.46) 7.0497 (0.93) 6.9157 (0.48)
3.7781 (5.13) 3.6192 (0.34) 3.5954 (0.39) 3.3091 (188.57) 3.3066

TABLE 2-continued (192.79) 2.6695 (0.37) 2.5001 (53.35) 2.4964 (50.37) 2.3268 (0.36)
1.8674 (0.63) 1.8455 (0.79) 1.6884 (0.64) 1.6629 (0.88) 1.6267 (0.5)
1.3116 (0.9) 1.2911 (0.39) 1.2761 (0.86) 1.2346 (0.34) 1.2012 (0.54)
1.1712 (0.84) 1.1395 (0.45) 1.1174 (0.39) 1.0878 (0.32) 0.9834 (0.43)
0.9417 (2.83) 0.9253 (2.73) 0.8605 (1.23) 0.8332 (0.68) 0.7964 (16)
0.7768 (0.69) −0.0002 (3.56) −0.0032 (3.32)
Example 363
Solvent: DMSO-d$_6$ 5.8221 (1.12) 3.8508 (1.53) 3.7829 (0.91) 3.7612 (0.76) 3.7535 (0.51)
3.3821 (87.87) 3.3589 (0.94) 2.5851 (6.75) 2.5808 (12.43) 2.5764 (16)
2.572 (11.07) 2.5678 (5.34) 1.752 (0.39) 1.7147 (0.45) 1.6778 (0.46)
1.565 (0.35) 1.5589 (0.37) 1.5271 (0.53) 1.5228 (0.53) 1.5038 (0.56)
1.4743 (0.51) 1.4322 (0.35) 1.3199 (0.59) 1.3117 (0.62) 1.2912 (0.52)
1.2758 (0.45) 1.2689 (0.47) 1.251 (0.6) 1.2417 (0.51) 1.2332 (0.56)
1.2272 (0.53) 1.2173 (0.52) 1.209 (0.52) 1.1829 (0.38) 0.0755 (0.75)
0.0471 (0.8) 0.0411 (0.5) 0.0325 (0.89) 0.0291 (0.83) 0.0266 (1.07)
0.0208 (2.71) 0.0135 (2.05) 0.0071 (5.2) −0.0002 (6.36) −0.0032 (5.69)
−0.0059 (5.4) −0.007 (5.33) −0.0136 (3.64) −0.0159 (3.31) −0.0181
(4.06) −0.0241 (4.65) −0.0361 (2.89) −0.0427 (2.74)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. The $^1$H-NMR peak lists are similar to classical $^1$H-NMR prints and contain therefore usually all peaks, which are listed at classical NMR-interpretation. Additionally they can show like classical 1H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-d6 and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

The following examples illustrate in a non-limiting manner the preparation and efficacy of the compounds of formula (I) according to the invention.

PREPARATION EXAMPLE 1

Preparation of N-cyclopropyl-N-[2-(2,6-dichlorophenoxy)ethyl]-3-(difluoromethyl)-5-fluoro-1-methyl-1H-pyrazole-4-carboxamide (compound 124)

Step 1: preparation of 5-chloro-3-(difluoromethyl)-1-methyl-1H-pyrazole-4-carboxylic acid (IIIa-1)

In a 500 ml flask, 6.0 g (31 mmol) of 5-chloro-3-(difluoromethyl)-1-methyl-1H-pyrazole-4-carbaldehyde are added to 30 ml of toluene. A solution of 2.4 g (62 mmol) of sodium hydroxide in 6 ml of water is added to the reaction mixture, followed by 103 ml of a 30% solution of hydrogen peroxide in water, whilst keeping the temperature below 37° C. After the end of the addition, the reaction mixture is stirred at 50° C. for 7 hours. Once the reaction mixture is back to room temperature, the two phases are separated and the organic phase is extracted with 100 ml of water. The combined aqueous phases are acidified to pH 2 with aqueous hydrochloric acid. The resulting white precipitate is filtered, washed twice with 20 ml of water, and dried to yield 3.2 g of 5-chloro-3-(difluoromethyl)-1-methyl-1H-pyrazole-4-carboxylic acid as a white solid. $^1$H NMR (400 MHz, DMSO-d$_6$) δ ppm: 3.78 (s, 3H); 7.12 (t, 1H, JHF=53.60 Hz) 13.19 (s, 1H); IR (KBr): 1688 cm$^{-1}$ (C=O); 2200-3200 cm$^{-1}$ broad (hydrogen bond).

Step 2: preparation of 5-chloro-3-(difluoromethyl)-1-methyl-1H-pyrazole-4-carbonyl chloride (IIIb-1)

3.2 g of 5-chloro-3-(difluoromethyl)-1-methyl-1H-pyrazole-4-carboxylic acid and 44.3 ml of thionyl chloride are refluxed for 5 hours. After cooling down, the reaction mixture is evaporated under vacuum to yield 3.5 g of 5-chloro-3-(difluoromethyl)-1-methyl-1H-pyrazole-4-carbonyl chloride as a yellow oil. $^1$H NMR (400 MHz, CHCl3-d$_6$) δ ppm: 3.97 (s, 3H); 7.00 (t, J=52.01 Hz, 1H); IR (TQ): 1759 and 1725 cm$^{-1}$ (C=O).

Step 3: preparation of 3-(difluoromethyl)-5-fluoro-1-methyl-1H-pyrazole-4-carbonyl fluoride (IIIc-1)

To a dried solution of 4.0 g (70 mmol) of potassium fluoride in 21 ml of tetrahydrothiophene-1,1-dioxide is added a solution of 5.0 g (22 mmol) of 5-chloro-3-(difluoromethyl)-1-methyl-1H-pyrazole-4-carbonyl chloride in 15 ml of toluene at 100° C. The resulting reaction mixture is stirred at 190-200° C. for 22 hours. Distillation under vacuum yields 8 g of a solution (25% molar) of 3-(difluoromethyl)-5-fluoro-1-methyl-1H-pyrazole-4-carbonyl fluoride in tetrahydrothiophene-1,1-dioxide. $^1$H NMR (250 MHz, CHCl$_3$-d$_6$) δ ppm: 3.87 (s, 3H); 6.79 (t, J=53.75 Hz, 1H); $^{19}$F NMR (250 MHz, CHCl$_3$-d$_6$) δ ppm: 45.37 (s, COF); −117.5 (d, J=28.2 Hz); −131.6 (m).

Step 4: preparation of 3-(difluoromethyl)-5-fluoro-1-methyl-1H-pyrazole-4-carboxylic acid (IIId-1)

To 400 ml of a 1N sodium hydroxyde aqueous solution, is added dropwise 67.5 g of a solution (10% molar) of 3-(difluoromethyl)-5-fluoro-1-methyl-1H-pyrazole-4-carbonyl fluoride in tetra-hydrothiophene-1,1-dioxide. The temperature is kept below 20° C. during the addition. After 2 hours of stirring at room temperature, the reaction mixture is carefully acidified to pH 2 with concentrated aqueous hydrochloric acid. The resulting white precipitate is filtered, washed with water, and dried to yield 6 g of 3-(difluoromethyl)-5-fluoro-1-methyl-1H-pyrazole-4-carboxylic acid as a white solid. $^1$H NMR (400 MHz, DMSO-d$_6$) δ ppm: 3.90 (s, 3H); 7.22 (t, 1H, J$_{HF}$=53.55 Hz); 13.33 (s, 1H).

Step 5: preparation of 3-(difluoromethyl)-5-fluoro-1-methyl-1H-pyrazole-4-carbonyl chloride (IIIe-1)

9.1 g of 3-(difluoromethyl)-5-fluoro-1-methyl-1H-pyrazole-4-carboxylic acid and 75.5 ml of thionyl chloride are refluxed for 1.5 hours. After cooling down, the reaction mixture is evaporated under vacuum to yield 10 g of 3-(difluoromethyl)-5-fluoro-1-methyl-1H-pyrazole-4-carbonyl chloride as a yellow oil. GC-MS; observed M/z: Molecular ion: (M$^+$)=212; fragments: (M$^+$-Cl)=177 and (M$^+$-F)=193.

Step 6: preparation of N-cyclopropyl-N-[2-(2,6-dichlorophenoxy)ethyl]-3-(difluoromethyl)-5-fluoro-1-methyl-1H-pyrazole-4-carboxamide In a 13 ml Chemspeed™ vial is weighted 73 mg (0.726 mmol) of triethylamine. Then 3 ml of a 0.23 molar solution of N-[2-(2,6-dichlorophenoxy)ethyl]cyclopropanamine (0.594 mmole) in dichloromethane is added followed by 3 ml of a 0.26 molar solution of 3-(difluoromethyl)-5-fluoro-1-methyl-1H-pyrazole-4-carbonyl chloride (0.66 mmole) in dichloromethane and stirred at ambient temperature for 15 hrs. 1 ml of water is then added and the mixture is deposited on a basic alumina cartridge (2 g) and eluted twice by 8 ml of dichloromethane. The solvents are removed to yield 183 mg (64%) of pure N-cyclopropyl-N-[2-(2,6-dichlorophenoxy)ethyl]-3-(difluoromethyl)-5-fluoro-1-methyl-1H-pyrazole-4-carboxamide as an oil (M+H=422).

PREPARATION EXAMPLE 2

Preparation of 3-(difluoromethyl)-N-[2-(3,3-dimethylbutyl)cyclopentyl]-5-fluoro-1-methyl-1H-pyrazole-4-carboxamide (compound 319)

Step 1: preparation of methyl 1-(3,3-dimethylbutyl)-2-oxocyclopentanecarboxylate 117.0 g (846.0 mmol) of potassium carbonate are added to a solution consisting of 40.0 g (281.7 mmol) of methyl 2-oxocyclopentanecarboxylate in 160 ml of dry toluene. 93 g (563.4 mmol) of 1-bromo-3,3-dimethylbutane are then added dropwise, and the mixture is stirred at reflux for 14 hours. After the reaction has ended the mixture is cooled to room temperature and filtered off through Celite. The product is concentrated under reduced pressure and purified by column chromatography (silica gel 100-200 mesh, mobile phase: ethyl acetate 5%/petroleum ether). This gives 48 g (75% of theory) of methyl 1-(3,3-dimethylbutyl)-2-oxocyclopentanecarboxylate.

Step 2: preparation of 2-(3,3-dimethylbutyl)cyclopentanone

A solution consisting of 23.0 g (101.7 mmol) of methyl 1-(3,3-dimethylbutyl)-2-oxocyclopentanecarboxylate in 80 ml of acetic acid and 80 ml of conc. hydrochloric acid is stirred at 90° C. for 14 hours. After the reaction has ended, the mixture is cooled to room temperature and ice-water is added. The product is extracted with diethyl ether. The org. phase is washed with water, dried with sodium sulphate and concentrated under reduced pressure. The crude product is purified by column chromatography (silica gel 60-120, mobile phase: ethyl acetate 3%/petroleum ether). This gives 10 g (59% of theory) of 2-(3,3-dimethylbutyl)cyclopentanone.

Step 3: preparation of 2-(3,3-dimethylbutyl)-N-hydroxycyclopentanimine

At 0° C., aq. sodium carbonate solution is added to a solution consisting of 20.0 g of (119 mmol) of 2-(3,3-dimethylbutyl)cyclopentanone and 16.5 g (238 mmol) of hydroxylamine hydrochloride in 200 ml of methanol until the pH is 8. The mixture is then stirred at 50° C. for 15 hours. After the reaction has ended, the mixture is cooled to room temperature and filtered off and the product is concentrated under reduced pressure. The residue is extracted with water/diethyl ether. The org. phase is dried with sodium sulphate and concentrated under reduced pressure. This gives 20.0 g (92% of theory) of an 2-(3,3-dimethylbutyl)-N-hydroxycyclopentanimine.

Step 4: preparation of 2-(3,3-dimethylbutyl)cyclopentanamine hydrochloride (1:1)

3.0 g of Raney nickel are added to a solution consisting of 1.00 g (5.4 mmol) of 2-(3,3-dimethylbutyl)-N-hydroxycyclopentanimine in 10 ml of methanolic ammonia solution, and the mixture is hydrogenated with hydrogen at 20° C. for 18 hours. After the reaction has ended, the mixture is filtered off and the product is concentrated under reduced pressure. The residue is dissolved in diethyl ether, and HCl gas is added. Decanting and washing with diethyl ether gives 0.5 g (45% of theory) of 2-(3,3-dimethylbutyl)cyclopentanamine hydrochloride (1:1).

Step 5: preparation of 3-(difluoromethyl)-N-[2-(3,3-dimethylbutyl)cyclopentyl]-5-fluoro-1-methyl-1H-pyrazole-4-carboxamide As for example 1—step 6, condensation of 1.03 g 2-(3,3-dimethylbutyl)cyclopentanamine hydrochloride over 1.06 g of 3-(difluoromethyl)-5-fluoro-1-methyl-1H-pyrazole-4-carbonyl chloride gives 0.6 (31% of theory) of a syn+anti mixture of 3-(difluoromethyl)-N-[2-(3,3-dimethylbutyl)cyclopentyl]-5-fluoro-1-methyl-1H-pyrazole-4-carboxamide. log P=4.22 (isomer A) and log P=4.28 (isomer B).

PREPARATION EXAMPLE 3

Preparation of 3-(difluoromethyl)-N-[3-(3,3-dimethylbutyl)cyclohexyl]-5-fluoro-1-methyl-1H-pyrazole-4-carboxamide (compound 324)

Step 1: 3-(3,3-dimethylbut-1-yn-1-yl)aniline 1.05 g (1.5 mmol) of bis(triphenylphosphine)palladium(II) chloride and 0.26 g (1.5 mmol) of copper(I) iodide are added to a solution consisting of 5.47 g (25 mmol) of 3-iodoaniline in 40 ml of triethylamine. With ice-cooling, 3.08 g (37.5 mmol) of 3,3-dimethyl-1-butyne are added dropwise such that the temperature remains at 20° C. After the addition has ended, the mixture is stirred at 20° C. for 20 hours. The reaction solution is concentrated under reduced pressure and the residue formed is stirred into 1 l of water. The mixture is then extracted three times with diethyl ether. The combined organic phases are once more washed with water, dried with sodium sulphate and concentrated under reduced pressure. The crude product obtained is purified by silica gel chromatography (mobile phase methylene chloride). This gives 2.70 g (60% of theory) of 3-(3,3-dimethylbut-1-yn-1-yl)aniline having a content of 97% according to HPLC. log P=2.71.

Step 2: 3-(3,3-dimethylbutyl)cyclohexanamine 0.5 g of Ru/C 5% is added to a solution consisting of 1.04 g (0.6 mol) of 3-(3,3-dimethylbut-1-yn-1-yl)aniline in 20 ml of tetrahydrofuran, and the mixture is hydrogenated with 100 bar of hydrogen at 120° C. for 40 hours. After cooling to room temperature, the catalyst is filtered off through kieselguhr and the product is concentrated under reduced pressure. This gives 0.9 g (81% of theory) of 3-(3,3-dimethylbutyl)cyclohexanamine as main component according to MSD-HPLC.

Step 3: preparation of 3-(difluoromethyl)-N-[3-(3,3-dimethylbutyl)cyclohexyl]-5-fluoro-1-methyl-1H-pyrazole-4-carboxamide As for example 1—step 6, condensation of 0.50 g 3-(3,3-dimethylbutyl)cyclohexanamine over 0.638 g of 3-(difluoromethyl)-5-fluoro-1-methyl-1H-pyrazole-4-carbonyl chloride gives 0.65 (54% of theory) of 3-(difluoromethyl)-N-[3-(3,3-dimethylbutyl)cyclohexyl]-5-fluoro-1-methyl-1H-pyrazole-4-carboxamide. log P=4.80.

GENERAL PREPARATION EXAMPLE 4

Thionation of Amide of Formula (I) on Chemspeed™ Apparatus

In a 13 ml Chemspeed™ vial is weighted 0.27 mmole of phosphorous pentasulfide ($P_2S_5$). 3 ml of a 0.18 molar solution of the amide (I) (0.54 mmole) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cartridge (2 g) and eluted twice by 8 ml of dichloromethane. The solvents are removed and the crude thioamide derivative is analyzed by LCMS and NMR. Insufficiently pure compounds are further purified by preparative LCMS.

EXAMPLE A

In Vivo Preventive Test on *Sphaerotheca fuliginea* (Cucumber)

Solvent: 49 parts by weight of N,N-dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table A:

TABLE A

| Example | Efficacy |
|---|---|
| 9 | 95 |
| 70 | 75 |
| 71 | 95 |
| 89 | 88 |
| 129 | 100 |
| 144 | 90 |
| 150 | 83 |
| 153 | 100 |
| 154 | 100 |
| 162 | 95 |
| 163 | 100 |
| 172 | 93 |
| 181 | 100 |
| 182 | 75 |
| 184 | 100 |
| 187 | 100 |
| 196 | 75 |
| 213 | 99 |
| 215 | 100 |
| 216 | 100 |
| 217 | 100 |
| 219 | 100 |
| 221 | 100 |
| 240 | 100 |
| 241 | 100 |
| 242 | 100 |
| 243 | 100 |
| 244 | 100 |
| 247 | 100 |
| 256 | 100 |
| 271 | 98 |
| 288 | 94 |
| 289 | 93 |
| 291 | 73 |
| 296 | 70 |
| 298 | 85 |
| 302 | 98 |
| 306 | 95 |
| 307 | 83 |
| 309 | 98 |
| 310 | 100 |
| 311 | 90 |
| 312 | 90 |
| 314 | 90 |
| 315 | 71 |
| 316 | 98 |
| 318 | 93 |
| 319 | 100 |
| 320 | 100 |
| 322 | 90 |
| 328 | 100 |
| 329 | 100 |
| 330 | 88 |
| 331 | 100 |
| 333 | 100 |
| 337 | 100 |
| 338 | 100 |
| 339 | 100 |
| 340 | 90 |
| 344 | 100 |
| 350 | 100 |
| 357 | 100 |
| 358 | 100 |
| 359 | 100 |
| 360 | 100 |
| 361 | 91 |
| 367 | 100 |
| 368 | 93 |
| 370 | 100 |
| 372 | 100 |
| 374 | 100 |
| 381 | 95 |

Under the same conditions, total protection is observed at a dose of 500 ppm of active ingredient with compound 240, whereas poor protection (less than 25%) is observed with the des-fluoro analogue compound CMP1 as in table A2.

TABLE A2

| Example | dose (ppm) | Efficacy |
|---|---|---|
| 240 from this invention | 500 | 100 |
| compound CMP1 | 500 | 23 |

The des-fluoro analogue compound CMP1 corresponds to N-cyclopropyl-3-(difluoromethyl)-1-methyl-N-[(2-phenyl-cyclohexyl)methyl]-1H-pyrazole-4-carboxamide.

These results show that the compounds according to the invention have a much better biological activity than the structurally closest compounds.

Under the same conditions, total protection is observed at a dose of 500 ppm of active ingredient with compound 256, whereas poor protection (less than 15%) is observed with the des-fluoro analogues compound CMP2 and compound CMP3 as in table A3.

TABLE A3

| Example | dose (ppm) | Efficacy |
|---|---|---|
| 256 from this invention | 500 | 100 |
| compound CMP2 | 500 | 10 |
| compound CMP3 | 500 | 0 |

The des-fluoro analogue compound CMP2 corresponds to N-cyclopropyl-5-fluoro-1,3-dimethyl-N-(3-phenylcyclo-hexyl)-1H-pyrazole-4-carboxamide and the des-fluoro analogue compound CMP3 corresponds to N-cyclopropyl-3-(difluoromethyl)-1-methyl-N-(3-phenylcyclohexyl)-1H-pyrazole-4-carboxamide.

These results show that the compounds according to the invention have a much better biological activity than the structurally closest compounds.

Under the same conditions, total protection is observed at a dose of 500 ppm of active ingredient with compound 374, whereas no protection is observed with the des-fluoro analogues compound CMP4 and compound CMP5 as in table A4.

TABLE A4

| Example | dose (ppm) | Efficacy |
|---|---|---|
| 374 from this invention | 500 | 100 |
| compound CMP4 | 500 | 0 |
| compound CMP5 | 500 | 0 |

The des-fluoro analogue compound CMP4 corresponds to N-[1,1'-bi(cyclohexyl)-2-yl]-5-fluoro-1,3-dimethyl-1H-pyrazole-4-carboxamide and the des-fluoro analogue compound CMP5 corresponds to N-[1,1'-bi(cyclohexyl)-2-yl]-3-(difluoromethyl)-1-methyl-1H-pyrazole-4-carboxamide.

These results show that the compounds according to the invention have a much better biological activity than the structurally closest compounds.

EXAMPLE B

In Vivo Preventive Test on *Alternaria solani* (Tomato)

Solvent: 49 parts by weight of N,N-dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

Under these conditions, good (at least 70%) to total protection is observed at a dose of 500 ppm of active ingredient with the following compounds from table B:

TABLE B

| Example | Efficacy |
|---|---|
| 5 | 80 |
| 6 | 95 |
| 9 | 90 |
| 10 | 90 |
| 11 | 95 |
| 12 | 95 |
| 13 | 90 |
| 14 | 90 |
| 16 | 90 |
| 17 | 95 |
| 19 | 95 |
| 21 | 90 |
| 22 | 95 |
| 29 | 80 |
| 32 | 95 |
| 33 | 95 |
| 34 | 90 |
| 36 | 70 |
| 37 | 80 |
| 38 | 80 |
| 40 | 95 |
| 42 | 70 |
| 44 | 100 |
| 45 | 95 |
| 46 | 100 |
| 47 | 80 |
| 48 | 90 |
| 63 | 100 |
| 66 | 95 |
| 67 | 70 |
| 69 | 80 |
| 70 | 95 |
| 71 | 95 |
| 74 | 95 |
| 81 | 90 |
| 82 | 95 |
| 83 | 95 |
| 84 | 95 |
| 89 | 80 |
| 115 | 90 |
| 116 | 90 |
| 121 | 90 |
| 122 | 100 |
| 123 | 95 |
| 124 | 95 |
| 125 | 95 |
| 126 | 90 |
| 127 | 90 |
| 128 | 95 |
| 129 | 100 |
| 130 | 95 |
| 131 | 95 |
| 132 | 100 |
| 136 | 80 |
| 137 | 95 |
| 142 | 100 |
| 143 | 100 |
| 144 | 100 |
| 145 | 70 |
| 148 | 95 |
| 149 | 90 |
| 150 | 80 |
| 151 | 90 |
| 154 | 100 |

TABLE B-continued

| Example | Efficacy |
|---|---|
| 156 | 80 |
| 157 | 80 |
| 158 | 80 |
| 159 | 90 |
| 163 | 100 |
| 164 | 95 |
| 165 | 90 |
| 166 | 100 |
| 167 | 100 |
| 168 | 90 |
| 169 | 90 |
| 170 | 90 |
| 171 | 95 |
| 172 | 100 |
| 173 | 90 |
| 174 | 100 |
| 175 | 95 |
| 176 | 80 |
| 177 | 100 |
| 178 | 95 |
| 180 | 90 |
| 181 | 100 |
| 182 | 95 |
| 183 | 95 |
| 184 | 90 |
| 188 | 100 |
| 189 | 90 |
| 190 | 90 |
| 191 | 95 |
| 192 | 95 |
| 193 | 95 |
| 194 | 70 |
| 195 | 95 |
| 196 | 95 |
| 210 | 70 |
| 213 | 100 |
| 214 | 80 |
| 215 | 95 |
| 218 | 90 |
| 219 | 95 |
| 220 | 95 |
| 221 | 100 |
| 222 | 90 |
| 224 | 70 |
| 225 | 95 |
| 240 | 100 |
| 241 | 100 |
| 242 | 100 |
| 243 | 100 |
| 244 | 100 |
| 245 | 90 |
| 256 | 93 |
| 259 | 90 |
| 287 | 95 |
| 288 | 100 |
| 289 | 95 |
| 290 | 95 |
| 291 | 100 |
| 294 | 95 |
| 295 | 100 |
| 296 | 80 |
| 297 | 100 |
| 298 | 100 |
| 299 | 95 |
| 300 | 90 |
| 301 | 100 |
| 302 | 95 |
| 303 | 80 |
| 306 | 100 |
| 307 | 100 |
| 309 | 100 |
| 310 | 100 |
| 311 | 100 |
| 312 | 95 |
| 313 | 80 |
| 314 | 95 |
| 315 | 100 |
| 316 | 90 |
| 318 | 90 |
| 319 | 100 |
| 320 | 100 |
| 322 | 90 |
| 324 | 90 |
| 325 | 95 |
| 328 | 95 |
| 329 | 100 |
| 330 | 95 |
| 331 | 100 |
| 333 | 100 |
| 337 | 100 |
| 338 | 100 |
| 339 | 100 |
| 340 | 100 |
| 341 | 80 |
| 343 | 95 |
| 344 | 100 |
| 349 | 95 |
| 350 | 90 |
| 353 | 95 |
| 357 | 100 |
| 358 | 100 |
| 359 | 95 |
| 360 | 95 |
| 361 | 95 |
| 364 | 95 |
| 366 | 90 |
| 367 | 90 |
| 368 | 80 |
| 370 | 100 |
| 372 | 95 |
| 378 | 100 |
| 379 | 95 |
| 380 | 95 |
| 381 | 100 |

Under the same conditions, high protection (at least 90%) is observed at a dose of 500 ppm of active ingredient with compound 13 and compound 14, whereas poor protection (less than 10%) is observed with the des-halogeno analogue compound CMP6 as in table B2.

TABLE B2

| Example | dose (ppm) | Efficacy |
|---|---|---|
| 13 from this invention | 500 | 90 |
| 14 from this invention | 500 | 90 |
| compound CMP6 | 500 | 10 |

The des-halogeno analogue compound CMP6 corresponds to 3-(difluoromethyl)-1-methyl-N-(1-phenoxypropan-2-yl)-1H-pyrazole-4-carboxamide.

These results show that the compounds according to the invention have a much better biological activity than the structurally closest compounds.

Under the same conditions, excellent protection (at least 95%) is observed at a dose of 500 ppm and 100 ppm of active ingredient with compound 349, whereas moderate protection (less than 60%) is observed with the des-fluoro analogue compound CMP7 as in table B3.

TABLE B3

| Example | dose (ppm) | Efficacy |
|---|---|---|
| 349 from this invention | 500 | 95 |
|  | 100 | 95 |
| compound CMP7 | 500 | 57 |
|  | 100 | 43 |

The des-fluoro analogue compound CMP7 corresponds to N-(2-tert-butylcyclohexyl)-3-(difluoromethyl)-1-methyl-1H-pyrazole-4-carboxamide.

These results show that the compounds according to the invention have a much better biological activity than the structurally closest compounds.

EXAMPLE C

In Vivo Preventive Test on *Pyrenophora teres* (Barley)

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

Under these conditions, good (at least 70%) to total protection is observed at a dose of 500 ppm of active ingredient with the following compounds from table C:

TABLE C

| Example | Efficacy |
| --- | --- |
| 6 | 70 |
| 9 | 100 |
| 10 | 95 |
| 11 | 100 |
| 12 | 100 |
| 13 | 94 |
| 14 | 95 |
| 16 | 90 |
| 19 | 89 |
| 21 | 80 |
| 28 | 90 |
| 29 | 100 |
| 32 | 70 |
| 33 | 95 |
| 35 | 70 |
| 36 | 100 |
| 37 | 100 |
| 38 | 80 |
| 40 | 80 |
| 42 | 94 |
| 43 | 89 |
| 46 | 100 |
| 62 | 80 |
| 63 | 100 |
| 66 | 100 |
| 67 | 100 |
| 68 | 80 |
| 70 | 100 |
| 71 | 100 |
| 83 | 95 |
| 84 | 95 |
| 89 | 100 |
| 115 | 100 |
| 116 | 100 |

TABLE C-continued

| Example | Efficacy |
| --- | --- |
| 117 | 78 |
| 121 | 100 |
| 122 | 100 |
| 123 | 100 |
| 124 | 90 |
| 125 | 100 |
| 126 | 100 |
| 127 | 100 |
| 128 | 100 |
| 129 | 100 |
| 130 | 95 |
| 131 | 100 |
| 132 | 100 |
| 135 | 90 |
| 136 | 95 |
| 137 | 89 |
| 139 | 90 |
| 141 | 90 |
| 142 | 95 |
| 143 | 100 |
| 144 | 100 |
| 145 | 70 |
| 147 | 100 |
| 148 | 95 |
| 149 | 95 |
| 150 | 100 |
| 151 | 94 |
| 153 | 100 |
| 154 | 100 |
| 155 | 100 |
| 156 | 95 |
| 157 | 100 |
| 158 | 95 |
| 161 | 100 |
| 162 | 95 |
| 163 | 100 |
| 164 | 100 |
| 165 | 100 |
| 166 | 100 |
| 167 | 80 |
| 168 | 100 |
| 171 | 100 |
| 172 | 100 |
| 173 | 78 |
| 174 | 95 |
| 175 | 95 |
| 176 | 95 |
| 177 | 100 |
| 178 | 100 |
| 179 | 100 |
| 180 | 100 |
| 181 | 100 |
| 182 | 100 |
| 183 | 100 |
| 184 | 100 |
| 187 | 100 |
| 188 | 100 |
| 189 | 100 |
| 190 | 95 |
| 191 | 100 |
| 192 | 100 |
| 193 | 94 |
| 195 | 95 |
| 196 | 100 |
| 202 | 80 |
| 210 | 90 |
| 213 | 100 |
| 214 | 100 |
| 215 | 100 |
| 216 | 100 |
| 217 | 100 |
| 218 | 100 |
| 219 | 100 |
| 220 | 100 |
| 221 | 95 |
| 222 | 90 |
| 240 | 100 |
| 241 | 100 |

TABLE C-continued

| Example | Efficacy |
|---|---|
| 242 | 100 |
| 243 | 100 |
| 244 | 95 |
| 245 | 78 |
| 247 | 100 |
| 256 | 100 |
| 258 | 89 |
| 259 | 78 |
| 260 | 70 |
| 271 | 95 |
| 287 | 100 |
| 288 | 100 |
| 289 | 100 |
| 290 | 100 |
| 291 | 100 |
| 294 | 95 |
| 295 | 100 |
| 296 | 100 |
| 297 | 100 |
| 298 | 100 |
| 299 | 100 |
| 300 | 100 |
| 301 | 100 |
| 302 | 100 |
| 303 | 100 |
| 306 | 100 |
| 307 | 100 |
| 309 | 100 |
| 310 | 100 |
| 311 | 100 |
| 312 | 100 |
| 313 | 100 |
| 314 | 100 |
| 315 | 100 |
| 316 | 100 |
| 318 | 100 |
| 319 | 100 |
| 320 | 95 |
| 322 | 100 |
| 324 | 94 |
| 326 | 100 |
| 328 | 95 |
| 329 | 100 |
| 330 | 100 |
| 331 | 95 |
| 333 | 100 |
| 337 | 100 |
| 338 | 100 |
| 339 | 94 |
| 340 | 100 |
| 343 | 100 |
| 344 | 100 |
| 349 | 95 |
| 350 | 100 |
| 353 | 95 |
| 357 | 100 |
| 358 | 100 |
| 359 | 100 |
| 360 | 95 |
| 361 | 95 |
| 364 | 80 |
| 367 | 100 |
| 368 | 95 |
| 370 | 100 |
| 372 | 100 |
| 378 | 100 |
| 379 | 100 |
| 380 | 100 |
| 381 | 100 |

Under the same conditions, total protection is observed at a dose of 500 ppm and 100 ppm of active ingredient with compound 326, whereas poor protection (less than 10%) to no protection is observed with the des-halogeno analogue compound CMP8 as in table C2.

TABLE C2

| Example | dose (ppm) | Efficacy |
|---|---|---|
| 326 from this invention | 500 | 100 |
|  | 100 | 100 |
| compound CMP8 | 500 | 20 |
|  | 100 | 0 |

The des-fluoro analogue compound CMP8 corresponds to N-(2-hexylcyclohexyl)-1-methyl-3-(trifluoromethyl)-1H-pyrazole-4-carboxamide.

These results show that the compounds according to the invention have a much better biological activity than the structurally closest compounds.

EXAMPLE D

In Vivo Preventive Test on *Venturia inaequalis* (Apple Scab)

Solvent: 24.5 parts by weight of acetone
24.5 parts by weight of N,N-dimethylacetamide
Emulsifier: 1 part by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

Under these conditions, good (at least 70%) to total protection is observed at a dose of 100 ppm of active ingredient with the following compounds from table D:

TABLE D

| Example | Efficacy |
|---|---|
| 9 | 100 |
| 129 | 100 |
| 181 | 100 |
| 184 | 100 |
| 187 | 100 |
| 217 | 100 |
| 218 | 100 |
| 221 | 100 |
| 240 | 100 |
| 241 | 100 |
| 242 | 100 |
| 243 | 100 |
| 244 | 100 |
| 256 | 100 |
| 288 | 100 |
| 306 | 99 |
| 307 | 100 |
| 310 | 100 |
| 311 | 100 |
| 312 | 99 |
| 314 | 98 |
| 315 | 100 |

TABLE D-continued

| Example | Efficacy |
|---------|----------|
| 316 | 100 |
| 320 | 100 |
| 329 | 100 |
| 331 | 100 |
| 333 | 99 |
| 334 | 100 |
| 335 | 100 |
| 337 | 74 |
| 338 | 100 |
| 339 | 100 |
| 343 | 97 |
| 353 | 99 |
| 354 | 100 |
| 355 | 99 |
| 357 | 100 |
| 358 | 100 |
| 359 | 99 |
| 360 | 100 |
| 361 | 88 |
| 378 | 100 |

EXAMPLE E

In Vivo Preventive Test on *Septoria tritici* (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table E:

TABLE E

| Example | Efficacy |
|---------|----------|
| 9 | 100 |
| 129 | 80 |
| 161 | 80 |
| 162 | 90 |
| 181 | 100 |
| 184 | 100 |
| 187 | 100 |
| 213 | 93 |
| 215 | 90 |
| 216 | 100 |
| 217 | 100 |

TABLE E-continued

| Example | Efficacy |
|---------|----------|
| 218 | 86 |
| 221 | 100 |
| 240 | 100 |
| 241 | 100 |
| 243 | 100 |
| 244 | 100 |
| 256 | 100 |
| 271 | 88 |
| 288 | 90 |
| 311 | 93 |
| 315 | 100 |
| 319 | 100 |
| 326 | 78 |
| 329 | 100 |
| 330 | 78 |
| 331 | 100 |
| 333 | 100 |
| 334 | 100 |
| 337 | 78 |
| 338 | 100 |
| 339 | 100 |
| 343 | 100 |
| 344 | 94 |
| 353 | 80 |
| 357 | 100 |
| 358 | 80 |
| 359 | 100 |
| 360 | 90 |
| 361 | 100 |

EXAMPLE F

In Vivo Preventive Test on *Blumeria graminis* (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of *Blumeria graminis* fsp. *hordei*.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table F:

TABLE F

| Example | Efficacy |
|---------|----------|
| 9 | 100 |
| 129 | 100 |
| 161 | 100 |
| 162 | 100 |
| 181 | 100 |
| 184 | 100 |
| 187 | 100 |

TABLE F-continued

| Example | Efficacy |
| --- | --- |
| 213 | 100 |
| 215 | 100 |
| 217 | 100 |
| 221 | 100 |
| 240 | 100 |
| 243 | 100 |
| 244 | 100 |
| 271 | 78 |
| 288 | 100 |
| 306 | 100 |
| 311 | 100 |
| 315 | 100 |
| 319 | 100 |
| 329 | 100 |
| 330 | 100 |
| 331 | 100 |
| 333 | 100 |
| 334 | 90 |
| 335 | 70 |
| 338 | 100 |
| 339 | 100 |
| 343 | 94 |
| 344 | 100 |
| 353 | 90 |
| 354 | 100 |
| 355 | 80 |
| 357 | 100 |
| 358 | 100 |
| 359 | 94 |
| 360 | 100 |

EXAMPLE G

In Vivo Preventive Test on *Fusarium nivale* (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table G:

TABLE G

| Example | Efficacy |
| --- | --- |
| 9 | 100 |
| 184 | 100 |
| 213 | 93 |
| 215 | 71 |
| 216 | 93 |
| 217 | 100 |
| 218 | 100 |
| 240 | 71 |
| 256 | 100 |
| 306 | 100 |
| 311 | 100 |
| 315 | 100 |
| 319 | 100 |
| 324 | 100 |
| 326 | 92 |
| 329 | 100 |
| 330 | 100 |
| 331 | 100 |
| 333 | 100 |
| 334 | 93 |
| 335 | 86 |
| 338 | 100 |
| 339 | 100 |
| 343 | 100 |
| 344 | 100 |
| 353 | 100 |
| 354 | 100 |
| 355 | 100 |
| 357 | 100 |
| 358 | 100 |
| 359 | 100 |
| 360 | 86 |

EXAMPLE H

In Vivo Preventive Test on *Fusarium graminearum* (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium graminearum*.

The plants are placed in the greenhouse under a translucent incubation cabinet at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

Under these conditions, high (at least 85%) to total protection is observed at a dose of 500 ppm of active ingredient with the following compounds from table H:

TABLE H

| Example | Efficacy |
| --- | --- |
| 129 | 100 |
| 161 | 86 |
| 162 | 100 |
| 187 | 100 |
| 221 | 100 |
| 243 | 100 |

TABLE H-continued

| Example | Efficacy |
|---|---|
| 244 | 100 |
| 271 | 93 |
| 288 | 100 |

EXAMPLE I

In Vivo Preventive Test on *Leptosphaeria nodorum* (Wheat)

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%.

The test is evaluated 7-9 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table I:

TABLE I

| Example | Efficacy |
|---|---|
| 9 | 100 |
| 29 | 80 |
| 37 | 90 |
| 129 | 100 |
| 130 | 90 |
| 131 | 80 |
| 157 | 80 |
| 161 | 90 |
| 162 | 90 |
| 168 | 90 |
| 181 | 95 |
| 184 | 95 |
| 187 | 90 |
| 213 | 95 |
| 217 | 78 |
| 219 | 90 |
| 220 | 90 |
| 221 | 95 |
| 240 | 70 |
| 241 | 80 |
| 243 | 100 |
| 244 | 95 |
| 245 | 90 |
| 247 | 95 |
| 256 | 95 |
| 271 | 90 |
| 287 | 95 |
| 288 | 100 |
| 289 | 95 |
| 290 | 80 |
| 291 | 100 |
| 293 | 94 |
| 294 | 70 |

TABLE I-continued

| Example | Efficacy |
|---|---|
| 295 | 100 |
| 296 | 95 |
| 298 | 95 |
| 299 | 95 |
| 312 | 95 |
| 314 | 80 |
| 316 | 80 |
| 318 | 70 |
| 322 | 90 |
| 328 | 80 |
| 329 | 90 |
| 333 | 80 |
| 339 | 70 |
| 339 | 94 |
| 344 | 90 |
| 365 | 90 |
| 370 | 90 |
| 372 | 94 |

Under the same conditions, hioh protection (at least 90%) is observed at a dose of 500 ppm of active ingredient with compound 220 and compound 221, whereas poor protection (less than 10%) is observed with the compound of example E-12 disclosed in patent application WO-2008/101976 as in table 12.

TABLE I2

| Example | dose (ppm) | Efficacy |
|---|---|---|
| 220 from this invention | 500 | 90 |
| 221 from this invention | 500 | 95 |
| E-12 from WO-2008/101976 | 500 | 10 |

Example E-12 disclosed in international patent WO-2008/101976 corresponds to N-cyclopropyl-5-fluoro-1,3-dimethyl-N-{4-[2-(trifluoromethyl)phenyl]butan-2-yl}-1H-pyrazole-4-carboxamide.

These results show that the compounds according to the invention have a much better biological activity than the structurally closest compounds disclosed in WO-2008/101976.

EXAMPLE J

In Vivo Preventive Test on *Uromvces appendiculatus* (Beans)

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

Under these conditions, good (at least 70%) to total protection is observed at a dose of 100 ppm of active ingredient with the following compounds from table J:

TABLE J

| Example | Efficacy |
|---|---|
| 9 | 94 |
| 129 | 99 |
| 181 | 78 |
| 184 | 100 |
| 187 | 95 |
| 218 | 95 |
| 221 | 100 |
| 240 | 100 |
| 241 | 100 |
| 242 | 100 |
| 243 | 98 |
| 244 | 100 |
| 256 | 100 |
| 288 | 100 |
| 306 | 70 |
| 307 | 100 |
| 310 | 100 |
| 311 | 100 |
| 312 | 100 |
| 313 | 88 |
| 314 | 85 |
| 315 | 100 |
| 316 | 100 |
| 320 | 99 |
| 329 | 100 |
| 331 | 100 |
| 334 | 100 |
| 335 | 100 |
| 337 | 86 |
| 339 | 100 |
| 354 | 100 |
| 355 | 100 |
| 357 | 100 |
| 359 | 100 |
| 376 | 94 |
| 378 | 100 |

EXAMPLE K

In Vivo Preventive Test on *Puccinia triticina* (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has been dried, the plants are sprayed with a spore suspension of *Puccinia triticina*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

Under these conditions, good (at least 75%) to total protection is observed at a dose of 500 ppm of active ingredient with the following compounds from table K:

TABLE K

| Example | Efficacy |
|---|---|
| 129 | 70 |
| 130 | 70 |
| 153 | 95 |
| 154 | 70 |
| 155 | 90 |
| 161 | 90 |
| 162 | 80 |
| 163 | 80 |
| 166 | 78 |
| 167 | 70 |
| 184 | 90 |
| 187 | 95 |
| 213 | 90 |
| 216 | 78 |
| 217 | 89 |
| 220 | 90 |
| 221 | 100 |
| 240 | 95 |
| 241 | 100 |
| 242 | 100 |
| 243 | 100 |
| 244 | 100 |
| 245 | 70 |
| 246 | 95 |
| 247 | 100 |
| 256 | 95 |
| 271 | 89 |
| 288 | 95 |
| 306 | 95 |
| 307 | 80 |
| 311 | 100 |
| 312 | 100 |
| 315 | 95 |
| 316 | 100 |
| 319 | 80 |
| 320 | 70 |
| 322 | 95 |
| 324 | 100 |
| 326 | 100 |
| 329 | 100 |
| 330 | 80 |
| 331 | 90 |
| 333 | 90 |
| 335 | 100 |
| 337 | 70 |
| 338 | 100 |
| 339 | 100 |
| 343 | 70 |
| 344 | 100 |
| 353 | 70 |
| 354 | 100 |
| 357 | 100 |
| 358 | 100 |
| 359 | 100 |
| 360 | 100 |
| 361 | 90 |
| 370 | 90 |
| 372 | 100 |
| 374 | 100 |

Under the same conditions, moderate protection (at least 70%) is observed at a dose of 500 ppm of active ingredient with compound 129 and compound 130, whereas no protection is observed with the compound of example E-13 disclosed in patent application WO-2008/101976 as in table K2.

TABLE K2

| Example | dose (ppm) | Efficacy |
|---|---|---|
| 129 from this invention | 500 | 70 |
| 130 from this invention | 500 | 70 |
| E-13 from WO-2008/101976 | 500 | 0 |

Example E-13 disclosed in international patent WO-2008/101976 corresponds to N-cyclopropyl-N-[4-(3,4-dichlorophenyl)butan-2-yl]-5-fluoro-1,3-dimethyl-1H-pyrazole-4-carboxamide.

These results show that the compounds according to the invention have a much better biological activity than the structurally closest compounds disclosed in WO-2008/101976.

Under the same conditions, excellent protection (at least 95%) is observed at a dose of 500 ppm of active ingredient with compound 187, whereas weak protection (less than 30%) is observed with the compound of example 18 disclosed in patent application WO-2010/012795 as in table K3.

TABLE K3

| Example | dose (ppm) | Efficacy |
| --- | --- | --- |
| 187 from this invention | 500 | 95 |
| 18 from WO-2010/012795 | 500 | 30 |

Example 18 disclosed in international patent WO-2010/012795 corresponds to N-cyclopropyl-N-[1-(2,4-dichlorophenoxy)propan-2-yl]-3-(difluoromethyl)-1-methyl-1H-pyrazole-4-carboxamide.

These results show that the compounds according to the invention have a much better biological activity than the structurally closest compounds disclosed in WO-2010/012795.

Under the same conditions, total protection to good protection (at least 80%) is observed at a dose of 500 ppm and 100 ppm of active ingredient with compound 243, whereas moderate protection (less than 60%) to no protection is observed with the compound of example 16 disclosed in patent application WO-2010/094666 as in table K4.

TABLE K4

| Example | dose (ppm) | Efficacy |
| --- | --- | --- |
| 243 from this invention | 500 | 100 |
| | 100 | 80 |
| 16 from WO-2010/094666 | 500 | 60 |
| | 100 | 0 |

Example 16 disclosed in international patent WO-2010/094666 corresponds to N-(2-benzylcyclohexyl)-N-cyclopropyl-3-(difluoromethyl)-1-methyl-1H-pyrazole-4-carboxamide.

These results show that the compounds according to the invention have a much better biological activity than the structurally closest compounds disclosed in WO-2010/012795.

Under the same conditions, excellent protection (at least 95%) is observed at a dose of 500 ppm of active ingredient with compound 256, whereas no protection is observed with the des-fluoro analogues compound CMP2 and compound CMP3 as in table K5.

TABLE K5

| Example | dose (ppm) | Efficacy |
| --- | --- | --- |
| 256 from this invention | 500 | 95 |
| compound CMP2 | 500 | 0 |
| compound CMP3 | 500 | 0 |

The des-fluoro analogue compound CMP2 corresponds to N-cyclopropyl-5-fluoro-1,3-dimethyl-N-(3-phenylcyclohexyl)-1H-pyrazole-4-carboxamide and the des-fluoro analogue compound CMP3 corresponds to N-cyclopropyl-3-(difluoromethyl)-1-methyl-N-(3-phenylcyclohexyl)-1H-pyrazole-4-carboxamide.

These results show that the compounds according to the invention have a much better biological activity than the structurally closest compounds.

Under the same conditions, total protection is observed at a dose of 500 ppm of active ingredient with compound 374, whereas no protection is observed with the des-fluoro analogues compound CMP4 and compound CMP5 as in table K6.

TABLE K6

| Example | dose (ppm) | Efficacy |
| --- | --- | --- |
| 374 from this invention | 500 | 100 |
| compound CMP4 | 500 | 0 |
| compound CMP5 | 500 | 0 |

The des-fluoro analogue compound CMP4 corresponds to N-[1,1'-bi(cyclohexyl)-2-yl]-5-fluoro-1,3-dimethyl-1H-pyrazole-4-carboxamide and the des-fluoro analogue compound CMP5 corresponds to N-[1,1'-bi(cyclohexyl)-2-yl]-3-(difluoromethyl)-1-methyl-1H-pyrazole-4-carboxamide.

These results show that the compounds according to the invention have a much better biological activity than the structurally closest compounds.

EXAMPLE L

In Vivo Preventive Test on *Botrytis cinerea* (Beans)

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound. After the spray coating has dried on, 2 small pieces of agar covered with growth of *Botrytis cinerea* are placed on each leaf. The inoculated plants are placed in a darkened chamber at 20° C. and a relative atmospheric humidity of 100%.

2 days after the inoculation, the size of the lesions on the leaves is evaluated. 0% means an efficacy which corresponds to that of the untreated control, while an efficacy of 100% means that no disease is observed. Under these conditions, good (at least 70%) to total protection is observed at a dose of 500 ppm of active ingredient with the following compounds from table L:

TABLE L

| Example | Efficacy |
| --- | --- |
| 9 | 100 |
| 10 | 85 |
| 213 | 86 |
| 240 | 95 |
| 241 | 99 |
| 242 | 95 |
| 243 | 90 |
| 244 | 88 |
| 256 | 93 |
| 288 | 100 |

TABLE L-continued

| Example | Efficacy |
|---|---|
| 289 | 100 |
| 291 | 100 |
| 302 | 93 |
| 306 | 94 |
| 315 | 70 |
| 319 | 73 |
| 329 | 99 |
| 337 | 93 |
| 344 | 100 |
| 366 | 84 |
| 370 | 100 |
| 372 | 91 |
| 378 | 96 |
| 381 | 88 |

Under the same conditions, excellent protection (at least 95%) is observed at a dose of 500 ppm of active ingredient with compound 240, whereas poor protection (less than 15%) is observed with the des-fluoro analogues compound CMP1 and compound CMP9 as in table L2.

TABLE L2

| Example | dose (ppm) | Efficacy |
|---|---|---|
| 240 from this invention | 500 | 95 |
| compound CMP1 | 500 | 0 |
| compound CMP9 | 500 | 13 |

The des-fluoro analogue compound CMP1 corresponds to N-cyclopropyl-3-(difluoromethyl)-1-methyl-N-[(2-phenylcyclohexyl)methyl]-1H-pyrazole-4-carboxamide and the des-fluoro analogue compound CMP9 corresponds to N-cyclopropyl-5-fluoro-1,3-dimethyl-N-[(2-phenylcyclohexyl)methyl]-1H-pyrazole-4-carboxamide.

These results show that the compounds according to the invention have a much better biological activity than the structurally closest compounds.

Under the same conditions, high protection (at least 90%) is observed at a dose of 500 ppm of active ingredient with compound 243, whereas poor protection (less than 30%) is observed with the compound of example 16 disclosed in patent application WO-2010/094666 as in table L3.

TABLE L3

| Example | dose (ppm) | Efficacy |
|---|---|---|
| 243 from this invention | 500 | 90 |
| 16 from WO-2010/094666 | 500 | 29 |

Example 16 disclosed in international patent WO-2010/094666 corresponds to N-(2-benzylcyclohexyl)-N-cyclopropyl-3-(difluoromethyl)-1-methyl-1H-pyrazole-4-carboxamide.

These results show that the compounds according to the invention have a much better biological activity than the structurally closest compounds disclosed in WO-2010/012795.

Under the same conditions, good protection (at least 85%) is observed at a dose of 500 ppm of active ingredient with compound 244, whereas poor protection (less than 30%) is observed with the des-fluoro analogue compound CMP10 as in table L4.

TABLE L4

| Example | dose (ppm) | Efficacy |
|---|---|---|
| 244 from this invention | 500 | 88 |
| compound CMP10 | 500 | 29 |

The des-fluoro analogue compound CMP10 corresponds to N-cyclopropyl-5-fluoro-1,3-dimethyl-N-(2-phenoxycyclohexyl)-1H-pyrazole-4-carboxamide.

These results show that the compounds according to the invention have a much better biological activity than the structurally closest compounds.

Under the same conditions, high protection (at least 90%) is observed at a dose of 500 ppm of active ingredient with compound 256, whereas poor protection (less than 5%) is observed with the des-fluoro analogues compound CMP2 and compound CMP3 as in table L5.

TABLE L5

| Example | dose (ppm) | Efficacy |
|---|---|---|
| 256 from this invention | 500 | 93 |
| compound CMP2 | 500 | 5 |
| compound CMP3 | 500 | 0 |

The des-fluoro analogue compound CMP2 corresponds to N-cyclopropyl-5-fluoro-1,3-dimethyl-N-(3-phenylcyclohexyl)-1H-pyrazole-4-carboxamide and the des-fluoro analogue compound CMP3 corresponds to N-cyclopropyl-3-(difluoromethyl)-1-methyl-N-(3-phenylcyclohexyl)-1H-pyrazole-4-carboxamide.

These results show that the compounds according to the invention have a much better biological activity than the structurally closest compounds.

EXAMPLE M

In Vivo Protective Test on *Cochliobolus miyabeanus* (Rice)

Solvent: 28.5 parts by weight of acetone

Emulsifier: 1.5 part by weight of polyoxyethylene alkyl phenyl ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of rice brown spot (*Cochliobolus miyabeanus*). The plants are then placed in an incubator at approximately 25° C. and a relative atmospheric humidity of approximately 100% for 1 day.

The test is evaluated 4 days after the inoculation. 0% means an efficacy which corresponds to that of the control, while an efficacy of 100% means that no disease is observed.

Under these conditions, high (at least 85%) protection is observed at a dose of 250 ppm of active ingredient with the following compounds from table M:

TABLE M

| Example | Efficacy |
|---|---|
| 215 | 98 |
| 216 | 90 |
| 217 | 98 |
| 306 | 95 |
| 311 | 97 |
| 315 | 97 |
| 324 | 97 |
| 329 | 98 |
| 330 | 85 |
| 338 | 96 |
| 339 | 92 |
| 344 | 95 |
| 357 | 93 |
| 360 | 94 |

EXAMPLE N

In Vivo Protective Test on *Phakopsora pachyrhizi* (Soybeans)

Solvent: 28.5 parts by weight of acetone
Emulsifier: 1.5 part by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. One day after spraying, the plants are inoculated with an aqueous spore suspension of the causal agent of soybean rust (*Phakopsora pachyrhizi*). The plants are then placed in a greenhouse at approximately 20° C. and a relative atmospheric humidity of approximately 80%.

The test is evaluated 11 days after the inoculation. 0% means an efficacy which corresponds to that of the control, while an efficacy of 100% means that no disease is observed.

Under these conditions, high (at least 85%) to total protection is observed at a dose of 250 ppm of active ingredient with the following compounds from table M:

TABLE N

| Example | Efficacy |
|---|---|
| 221 | 80 |
| 240 | 85 |
| 241 | 99 |
| 242 | 99 |
| 244 | 98 |
| 256 | 85 |
| 311 | 98 |
| 333 | 97 |
| 334 | 100 |
| 338 | 98 |
| 339 | 98 |
| 353 | 85 |
| 357 | 85 |
| 358 | 95 |

EXAMPLE O

In Vivo Protective Test on *Pyricularia oryzae* (Rice)

Solvent: 28.5 parts by weight of acetone
Emulsifier: 1.5 part by weight of polyoxyethylene alkyl phenyl ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after spraying, the plants are inoculated with an aqueous spore suspension of the causal agent of rice blast (*Pyricularia oryzae*). The plants are then placed in an incubator at approximately 25° C. and a relative atmospheric humidity of approximately 100% for 1 day.

The test is evaluated 5 days after the inoculation. 0% means an efficacy which corresponds to that of the control, while an efficacy of 100% means that no disease is observed.

Under these conditions, high (at least 80%) to total protection is observed at a dose of 250 ppm of active ingredient with the following compounds from table O:

TABLE O

| Example | Efficacy |
|---|---|
| 215 | 98 |
| 216 | 95 |
| 217 | 97 |
| 306 | 95 |
| 311 | 96 |
| 315 | 95 |
| 329 | 98 |
| 330 | 80 |
| 338 | 97 |
| 339 | 98 |
| 344 | 95 |
| 357 | 97 |

EXAMPLE P

Inhibition of Aflatoxines Produced by *Aspergillus parasiticus*

Compounds were tested in microtiter plates (96 well black flat and transparent bottom) in Aflatoxin-inducing liquid media (20 g sucrose, yeast extract 4 g, $KH_2PO_4$ 1 g, and $MgSO_4$ $7H_2O$ 0.5 g per liter), supplemented with 20 mM of Cavasol (hydroxypropyl-beta-cyclodextrin) and containing 1% of DMSO. The assay is started by inoculating the medium with a concentrated spore suspension of *Aspergillus parasiticus* at a final concentration of 1000 spores/ml.

The plate was covered and incubated at 20° C. for 7 days. After 7 days of culture, OD measurement at $OD_{620nm}$ with multiple read per well (circle: 4×4) was taken with an Infinite 1000 (Tecan) to calculate the growth inhibition. In the same time bottom fluorescence measurement at $EM_{360nm}$ and $EX_{426nm}$ with multiple read per well (square: 3×3) was taken to calculate inhibition of aflatoxin formation.

Compounds from table O show good (at least 80%) to total inhibition of aflatoxines production at 50 µM. Growth inhibition of *Fusarium graminearum* of these examples vary from 67 to 100% at 50 µM.

TABLE P

| Example | % Inhibition of Aflatoxin at 50 µM | % Inhibition of fungal growth at 50 µM |
|---|---|---|
| 70 | 97 | 78 |
| 71 | 100 | 83 |
| 76 | 100 | 83 |
| 77 | 100 | 98 |

TABLE P-continued

| Example | % Inhibition of Aflatoxin at 50 μM | % Inhibition of fungal growth at 50 μM |
|---|---|---|
| 78 | 83 | 65 |
| 79 | 100 | 93 |
| 81 | 97 | 80 |
| 82 | 100 | 100 |
| 89 | 100 | 89 |
| 116 | 100 | 82 |
| 117 | 99 | 81 |
| 119 | 95 | 77 |
| 120 | 100 | 100 |
| 121 | 100 | 98 |
| 122 | 100 | 91 |
| 123 | 100 | 96 |
| 124 | 99 | 81 |
| 125 | 96 | 76 |
| 126 | 100 | 89 |
| 128 | 83 | 71 |
| 129 | 100 | 100 |
| 132 | 100 | 85 |
| 134 | 100 | 79 |
| 136 | 93 | 71 |
| 142 | 100 | 84 |
| 143 | 96 | 73 |
| 144 | 100 | 94 |
| 148 | 90 | 67 |
| 150 | 100 | 82 |
| 151 | 100 | 100 |
| 153 | 100 | 99 |
| 154 | 100 | 100 |
| 155 | 100 | 100 |
| 162 | 100 | 100 |
| 163 | 100 | 100 |
| 165 | 99 | 83 |
| 166 | 100 | 88 |
| 169 | 100 | 84 |
| 172 | 100 | 100 |
| 173 | 100 | 85 |
| 174 | 85 | 67 |
| 175 | 100 | 92 |
| 178 | 100 | 88 |
| 180 | 100 | 100 |
| 182 | 100 | 90 |
| 183 | 82 | 79 |
| 184 | 100 | 100 |
| 185 | 100 | 89 |
| 187 | 100 | 100 |
| 189 | 100 | 94 |
| 190 | 88 | 77 |
| 191 | 100 | 100 |
| 192 | 100 | 91 |
| 193 | 100 | 92 |
| 196 | 100 | 91 |
| 202 | 100 | 84 |
| 213 | 100 | 100 |
| 214 | 100 | 93 |
| 215 | 100 | 100 |
| 216 | 100 | 100 |
| 217 | 100 | 100 |
| 219 | 81 | 71 |
| 221 | 100 | 100 |
| 222 | 91 | 78 |
| 225 | 100 | 85 |
| 240 | 100 | 98 |
| 241 | 100 | 97 |
| 242 | 100 | 100 |
| 243 | 100 | 100 |
| 244 | 99 | 82 |
| 247 | 93 | 78 |
| 255 | 100 | 90 |
| 256 | 96 | 79 |
| 259 | 97 | 82 |
| 288 | 100 | 99 |
| 290 | 82 | 72 |
| 291 | 100 | 100 |
| 292 | 100 | 86 |
| 293 | 100 | 100 |
| 294 | 100 | 84 |
| 295 | 100 | 100 |
| 297 | 100 | 85 |
| 298 | 100 | 100 |
| 301 | 100 | 100 |
| 302 | 100 | 100 |
| 303 | 100 | 90 |
| 306 | 100 | 100 |
| 307 | 100 | 92 |
| 309 | 100 | 82 |
| 310 | 100 | 96 |
| 311 | 100 | 97 |
| 312 | 100 | 99 |
| 313 | 99 | 82 |
| 315 | 100 | 100 |
| 316 | 100 | 100 |
| 317 | 100 | 90 |
| 318 | 100 | 89 |
| 319 | 100 | 89 |
| 320 | 99 | 82 |
| 322 | 100 | 99 |
| 328 | 100 | 91 |
| 329 | 100 | 97 |
| 330 | 100 | 87 |
| 331 | 99 | 79 |
| 333 | 100 | 92 |
| 334 | 100 | 90 |
| 335 | 100 | 84 |
| 338 | 100 | 100 |
| 339 | 100 | 100 |
| 340 | 100 | 95 |
| 343 | 100 | 87 |
| 344 | 100 | 89 |
| 350 | 100 | 100 |
| 351 | 100 | 100 |
| 352 | 99 | 85 |
| 353 | 99 | 85 |
| 359 | 100 | 90 |
| 360 | 100 | 96 |
| 361 | 100 | 84 |
| 364 | 99 | 81 |
| 367 | 100 | 100 |
| 368 | 100 | 93 |

The invention claimed is:

1. A compound of formula (I)

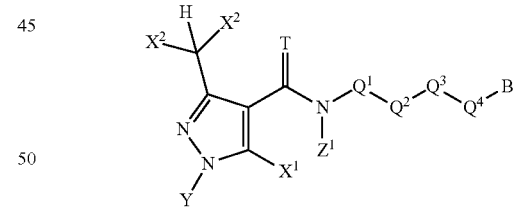

wherein
$X^1$ and $X^2$ which can be the same or different, represent a halogen atom;
Y represents a $C_1$-$C_4$-alkyl;
T represents O or S;
$Q^1$ represents $CR^1R^2$; —$CR^3$=$CR^4$—; —$CR^3$=N—O—; or —C(=W)—;
$Q^2$, $Q^3$ and $Q^4$, which can be the same or different, represent a direct bond; $CR^1R^2$; —$CR^3$=$CR^4$—; —C≡C—; —$CR^3$=N—O—; —O—N=$CR^3$—; O; S; SO; $SO_2$; $NR^5$; $SiR^6R^7$; or —C(=U)—;
B represents a phenyl ring that can be substituted by up to 5 groups X which can be the same or different; a naphthyl ring that can be substituted by up to 7 groups X which can be the same or different; a saturated, partially saturated or unsaturated, monocyclic or fused bicyclic 4-, 5-, 6-, 7-, 8-, 9-, 10-membered ring comprising from 1 up to 4 heteroatoms selected in the list consisting of N, O, S, that can be substituted by up to 6 groups X which can be the same or different; a hydrogen atom; a halogen atom; a substituted or non-substituted $C_1$-$C_{12}$-alkyl group; a $C_1$-$C_{12}$-halogenoalkyl group having 1 to 9 halogen atoms that can be the same or different; a substituted or non-substituted $C_3$-$C_8$-cycloalkyl group; a substituted or non-substituted $C_3$-$C_8$-cycloalkenyl group, a bicyclo[2.2.1]heptan-2-yl group; a tri($C_1$-$C_8$-alkyl)silyl group; a substituted or non-substituted $C_2$-$C_{12}$ alkenyl group; or a substituted or non-substituted $C_2$-$C_{12}$ alkynyl group;

X represents a halogen atom; nitro; cyano; isonitrile; hydroxy; amino; sulfanyl; pentafluoro-$\lambda^6$-sulfanyl; formyl; formyloxy; formylamino; substituted or non-substituted (hydroxyimino)-$C_1$-$C_8$-alkyl; substituted or non-substituted ($C_1$-$C_8$-alkoxyimino)-$C_1$-$C_8$-alkyl; substituted or non-substituted ($C_2$-$C_8$-alkenyloxyimino)-$C_1$-$C_8$-alkyl; substituted or non-substituted ($C_2$-$C_8$alkynyloxyimino)-$C_1$-$C_8$-alkyl; substituted or non-substituted (benzyloxyimino)-$C_1$-$C_8$-alkyl; carboxy; carbamoyl; N-hydroxycarbamoyl; carbamate; substituted or non-substituted $C_1$-$C_8$-alkyl; $C_1$-$C_8$-halogenoalkyl having 1 to 5 halogen atoms; substituted or non-substituted $C_2$-$C_8$-alkenyl; $C_2$-$C_8$-halogenoalkenyl having 1 to 5 halogen atoms; substituted or non-substituted $C_2$-$C_8$-alkynyl; $C_2$-$C_8$-halogenoalkynyl having 1 to 5 halogen atoms; substituted or non-substituted $C_1$-$C_8$-alkoxy; $C_1$-$C_8$-halogenoalkoxy having 1 to 5 halogen atoms; substituted or non-substituted $C_1$-$C_8$-alkylsulfanyl; $C_1$-$C_8$-halogenoalkylsulfanyl having 1 to 5 halogen atoms; substituted or non-substituted $C_1$-$C_8$-alkylsulfinyl; $C_1$-$C_8$-halogenoalkylsulfinyl having 1 to 5 halogen atoms; substituted or non-substituted $C_1$-$C_8$-alkylsulfonyl; $C_1$-$C_8$-halogenoalkylsulfonyl having 1 to 5 halogen atoms; substituted or non-substituted $C_1$-$C_8$-alkylamino; substituted or non-substituted di-$C_1$-$C_8$-alkylamino; substituted or non-substituted $C_2$-$C_8$-alkenyloxy; $C_2$-$C_8$-halogenoalkenyloxy having 1 to 5 halogen atoms; substituted or non-substituted $C_3$-$C_8$-alkynyloxy; $C_2$-$C_8$-halogenoalkynyloxy having 1 to 5 halogen atoms; substituted or non-substituted $C_3$-$C_7$-cycloalkyl; $C_3$-$C_7$-halogenocycloalkyl having 1 to 5 halogen atoms; substituted or non-substituted ($C_3$-$C_7$-cycloalkyl)-$C_1$-$C_8$-alkyl; substituted or non-substituted ($C_3$-$C_7$-cycloalkyl)-$C_2$-$C_8$-alkenyl; substituted or non-substituted ($C_3$-$C_7$-cycloalkyl)-$C_2$-$C_8$-alkynyl; substituted or non-substituted tri($C_1$-$C_8$-alkyOsilyl; substituted or non-substituted tri($C_1$-$C_8$-alkyl)silyl-$C_1$-$C_8$-alkyl; substituted or non-substituted $C_1$-$C_8$-alkylcarbonyl; $C_1$-$C_8$-halogenoalkylcarbonyl having 1 to 5 halogen atoms; substituted or non-substituted $C_1$-$C_8$-alkylcarbonyloxy; $C_1$-$C_8$-halogenoalkylcarbonyloxy having 1 to 5 halogen atoms; substituted or non-substituted $C_1$-$C_8$-alkylcarbonylamino; $C_1$-$C_8$-halogenoalkyl- carbonylamino having 1 to 5 halogen atoms; substituted or non-substituted $C_1$-$C_8$-alkoxycarbonyl; $C_1$-$C_8$-halogenoalkoxycarbonyl having 1 to 5 halogen atoms; substituted or non-substituted $C_1$-$C_8$-alkyloxycarbonyloxy; $C_1$-$C_8$-halogenoalkoxycarbonyloxy having 1 to 5 halogen atoms; substituted or non-substituted $C_1$-$C_8$-alkylcarbamoyl; substituted or non-substituted di-$C_1$-$C_8$alkylcarbamoyl; substituted or non-substituted $C_1$-$C_8$-alkylaminocarbonyloxy; substituted or non-substituted di-$C_1$-$C_8$-alkylaminocarbonyloxy; substituted or non-substituted N—($C_1$-$C_8$-alkyl)hydroxy carbamoyl; substituted or non-substituted $C_1$-$C_8$-alkoxycarbamoyl; substituted or non-substituted N—($C_1$-$C_8$-alkyl)-$C_1$-$C_8$-alkoxycarbamoyl; aryl that can be substituted by up to 6 groups Q which can be the same or different; arylalkyl that can be substituted by up to 6 groups Q which can be the same or different; $C_2$-$C_8$-arylalkenyl that can be substituted by up to 6 groups Q which can be the same or different; $C_2$-$C_8$-arylalkynyl that can be substituted by up to 6 groups Q which can be the same or different; aryloxy that can be substituted by up to 6 groups Q which can be the same or different; arylsulfanyl that can be substituted by up to 6 groups Q which can be the same or different; arylamino that can be substituted by up to 6 groups Q which can be the same or different; $C_1$-$C_8$-arylalkyloxy that can be substituted by up to 6 groups Q which can be the same or different; $C_1$-$C_8$-arylalkylsulfanyl that can be substituted by up to 6 groups Q which can be the same or different; or $C_1$-$C_8$-arylalkylamino that can be substituted by up to 6 groups Q which can be the same or different; or two substituent X together with the consecutive carbon atoms to which they are linked can form a 5- or 6-membered, saturated carbocycle or saturated heterocycle, which can be substituted by up to four groups Q which can be the same or different;

$Z^1$ represents a hydrogen atom; a formyl group; a substituted or non-substituted $C_1$-$C_8$-alkyl; a substituted or non substituted $C_1$-$C_8$-alkoxy; a non-substituted $C_3$-$C_7$-cycloalkyl or a $C_3$-$C_7$-cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl and di-$C_1$-$C_8$-alkylaminocarbonyl;

$R^1$ and $R^2$ independently represent a hydrogen atom; a halogen atom; cyano; substituted or non-substituted $C_1$-$C_{12}$-alkyl; substituted or non-substituted $C_2$-$C_{12}$-alkenyl; substituted or non-substituted $C_2$-$C_{12}$-alkynyl; substituted or non-substituted $C_3$-$C_7$-cycloalkyl; $C_1$-$C_{12}$-halogenoalkyl having 1 to 5 halogen atoms; substituted or non-substituted $C_1$-$C_8$-alkoxy; substituted or non-substituted $C_1$-$C_8$-alkylsulfanyl; substituted or non-substituted $C_1$-$C_8$-alkylamino; substituted or non-substituted di-($C_1$-$C_8$-alkyl)amino; or substituted or non-substituted $C_1$-$C_8$-alkoxycarbonyl; or $R^1$ and $R^2$ are a $C_2$-$C_5$-alkylene group that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different; or The $R^1$ substituent of the group $Q^i$ and the $R^1$ substituent of the group $Q^{i+1}$, i being an integer between 1 and 3, together with the consecutive carbon atoms to which they are linked can form a 3-, 4-, 5-, -6 or 7-membered saturated carbocycle that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different; or The $R^1$ substituent of the group $Q^i$ and the $R^1$ substituent of the group $Q^{i+2}$, i being an integer between 1 and 2, together with the consecutive carbon atoms to which they are linked can form a 3-, 4-, 5-, 6- or 7-membered saturated carbocycle that can be substituted by up to four groups that can be the same or different and that can be selected in the list consisting of halogen atoms, $C_1$-$C_8$-alkyl or $C_1$-$C_2$-halogenoalkyl comprising up to 5 halogen atoms that can be the same or different;

$R^3$ and $R^4$ independently represent a hydrogen atom; substituted or non-substituted $C_1$-$C_8$-alkyl; substituted or non-substituted $C_2$-$C_8$-alkenyl; substituted or non-substituted $C_2$-$C_8$-alkynyl; substituted or non-substituted $C_3$-$C_7$-cycloalkyl; or $C_1$-$C_8$-halogenoalkyl having 1 to 5 halogen atoms; $R^5$ represents a hydrogen atom; a substituted or non-substituted $C_1$-$C_8$-alkyl; a $C_1$-$C_8$-halogenoalkyl comprising up to 9 halogen atoms that can be the same or different; a substituted or non-substituted $C_2$-$C_8$-alkenyl; a $C_2$-$C_8$-halogenoalkenyl comprising up to 9 halogen atoms that can be the same or different; a substituted or non-substituted $C_3$-$C_8$-alkynyl; a $C_3$-$C_8$-halogenoalkynyl comprising up to 9 halogen atoms that can be the same or different; a substituted or non-substituted $C_3$-$C_7$-cycloalkyl; a $C_3$-$C_7$-halogeno-cycloalkyl comprising up to 9 halogen atoms that can be the same or different; a substituted or non-substituted $C_3$-$C_7$-cycloalkyl-$C_1$-$C_8$-alkyl; formyl; a substituted or non-substituted $C_1$-$C_8$-alkylcarbonyl; $C_1$-$C_8$-halogenoalkylcarbonyl comprising up to 9 halogen atoms that can be the same or different; a substituted or non-substituted $C_1$-$C_8$-alkoxycarbonyl; $C_1$-$C_8$-halogenoalkoxycarbonyl comprising up to 9 halogen atoms that can be the same or different; a substituted or non-substituted $C_1$-$C_8$-alkylsulphonyl; $C_1$-$C_8$-halogenoalkylsulphonyl comprising up to 9 halogen atoms that can be the same or different; phenylmethylene that can be substituted by up to 7 groups Q which can be the same or different; or phenylsulphonyl that can be substituted by up to 5 groups Q which can be the same or different;

$R^6$ and $R^7$ independently represent a substituted or non-substituted $C_1$-$C_8$-alkyl;

W represents O; or S;

U represents O; S; N—$OR^a$; or N—CN;

$R^a$ represents a hydrogen atom; a substituted or non-substituted $C_1$-$C_4$-alkyl; or a $C_1$-$C_4$-halogenoalkyl comprising up to 7 halogen atoms that can be the same or different;

Q independently represents a halogen atom; cyano; nitro; substituted or non-substituted $C_1$-$C_8$-alkyl; $C_1$-$C_8$-halogenoalkyl having 1 to 9 halogen atoms that can be the same or different; substituted or non-substituted $C_1$-$C_8$-alkoxy; $C_1$-$C_8$-halogenoalkoxy having 1 to 9 halogen atoms that can be the same or different; substituted or non-substituted $C_1$-$C_8$-alkylsulfanyl; $C_1$-$C_8$-halogenoalkylsulfanyl having 1 to 9 halogen atoms that can be the same or different; substituted or non-substituted tri($C_1$-$C_8$)alkylsilyl; substituted or non-substituted tri($C_1$-$C_8$)alkylsilyl-$C_1$-$C_8$-alkyl; substituted or non-substituted ($C_1$-$C_8$-alkoxyimino)-$C_1$-$C_8$-alkyl; substituted or non-substituted (benzyloxyimino)-$C_1$-$C_8$-alkyl;

with the proviso that -$Q^1$-$Q^2$-$Q^3$-$Q^4$- does not represent $CR^1R^2$ when B represents a substituted or non-substituted phenyl, naphthyl or 2-pyridyl ring;

or that -$Q^1$-$Q^2$-$Q^3$-$Q^4$- does not represent $[CR^1R^2]_2$ or $CR^1R^2$—C(=W)— or a cycloalkyl-1,2-diyl group, when B represents a substituted or non-substituted phenyl, naphthyl or heterocyclic ring;

or that $Z^1$ does not represent a hydrogen atom when -$Q^1$-$Q^2$- represents a unsubstituted cyclohexyl-1,2-diyl group and -$Q^3$-$Q^4$- represents a substituted or non-substituted cyclopropyl-1,2-diyl group;

as well as its salts, N-oxides, and optically active isomers.

2. A compound according to claim 1 wherein $X^1$ and $X^2$ independently represent a chlorine or a fluorine atom.

3. A compound according to claim 1 wherein Y represents methyl.

4. A compound according to claim 1 wherein T represents O.

5. A compound according to claim 1 wherein B represents a substituted or non-substituted phenyl ring; a substituted or non-substituted naphthyl ring; a substituted or non-substituted pyridyl ring; a substituted or non-substituted thienyl ring; or a substituted or non-substituted benzothienyl ring.

6. A compound according to claim 1 wherein X independently represents a halogen atom; substituted or non-substituted $C_1$-$C_8$-alkyl; $C_1$-$C_8$-halogenoalkyl comprising up to 9 halogen atoms that can be the same or different; substituted or non-substituted tri($C_1$-$C_8$-alkyl)silyl; substituted or non-substituted $C_1$-$C_8$-alkoxy or $C_1$-$C_8$-halogenoalkoxy comprising up to 9 halogen atoms that can be the same or different; substituted or non-substituted $C_1$-$C_8$-alkylsulfanyl or $C_1$-$C_8$-halogenoalkylsulfanyl comprising up to 9 halogen atoms that can be the same or different; or wherein two consecutive substituents X together with the phenyl ring form a substituted or non-substituted cyclopentyl or cyclohexyl ring.

7. A compound according to claim 1 wherein X independently represents fluorine, chlorine, bromine, iodine, methyl, ethyl, propyl, isopropyl, butyl, isobutyl, secbutyl, terbutyl, cyclopropyl, cyclopentyl, cyclohexyl, trimethylsilyl, methoxy, ethoxy, methylsulfanyl, ethylsulfanyl, trifluoromethyl, trichloromethyl, difluoromethoxy, trifluoromethoxy, difluorochloromethoxy, trifluoroethoxy, difluoromethysulfanyl, trifluoromethylsulfanyl and difluorochloro-methylsulfanyl.

8. A compound according to claim 1 wherein $Z^1$ represents a hydrogen atom; a non-substituted $C_3$-$C_7$ cycloalkyl; or a $C_3$-$C_7$ cycloalkyl substituted by up to 10 groups or atoms that can be the same or different and that can be selected in the list consisting of halogen atoms, $C_1$-$C_8$-alkyl, $C_1$-$C_8$-halogenoalkyl comprising up to 9 halogen atoms that can be the same or different, $C_1$-$C_8$-alkoxy and $C_1$-$C_8$-halogenoalkoxy comprising up to 9 halogen atoms that can be the same or different.

9. A compound according to claim 1 wherein $Q^1$ represents $CR^1R^2$.

10. A compound according to claim 1 wherein $Q^2$, $Q^3$ and $Q^4$, which can be the same or different, represents a direct bond; $CR^1R^2$; or O.

11. A compound according to claim 1 wherein $Q^2$ represents $CR^1R^2$, $Q^3$ represents a direct bond or O, and $Q^4$ represent a direct bond.

12. A compound according to claim 1 wherein $R^1$ and $R^2$ independently represent a hydrogen atom, a fluorine atom, a substituted or non-substituted $C_1$-$C_8$-alkyl or a substituted or non-substituted $C_1$-$C_8$alkoxy.

13. A compound according to claim 1 wherein the $R^1$ substituent of the group $Q^i$ and the $R^1$ substituent of the group $Q^{i+1}$, i being an integer between 1 and 3, together with the consecutive carbon atoms to which they are linked can form an optionally mono or polysubstituted 3-, 4-, 5-, 6- or 7-membered saturated carbocycle.

14. A compound according to claim 13 wherein the $R^1$ substituent of the group $Q^i$ and the $R^1$ substituent of the group $Q^{i+1}$, i being an integer between 1 and 3, together with the consecutive carbon atoms to which they are linked can form a cyclopentyl, cyclohexyl or cycloheptyl group that can be substituted by up to four groups that can be the same or different and that can be selected in the list consisting of fluorine, chlorine, methyl, ethyl, propyl, isopropyl, isobutyl, secbutyl, terbutyl, trifluoromethyl or difluoromethyl.

15. A compound according to claim 14 wherein
-$Q^1$-$Q^2$- represents an optionally mono or polysubstituted cyclopentyl-1,2-diyl, cyclohexyl-1,2-diyl or cycloheptyl-1,2-diyl group; and
-$Q^3$-$Q^4$-B represents a bicyclo[2.2.1]heptan-2-yl group, $A^1$, $A^2$, $A^3$ or $A^4$ wherein

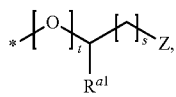

$A^1$ represents wherein
$R^{a1}$ represents hydrogen, $C_1$-$C_4$-alkyl or $C_1$-$C_4$-haloalkyl;
Z represents —$CR^{a2}R^{a3}R^{a4}$ or —$SiR^{a2}R^{a3}R^{a4}$;
s represents 0, 1, 2 or 3;
t represents 0 or 1;
$R^{a2}$, $R^{a3}$, $R^{a4}$ independently of one another represent hydrogen, halogen $C_1$-$C_4$-alkyl or $C_1$-$C_4$-haloalkyl; or
$R^{a3}$ and $R^{a4}$ together with the carbon atom to which they are attached form an optionally substituted saturated or insaturated 3- to 6-membered carbocyclic ring;

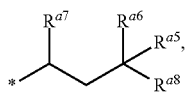

$A^2$ represents wherein
$R^{a6}$ represent hydrogen, halogen, $C_1$-$C_8$-alkyl or $C_1$-$C_8$-haloalkyl;
$R^{a5}$, $R^{a7}$, $R^{a8}$ independently of one another represent hydrogen, methyl or ethyl;

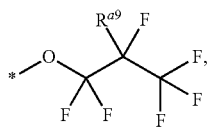

$A^3$ represents wherein
$R^{a9}$ represent hydrogen or fluorine;

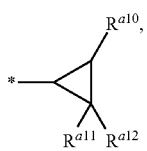

$A^4$ represents wherein
$R^{a10}$ represent optionally substituted $C_2$-$C_{12}$-alkyl, optionally substituted $C_2$-$C_{12}$-alkenyl, optionally substituted $C_2$-$C_{12}$-alkynyl, optionally substituted $C_3$-$C_8$-cycloalkyl, optionally substituted phenyl or heterocyclyl;
$R^{a11}$ represent hydrogen or halogen; and
$R^{a12}$ represent hydrogen or halogen.

16. A compound according to claim 15 wherein
$R^{a1}$ represents hydrogen or methyl;
s represents 0 or 1;
$R^{a2}$ represents chlorine, methyl, ethyl, isopropyl or trifluoromethyl;
$R^{a3}$ represents chlorine, methyl, ethyl, isopropyl or trifluoromethyl;
$R^{a4}$ represents hydrogen, chlorine, methyl, ethyl, isopropyl or trifluoromethyl;
$R^{a5}$ represents hydrogen or methyl;
$R^{a6}$ represents hydrogen;
$R^{a7}$ represents hydrogen or methyl;
$R^{a8}$ represents fluorine, chlorine, methyl, ethyl or trifluoromethyl;
$R^{a9}$ represent hydrogen or fluorine;
$R^{a10}$ represents ethyl, propyl, isopropyl, butyl, secbutyl, terbutyl, cyclopropyl, cyclobutyl, cyclopentyl, cyclohexyl, α-methylcyclopropyl, 4-fluorophenyl, 4-bromophenyl, 2-thienyl, 3-thienyl
or 2-fury;
$R^{a11}$ represents hydrogen;
$R^{a12}$ represents hydrogen.

17. A compound according to claim 1 wherein the $R^1$ substituent of the group $Q^i$ and the $R^1$ substituent of the group $Q^{i+2}$, i being an integer between 1 and 2, together with the consecutive carbon atoms to which they are linked can form an cyclohexyl group that can be substituted by up to four groups that can be the same or different and that can be selected in the list consisting of fluorine, chlorine, methyl, ethyl, propyl, isopropyl, isobutyl, secbutyl, terbutyl, trifluoromethyl or difluoromethyl.

18. A compound according to claim 17 wherein -$Q^1$-$Q^2$-$Q^3$- represents an optionally mono or polysubstituted cyclohexyl-1,3-diyl and -$Q_4$-B represents a bicyclo[2.2.1]heptan-2-yl group, $A^1$, $A^2$, $A^3$ or $A^4$ group as defined in claim 15 or 16.

19. A compound according to claim 1 wherein $R^3$ and $R^4$ independently represent a hydrogen atom, or a substituted or non-substituted $C_1$-$C_8$-alkyl.

20. A compound according to claim 1 wherein $R^5$ represents a substituted or non-substituted $C_1$-$C_8$-alkyl.

21. A compound according to claim 1 wherein $R^6$ and $R^7$ independently represent a non-substituted $C_1$-$C_8$-alkyl.

22. A compound according to claim 1 wherein U represents O or N—O—($C_1$-$C_4$-alkyl).

23. A fungicide composition comprising, as an active ingredient, an effective amount of a compound of formula (I) according to claim 1 and an agriculturally acceptable support, carrier or filler.

24. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

25. A method for controlling phytopathogenic fungi of crops, characterized in that an agronomically effective and substantially non-phytotoxic quantity of a composition according to claim 23 is applied to the soil where plants grow or are capable of growing, to the leaves and/or the fruit of plants or to the seeds of plants.

* * * * *